(12) United States Patent
Jackson

(10) Patent No.: US 11,241,520 B2
(45) Date of Patent: *Feb. 8, 2022

(54) COMPOSITIONS AND DEVICES INCORPORATING WATER-INSOLUBLE THERAPEUTIC AGENTS AND METHODS OF THE USE THEREOF

(71) Applicant: COOK MEDICAL TECHNOLOGIES LLC, Bloomington, IN (US)

(72) Inventor: John K. Jackson, West Vancouver (CA)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 16/749,415

(22) Filed: Jan. 22, 2020

(65) Prior Publication Data
US 2020/0155730 A1 May 21, 2020

Related U.S. Application Data

(63) Continuation-in-part of application No. 16/408,663, filed on May 10, 2019, now Pat. No. 11,058,805, (Continued)

(51) Int. Cl.
*A61L 31/16* (2006.01)
*A61K 31/353* (2006.01)
(Continued)

(52) U.S. Cl.
CPC .......... *A61L 31/16* (2013.01); *A61K 31/337* (2013.01); *A61K 31/353* (2013.01); *A61K 31/436* (2013.01); *A61K 31/58* (2013.01); *A61L 27/34* (2013.01); *A61L 27/44* (2013.01); *A61L 27/54* (2013.01); *A61L 29/08* (2013.01); *A61L 29/085* (2013.01); *A61L 29/16* (2013.01);
(Continued)

(58) Field of Classification Search
None
See application file for complete search history.

(56) References Cited

U.S. PATENT DOCUMENTS 8,192,479 B2 6/2012 Paul
8,642,063 B2 2/2014 Sarasam et al.
(Continued)

FOREIGN PATENT DOCUMENTS

EP 2 098 230 B1 6/2012
EP 2 962 707 A1 1/2016
(Continued)

OTHER PUBLICATIONS

Office Action for U.S. Appl. No. 14/454,345, dated Dec. 18, 2015, 14 pgs.
(Continued)

*Primary Examiner* — Melissa S Mercier
(74) *Attorney, Agent, or Firm* — Crowell & Moring LLP

(57) ABSTRACT

Various aspects of the present disclosure provide compositions including a water-insoluble therapeutic agent and a gallate-containing compound. Other aspects provide methods of using such compositions.

19 Claims, 39 Drawing Sheets

Related U.S. Application Data which is a continuation of application No. 16/001,514, filed on Jun. 6, 2018, now Pat. No. 10,328,183, which is a continuation of application No. 15/386,662, filed on Dec. 21, 2016, now Pat. No. 10,016,536, which is a continuation of application No. 14/880,332, filed on Oct. 12, 2015, now Pat. No. 9,572,914, which is a continuation of application No. 14/454,325, filed on Aug. 7, 2014, now Pat. No. 9,180,226.

(51) Int. Cl.

| | | |
|---|---|---|
| *A61L 31/10* | (2006.01) | |
| *A61L 29/16* | (2006.01) | |
| *A61L 29/08* | (2006.01) | |
| *A61L 27/54* | (2006.01) | |
| *A61L 27/44* | (2006.01) | |
| *A61L 27/34* | (2006.01) | |
| *A61L 31/08* | (2006.01) | |
| *A61M 25/10* | (2013.01) | |
| *A61M 25/09* | (2006.01) | |
| *A61K 31/58* | (2006.01) | |
| *A61K 31/436* | (2006.01) | |
| *A61K 31/337* | (2006.01) | |

(52) U.S. Cl.
CPC .............. *A61L 31/08* (2013.01); *A61L 31/10* (2013.01); *A61M 25/09* (2013.01); *A61M 25/10* (2013.01); *A61L 2300/416* (2013.01); *A61L 2300/426* (2013.01); *A61L 2300/602* (2013.01); *A61L 2300/606* (2013.01); *A61L 2300/61* (2013.01); *A61L 2420/06* (2013.01); *A61M 2025/105* (2013.01); *H05K 999/99* (2013.01)

(56) References Cited

U.S. PATENT DOCUMENTS

| | | | |
|---|---|---|---|
| 8,916,227 | B2 | 12/2014 | Horres et al. |
| 9,180,226 | B1 * | 11/2015 | Jackson .............. A61K 31/337 |
| 9,572,914 | B2 * | 2/2017 | Jackson .............. A61L 27/44 |
| 9,655,998 | B2 | 5/2017 | Gemborys |
| 10,016,526 | B2 | 7/2018 | Shim |
| 10,016,536 | B2 * | 7/2018 | Jackson .............. A61K 31/58 |
| 10,328,183 | B2 * | 6/2019 | Jackson .............. A61K 31/436 |
| 2003/0044474 | A1 | 3/2003 | Tao et al. |
| 2005/0019404 | A1 | 1/2005 | Sung et al. |
| 2005/0027000 | A1 | 2/2005 | Reed et al. |
| 2005/0037048 | A1 | 2/2005 | Song |
| 2005/0064011 | A1 | 3/2005 | Song et al. |
| 2005/0119404 | A1 | 6/2005 | Luo et al. |
| 2005/0163821 | A1 | 7/2005 | Sung et al. |
| 2006/0034885 | A1 | 2/2006 | Sung et al. |
| 2006/0040894 | A1 | 2/2006 | Hunter et al. |
| 2007/0054868 | A1 | 3/2007 | Weinstein et al. |
| 2007/0141100 | A1 | 6/2007 | Sung et al. |
| 2007/0178138 | A1 | 8/2007 | Pal et al. |
| 2008/0020013 | A1 | 1/2008 | Reyes et al. |
| 2008/0103103 | A1 * | 5/2008 | Memarzadeh ....... A61K 31/353 514/27 |
| 2008/0255510 | A1 | 10/2008 | Wang |
| 2010/0168837 | A1 | 7/2010 | Magnuson et al. |
| 2010/0233228 | A1 | 9/2010 | Speck |
| 2010/0261662 | A1 | 10/2010 | Schreck et al. |
| 2010/0272773 | A1 | 10/2010 | Kangas et al. |
| 2010/0285085 | A1 | 11/2010 | Stankus et al. |
| 2011/0008260 | A1 | 1/2011 | Flanagan et al. |
| 2011/0015664 | A1 | 1/2011 | Kangas et al. |
| 2011/0033525 | A1 | 2/2011 | Liu |
| 2011/0111057 | A1 | 5/2011 | Reed et al. |
| 2011/0144577 | A1 | 6/2011 | Stankus et al. |
| 2011/0171128 | A1 | 7/2011 | Beliveau et al. |
| 2011/0195910 | A1 | 8/2011 | Ling et al. |
| 2012/0148567 | A1 | 6/2012 | Kurisawa et al. |
| 2012/0156135 | A1 | 6/2012 | Farokhzad et al. |
| 2012/0269901 | A1 | 10/2012 | Reed et al. |
| 2012/0277719 | A1 | 11/2012 | Shukla et al. |
| 2012/0277852 | A1 | 11/2012 | Shukla et al. |
| 2012/0316633 | A1 | 12/2012 | Flanagan et al. |
| 2012/0323211 | A1 | 12/2012 | Ogle et al. |
| 2012/0329738 | A1 | 12/2012 | Liu |
| 2013/0004488 | A1 | 1/2013 | Kurisawa et al. |
| 2013/0046237 | A1 | 2/2013 | Speck |
| 2014/0227192 | A1 | 8/2014 | Speck et al. |
| 2014/0227193 | A1 | 8/2014 | Speck et al. |
| 2014/0227194 | A1 | 8/2014 | Speck et al. |
| 2017/0100524 | A1 | 4/2017 | Jackson et al. |

FOREIGN PATENT DOCUMENTS

| | | | | |
|---|---|---|---|---|
| EP | 2 982 388 A1 | 2/2016 | | |
| EP | 2 982 389 A1 | 2/2016 | | |
| EP | 2 944 332 B1 | 8/2016 | | |
| EP | 2 709 711 B1 | 11/2016 | | |
| EP | 2 857 049 B1 | 11/2016 | | |
| JP | 2007-526793 A | 9/2007 | | |
| JP | 2008-253707 A | 10/2008 | | |
| JP | 2012-533338 A | 12/2012 | | |
| WO | WO 2000/32238 A1 | 6/2000 | | |
| WO | WO 2010/124098 A2 | 10/2010 | | |
| WO | WO 2011/019323 A1 | 2/2011 | | |
| WO | WO-2011014850 A2 * | 2/2011 | ........... A61K 31/137 | |
| WO | WO 2011/071630 A1 | 6/2011 | | |
| WO | WO 2011/112156 A1 | 9/2011 | | |
| WO | WO 2013/053809 A1 | 4/2013 | | |
| WO | WO 2015/171079 A1 | 11/2015 | | |
| WO | WO 2017/072545 A1 | 5/2017 | | |

OTHER PUBLICATIONS

Office Action for U.S. Appl. No. 14/454,345, dated Jun. 14, 2016, 18 pgs.
Extended European Search Report for EP 15179148.0 dated Dec. 7, 2015, 7 pgs.
Extended European Search Report for EP 15179160.5 dated Dec. 7, 2015, 7 pgs.
Examination Report for EP 15179148.0 dated Oct. 26, 2016, 5 pgs.
Japanese Office Action with English language translation for related application No. JP 2015-155874 dated Aug. 24, 2016, 5 pgs.
Japanese Office Action with English language translation for related application No. JP 2015-153847 dated Aug. 16, 2016, 7 pgs.
Wang et al., "Epigallocatechin-3-gallete decreases thrombin/paclitaxel-induced endothelial tissue factor expression via the inhibition of e-June terminal NH2 kinase phosphorylation", Biochemical and Biophysical Research Communication, Jan. 2010, vol. 391, No. 1, pp. 716-721.
Office Action in U.S. Appl. No. 15/496,466, dated Jun. 27, 2017, 12 pgs.
Office Action, and English language translation thereof, in corresponding Japanese Application No. 2015-155874, dated Jul. 5, 2017, 5 pgs.
Response to Japanese Office Action, and English language translation thereof, in corresponding Japanese Application No. 2015-153847, dated Jan. 16, 2017, 5 pgs.
Decision for Patent and English translation thereof, in corresponding Japanese Application No. 2015-155874, dated Dec. 20, 2017, 4 pgs.
Decision for Patent and English translation thereof, in corresponding Japanese Application No. 2015-153847, dated May 2, 2017, 6 pgs.
Response to Search Opinion in corresponding European Application No. 15179160.5, dated Aug. 9, 2016, 10 pgs.
Response to Search Opinion in corresponding European Application No. 15179148.0, dated Aug. 10, 2016, 11 pgs.
Response to Office Action in corresponding European Application No. 15179148.0, dated Mar. 31, 2017, 62 pgs.

(56) References Cited

OTHER PUBLICATIONS

Intention to Grant in corresponding European Application No. 15179148.0, dated Oct. 23, 2017, 71 pgs.
Office Action for Japanese Application No. 2017-11242, dated Feb. 13, 2018, 7 pgs.
Batchelder et al., "In vitro transdermal delivery of the major catechins and caffeine from extract of *Camellia sinensis*," 283 International Journal of Pharmaceutics pp. 45-51 (2004).
Han, "Synergic Anticandidal Effect of Epigallocatechin-O-Gallate Combined with Amphotericin B in a Murine Model of Disseminated Candidiasis and Its Anticandidal Mechanism," 30(9) Biol. Pharm. Bull, pp. 1693-1696 (2007).
Lambert et al., "Transdermal delivery of (-)-epigallocatechin-3-gallate, a green tea polyphenol, in mice," 58 Journal of Pharmacy and Pharmacology pp. 599-604 (2006).
Narayanan et al., "Sequential release of epigallocatechin gallate and paclitaxel from PLGA-casein core/shell nanoparticles sensitizes drug-resistant breast cancer cells," 11 Nanotechnology, Biology, and Medicine pp. 1399-1406 (2015).
Park et al., "Schedule-Dependent Effect of Epigallocatechin-3-Gallate (EGCG) with Paclitaxel on H460 Cells," 76 Tuberc Respir Dis pp. 114-119 (2014).
Ramadass et al., "Paclitaxel/Epigallocatechin gallate coloaded liposome: A synergistic delivery to control the invasiveness of MDA-MB-231 breast cancer cells," 125 Colloids and Surfaces B: Biointerfaces pp. 65-72 (2015).
Stearns et al., "Synergistic Effects of the Green Tea Extract Epigallocatechin-3-gallate and Taxane in Eradication of Malignant Human Prostate Tumors," 4 Translational Oncology pp. 147-156 (2011).
Wang et al., "Sensitization to docetaxel in prostate cancer cells by green tea and quercetin," 26 Journal of Nutritional Biochemistry pp. 408-415 (2015).
Yunos et al., "Synergism from Sequenced Combinations of Curcumin and Epigallocatechin-3-gallate with Cisplatin in the Killing of Human Ovarian Cancer Cells," 31 Anticancer Research pp. 1131-1140 (2011).

* cited by examiner

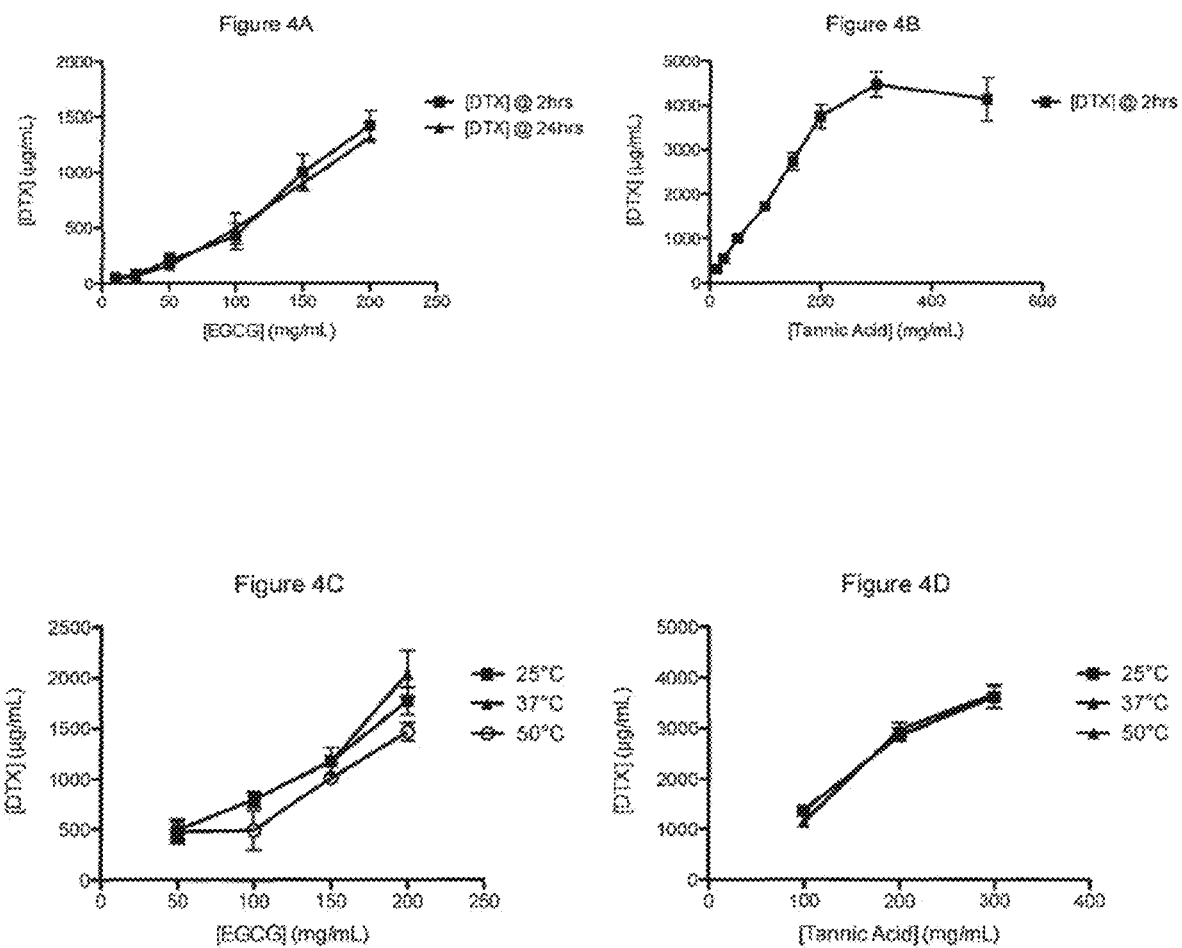

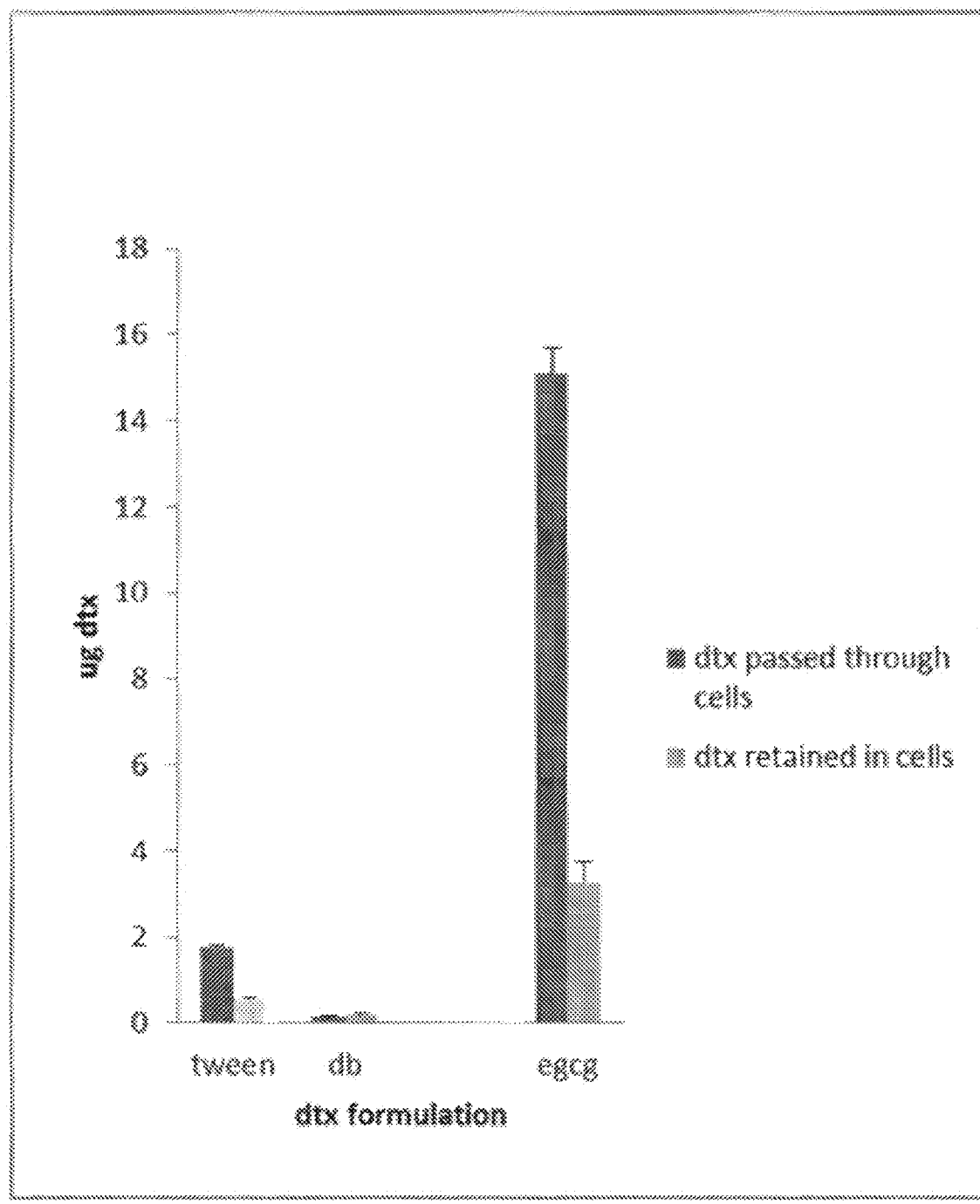
Figure 5. The uptake and transfer of docetaxel through mdck cells

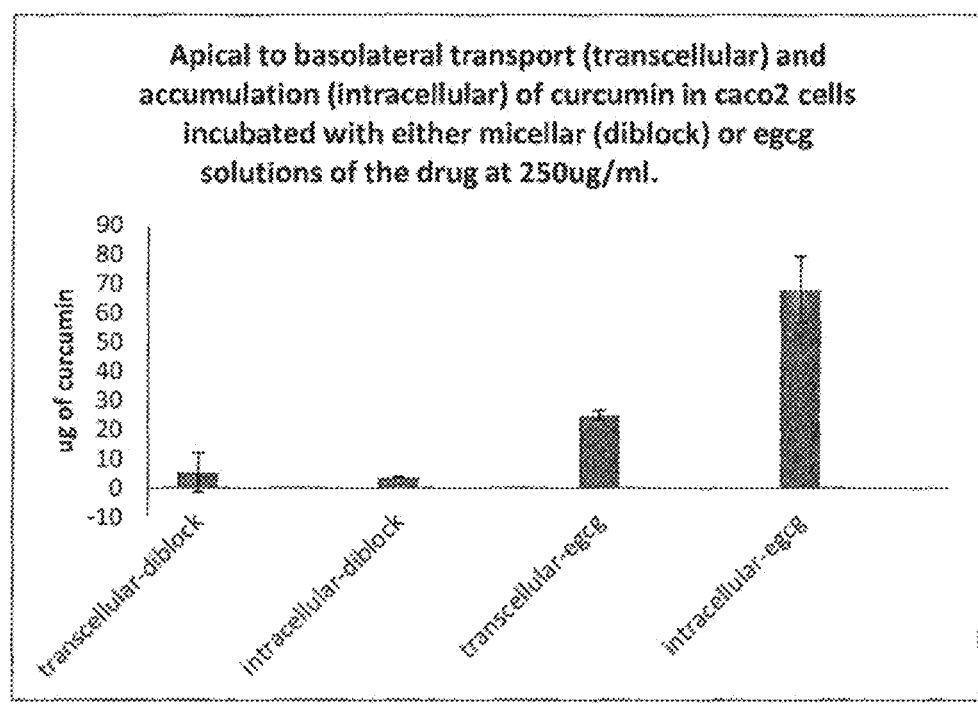
Figure 6: Transport of curcumin in and through Caco2 cells.

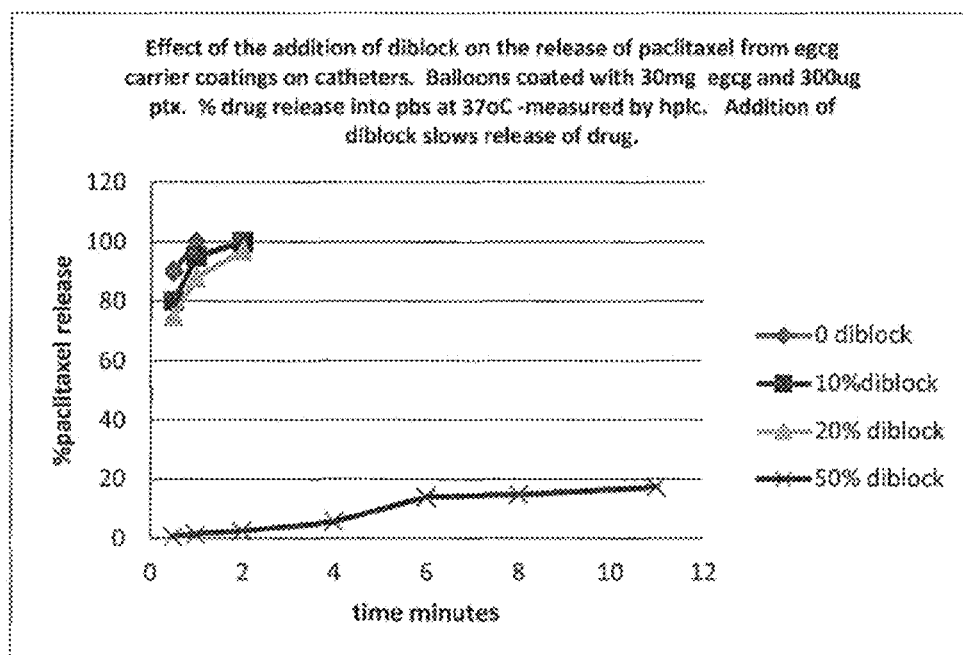
Figure 7. Effect of diblock copolymer of the release of paclitaxel from egcg coated balloon catheters.

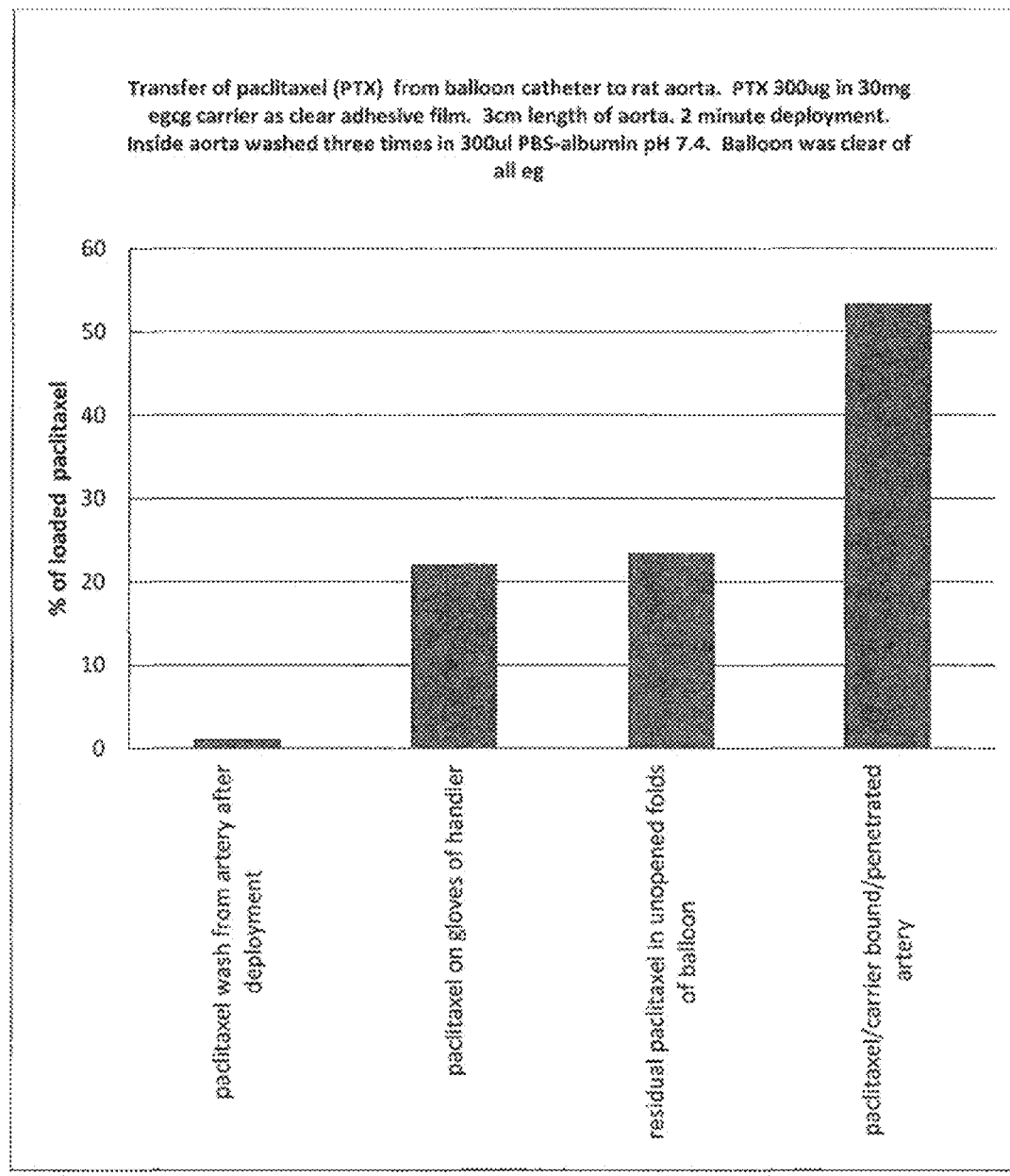
Figure 8. Transfer of paclitaxel to artery wall from EGCG coated balloon catheter.

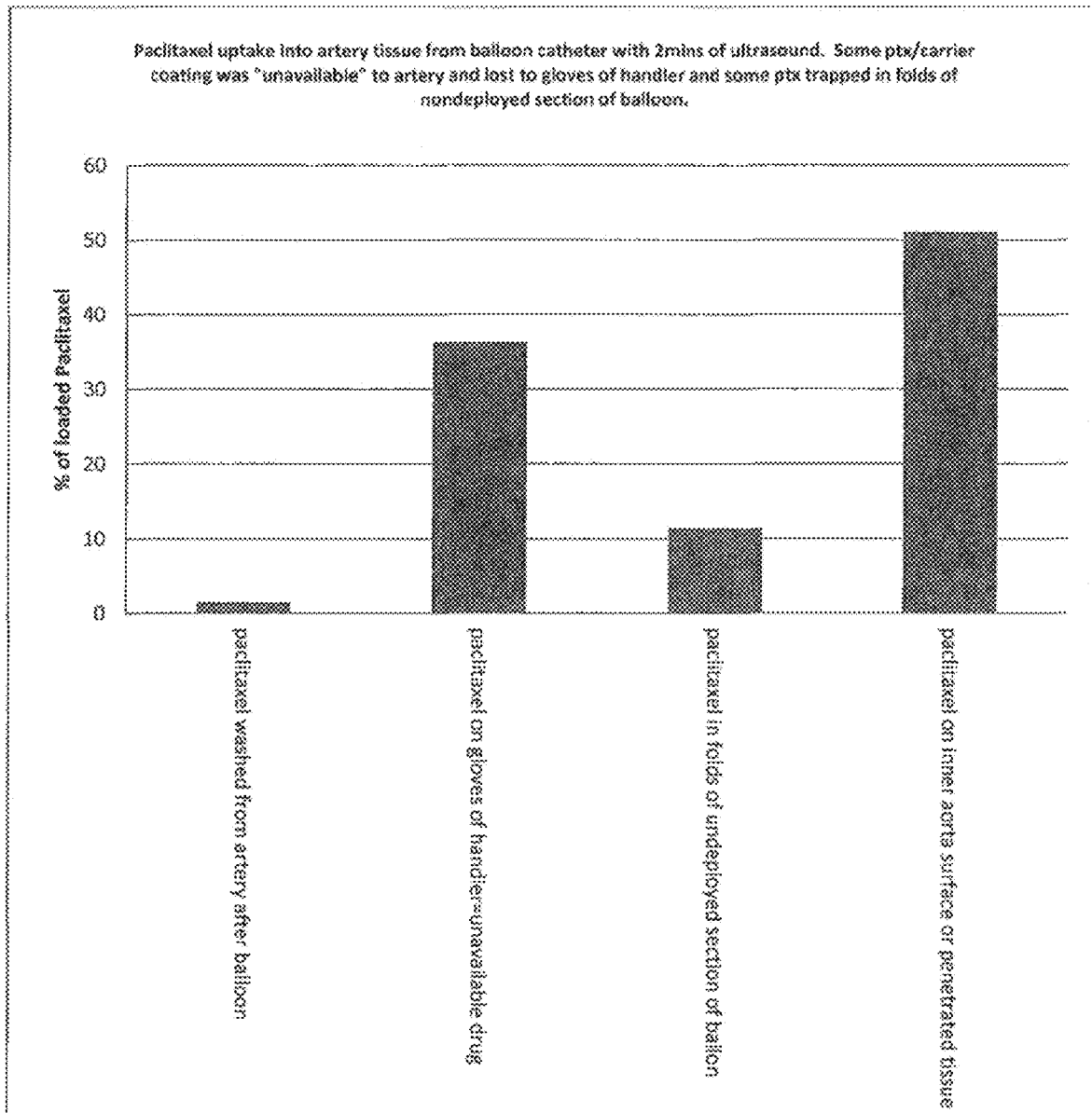
Figure 9. Effect of ultrasound on the transfer of paclitaxel to the aorta from an egeg coated catheter.

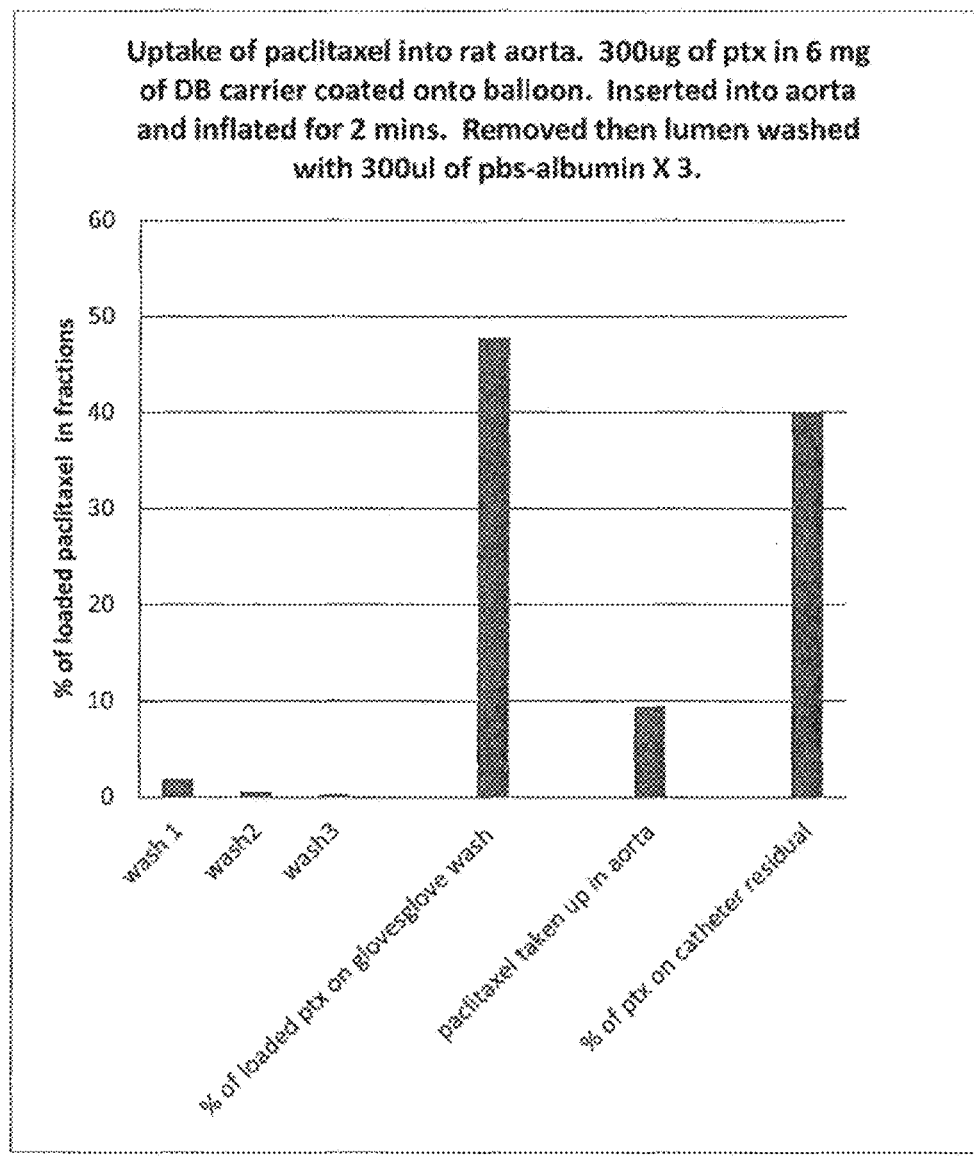
Figure 10. Transfer of paclitaxel into artery using a diblock copolymer coating.

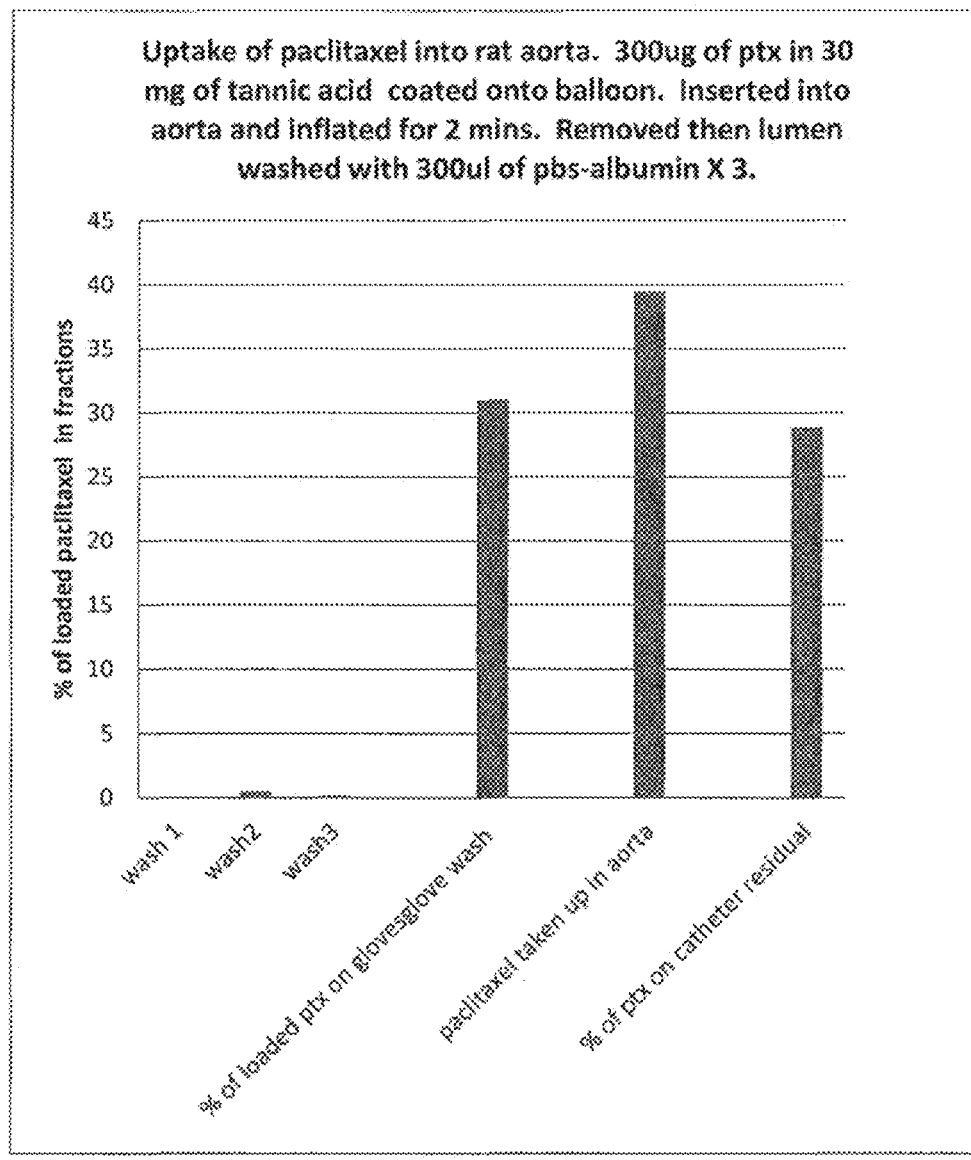
Figure 11. Transfer of paclitaxel into artery from tannic acid coated balloon catheter.

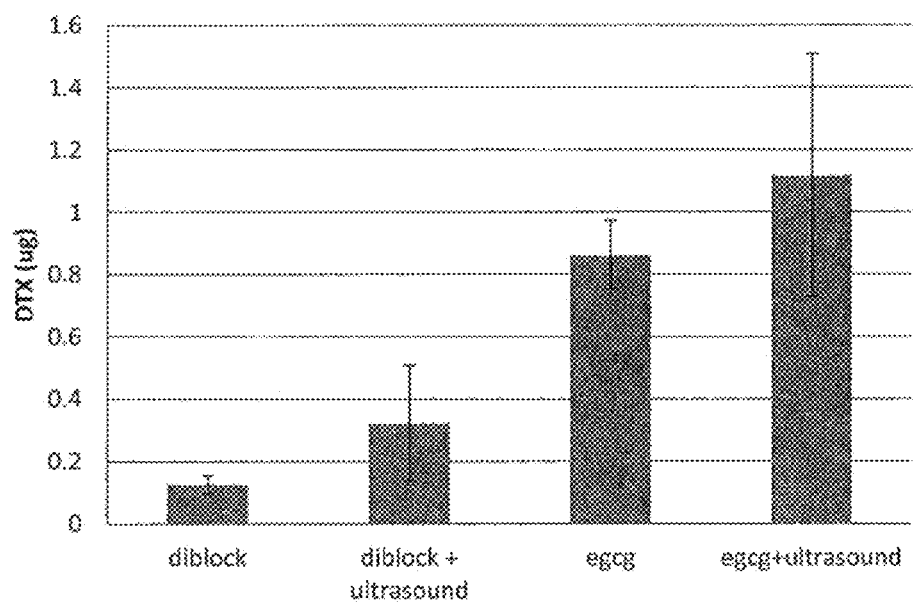

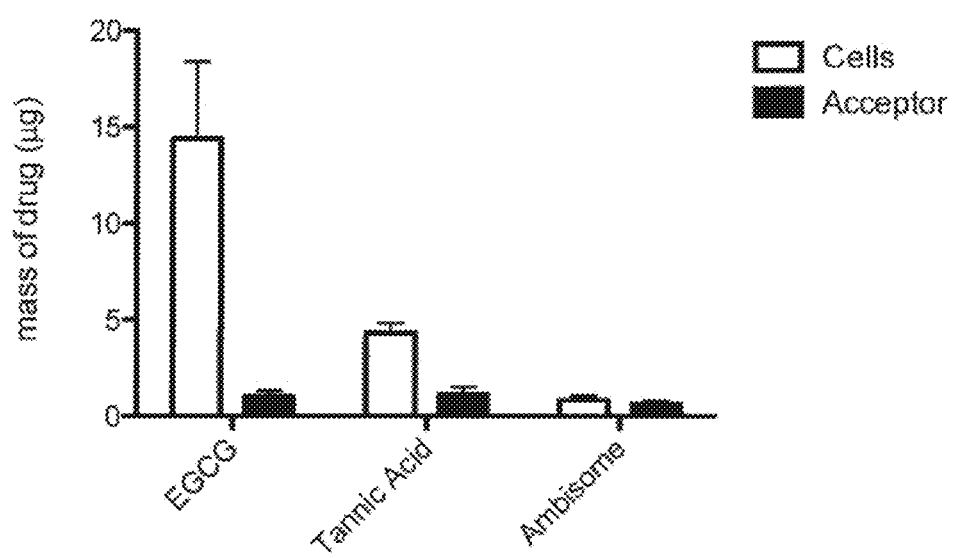
Figure 13. Uptake and transfer of amphotericin B in Caco2 cells.

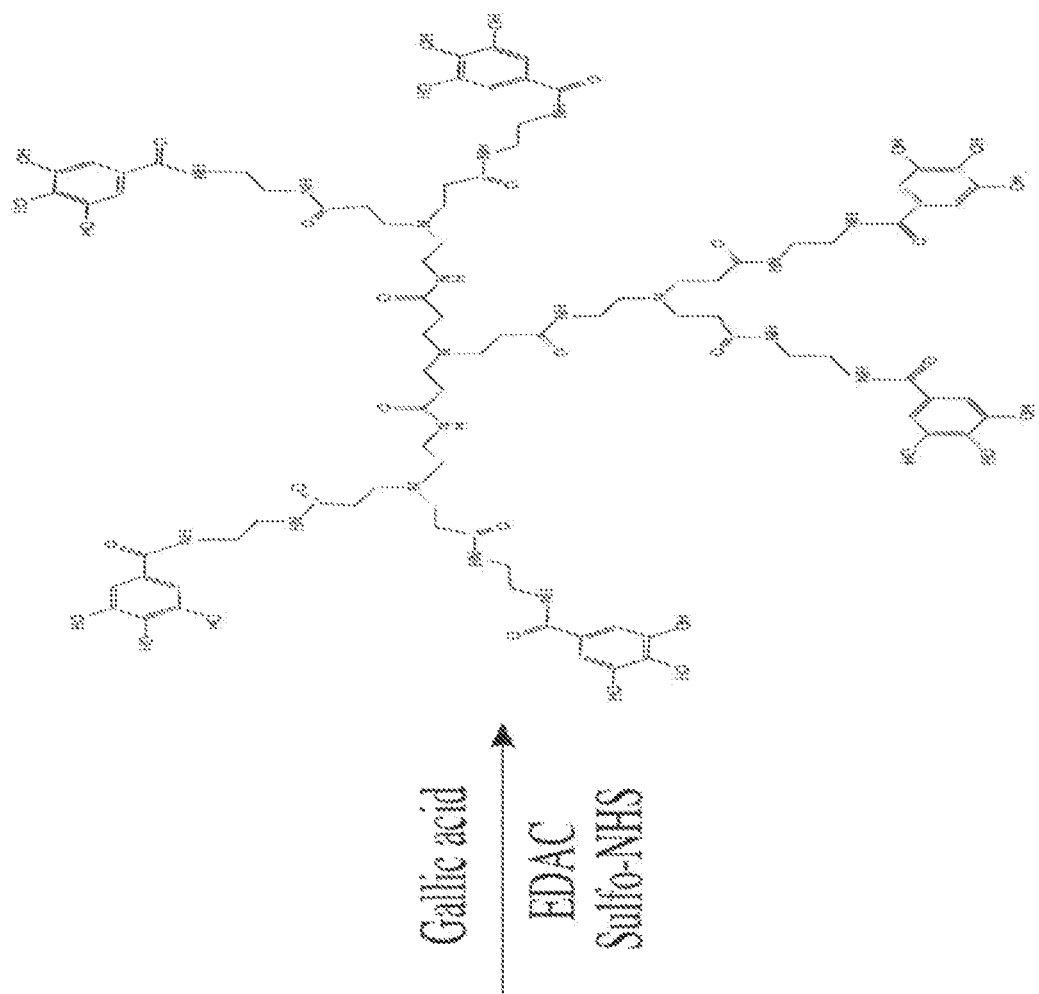
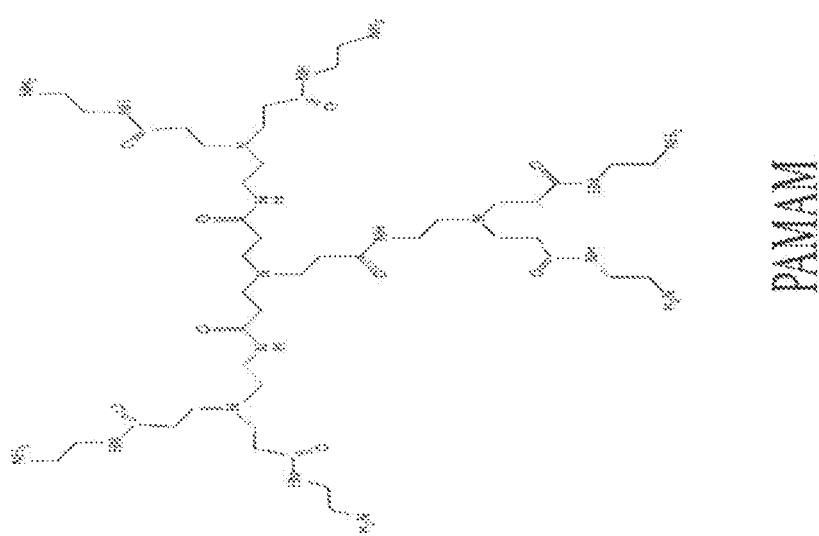
Figure 14

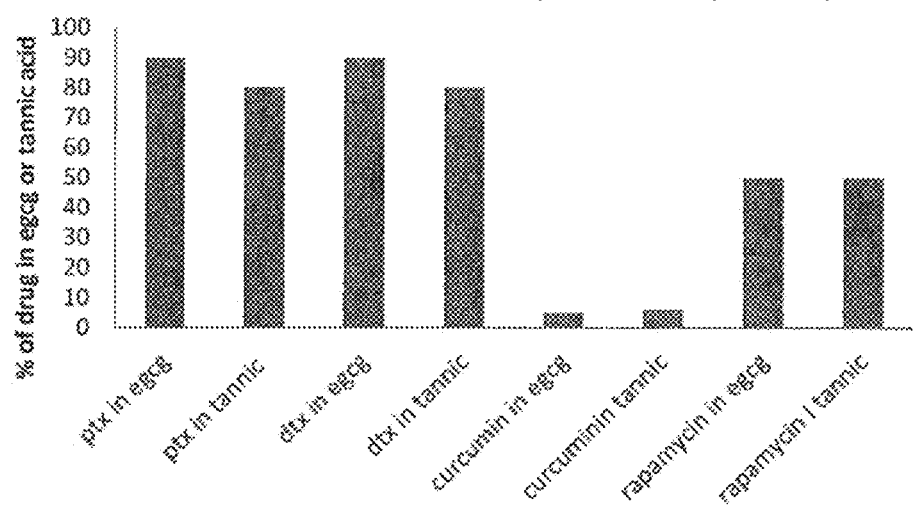
Figure 15. Limit of solubility of drugs in tannic acid or egcg coatings.

Figure 18 Release of finasteride from commercial formulations.

Figure 19. Release of finasteride from plga microspheres +/- EGCG or tannic acid.

COMPOSITIONS AND DEVICES INCORPORATING WATER-INSOLUBLE THERAPEUTIC AGENTS AND METHODS OF THE USE THEREOF

RELATED APPLICATIONS

This patent application is a continuation-in-part of U.S. patent application Ser. No. 16/408,663, filed May 10, 2019, which application is a continuation of U.S. patent application Ser. No. 16/001,514, now U.S. Pat. No. 10,328,183, filed Jun. 6, 2018, which is a continuation of U.S. patent application Ser. No. 15/386,662, filed Dec. 21, 2016, now U.S. Pat. No. 10,016,536, which is a continuation of U.S. patent application Ser. No. 14/880,332, filed Oct. 12, 2015, now U.S. Pat. No. 9,572,914, which is a continuation of U.S. patent application Ser. No. 14/454,325, filed Aug. 7, 2014, now U.S. Pat. No. 9,180,226, the entire contents of which applications are hereby incorporated by reference.

TECHNICAL FIELD

The present invention generally relates to compositions and devices including a water-insoluble therapeutic agent solubilized in a gallate-containing compound and to methods of making and using such compositions and devices.

BACKGROUND

Local delivery of a therapeutic agent can be useful in the treatment of many medical conditions. Illustratively, local delivery of a therapeutic agent within a body vessel or to a selected portion of internal body tissue can eliminate or reduce the need for systemic delivery of the therapeutic agent thus minimizing any potential adverse effect of the therapeutic agent on areas of the body not needing treatment.

Minimally invasive implantable medical devices, such as balloons, catheters and stents, can provide a platform for delivering therapeutic agents to internal body tissue. For example, balloon catheters or stents may be used to deliver a therapeutic agent directly to the target site within a body vessel such as an artery or vein.

One example of a condition that can be beneficially treated by local administration of a therapeutic agent with a balloon catheter is the delivery of a therapeutic agent in combination with percutaneous transluminal coronary angioplasty (PTCA), a technique used to dilate stenotic portions of blood vessels. In such cases, a catheter balloon coated with the therapeutic agent can be positioned at a blocked lumen or target site during PTCA, and the balloon is inflated causing dilation of the vessel lumen. The catheter balloon is pressed against the vessel wall for delivery of the therapeutic agent to the vessel wall. The balloon is deflated and the catheter is then removed from the target site and the patient's lumen thereby allowing blood to more freely flow through the now less restricted lumen.

Although PTCA and related procedures aid in alleviating intraluminal constrictions, such constrictions or blockages may reoccur in many cases. The cause of these recurring obstructions, termed restenosis, may be due to the body responding to the surgical procedure. Restenosis of the vessel may develop over several months after the procedure, and may require another angioplasty procedure or a surgical bypass operation to correct. Proliferation and migration of smooth muscle cells (SMC) from the media layer of the lumen to the intimal layer cause an excessive production of extracellular matrices (ECM), which is believed to be one of the leading contributors to the development of restenosis. The extensive thickening of tissues narrows the lumen of the blood vessel, constricting or blocking the blood flow through the vessel. Therapeutic agents that inhibit restenosis may be locally delivered during PTCA from a catheter or by placement of a stent configured to continue to release the therapeutic agent after the PTCA procedure.

The delivery of the therapeutic agent from coatings in these and other minimally invasive procedures can be complicated by the need both to have a coating that is durable during delivery, but which effectively delivers the therapeutic agent when implanted in the region where local treatment is desired. Furthermore, numerous therapeutic agents are not freely soluble in an aqueous environment. Because natural biological environments are aqueous, it can occur that a coating containing a water-insoluble therapeutic agent is sufficiently durable during travel to the intended delivery site, but then fails to optimally deliver the therapeutic agent at the site.

Therapeutic agents may also be useful in dermal applications, for example when formulated for topical application to the skin. Topical drug preparations include, for example, creams, pastes, gels, lotions, ointments, and the like. In general, there are several clinical reasons for delivering drugs via the skin. These include treating local diseases of the skin (e.g., psoriasis), and/or for delivering the drug through the skin into the systemic circulation (e.g., nicotine). Although attractive, these delivery routes are strongly impeded by the skin's outer layer (epidermis) and in particular by the stratum corneum. The stratum corneum consists of many layers of dead cells packed tightly together to create a densely-packed, hydrophobic barrier. Some drugs, such as corticosteroids are able to penetrate this barrier. However, many drugs are unable to penetrate this barrier. For example, water soluble drugs do not pass well through such environments. Larger molecules can also be excluded from penetration due to their size. Pharmaceutical scientists have described a number of penetration enhancers that may be added to creams and gels to assist drug transfer, however this route of administration still can result in low levels of uptake for most drugs.

Drug movement through the stratum corneum depends in part on the diffusion gradient of the drug across the skin. Although hydrophilic (water soluble) drugs may be formulated at higher concentrations in solution in aqueous gels and creams to create higher diffusion gradients, these drug molecules do not transfer across the epidermis due to their hydrophilicity. Hydrophobic drugs also present challenges in aqueous formulations because these drugs do not readily dissolve in water, making higher diffusion gradients difficult or impossible to achieve. Some formulations use a micellar technique to improve aqueous formulations, however known micellar formulations are not optimal. Instead of creating a true solution, where the drug molecules are free to move within the water, micellar formulations sequester the drug molecules within micelle structures, limiting the mobility of the drug molecules and limiting the ability to create high drug gradients across the skin.

Needs thus exist for compositions, coatings, and coated implantable medical devices which enable the beneficial delivery of a water-insoluble therapeutic agent locally to a site intended for treatment.

SUMMARY

One aspect of the present disclosure relates to compositions including at least one water-insoluble therapeutic agent solubilized in a matrix of at least one gallate containing compound. In some embodiments, the gallate containing compound increases the solubility of the water-insoluble therapeutic agent in an aqueous medium and/or enhances the delivery of the water-insoluble therapeutic agent to a vessel wall and into the tissue of a patient. In certain embodiments, the gallate containing compound and the water-insoluble therapeutic agent are present at a weight ratio of between 1 to 40 and 500 to 1 gallate containing compound to water-insoluble therapeutic agent. In other embodiments, the gallate containing compound is epi gallo catechin gallate (EGCG), tannic acid or epi catechin gallate.

Another aspect of the present disclosure relates to a medical device having a surface including a coating containing such a composition and/or having the composition incorporated into at least part of the structure of the device. In one embodiment, the coating is free of an additional polymer or non-polymer carrier modifying a rate of release of the therapeutic agent from the device upon implantation in the body of a patient.

In certain embodiments, the implantable medical device is an expandable device. In other embodiments, the device is a vascular stent, a ureteral stent, a catheter, a balloon, a balloon catheter, an embolic device, a stent graft, a wire guide, or a cannula.

The water-insoluble therapeutic agent can be, for example, an immunosuppressive agent, an antiproliferative agent, a microtubule stabilizing agent, a restenosis-inhibiting agent, an inhibitor of the mammalian target of rapamycin, an analgesic, or an anesthetic. In certain embodiments, the water-insoluble therapeutic agent is a taxane compound, for example, paclitaxel. In other embodiments, the water-insoluble therapeutic agent is an analgesic and/or an anesthetic agent, for example lidocaine.

Another aspect of the present disclosure relates to a method for delivering a therapeutically effective amount of a water-insoluble therapeutic agent locally to the tissue of a patient. In certain embodiments the method includes contacting a vessel wall of the patient with a medical device as provided by the present invention and maintaining the device in contact with the vessel wall for a time sufficient to deliver the water-insoluble therapeutic agent to the tissue of the patient.

In other embodiments, the method includes applying to a patient's skin a topical drug preparation comprising a gallate containing compound and a water-insoluble therapeutic agent in a suitable dosage form for dermal delivery of the agent to the patient. Suitable forms include, but are not limited to, sprays, foams, gels, pastes, ointments, creams, lotions and tinctures. In some embodiments, liquid or semi solid forms of the drug preparation may be preformulated and then included within a medical dressing. In some embodiments, the preparation may be nonaqueous. In some embodiments, solid or semi-solid dosage forms of the drug preparation may comprise dried combinations of gallate containing compounds and water-insoluble drugs in the form of a film or pellet, which may be placed on the patient's skin in an area to be treated. In some embodiments, the drug preparation may be cast as a film or premade in the form of microspheres, and/or may comprise polymers or polymeric hydrogel carrier materials such as, but not limited to, polylactic co glycolic acid, polymethyl methacrylate, polyvinyl alcohol, hyaluronic acid, alginate or celluloses.

In other embodiments, the method includes injecting or extruding a pharmaceutical preparation comprising a gallate containing compound and a water-insoluble therapeutic agent at an area of the patient to be treated. The preparation may be applied to the patient by injection or extrusion into the patient's body, or outside of the patient's body (e.g., to treat an exterior wound). The preparation is preferably formulated as a viscous liquid or semi solid, and in some embodiments may be formulated as a nonaqueous paste. The preparation is preferably formulated to controllably release of the therapeutic agent into the patient at the area to be treated. The preparation is formulated to controllably release the agent over a period of time. In some embodiments, the preparation is formulated to controllably release the agent over a period of at least two days, at least seven days, or at least two weeks. In some embodiments, the preparation may comprise a viscous polymeric liquid such as, but not limited to, polypropylene glycol, polyethylene glycol, glycerol, labrasol, transcutol, tween or pluronic. In some embodiments, the preparation may comprise a eutectic mixture. Examples of suitable eutectic mixtures include, but are not limited to, eutectic mixtures of ibuprofen and menthol, and eutectic mixtures of lidocaine and menthol.

In some embodiments, dermal or injectable preparations for use in the methods described above may include additional excipients commonly known to pharmaceutical scientists.

Another aspect of the present disclosure provides a method for treating a patient suffering from a disease or condition. One embodiment of the method includes implanting a medical device provided by the present invention in a vessel of a patient for a time sufficient to deliver a therapeutically effective amount of the water-insoluble therapeutic agent to a tissue of the patient. Another embodiment of this method includes the delivery of a solution of a water-insoluble therapeutic agent and a gallate containing compound by or in association with a medical device.

BRIEF DESCRIPTION OF THE DRAWINGS

FIG. 1(A) shows the effect of storage temperature on the solubility for solutions including EGCG. FIG. 1(B) shows the effect of storage temperature on the solubility of solutions including Tannic Acid. FIG. 1(C) shows the variation in amphotericin solubility with pH.

FIGS. 4(A)-(D) are graphs showing the solubility and stability of docetaxel in a solution of EGCG (FIG. 4(A) and FIG. 4(C)) or tannic acid (FIG. 4(B) and FIG. 4(D)) at various times and temperatures.

FIG. 5 is a bar chart showing the uptake into and across a monolayer of mdck cells for docetaxel combined with solubilization agents tween, diblock copolymer or EGCG.

FIG. 6 is a bar chart showing the update into and across a monolayer of Caco2 cells for curcumin as a micelle or after with EGCG as a solubilization agent. The chart illustrates apical to basolateral transport (transcellular) and accumulation (intracellular) of curcumin in caco2 cells incubated with either micellar (diblock polymer) or EGCG solutions of the drug at 250 micrograms/ml.

FIG. 7 is a graph showing the effect of diblock copolymer of the release of paclitaxel from EGCG coated balloon catheters. Balloons are coated with 30 mg of EGCG and 300 micrograms of paclitaxel. Percentage release into PBS at 37 C is measured by HPLC FIG. 8 is a bar chart showing the transfer of paclitaxel to a rat aorta from an EGCG-coated balloon catheter.

FIG. 9 is a bar chart showing the effect of ultrasound on the transfer of paclitaxel to the aorta from an EGCG coated catheter.

FIG. 10 is a bar chart showing the transfer of paclitaxel into an artery using a diblock copolymer coating.

FIG. 11 is a bar chart showing the transfer of paclitaxel into an artery from a tannic acid-coated balloon catheter.

FIG. 12 is a bar chart showing the uptake of docetaxel into huvec cells and the effect of ultrasound.

FIG. 13 is a bar chart showing the uptake and transfer of amphotericin B in Caco2 cells.

FIG. 14 is an illustration show a reaction scheme for the manufacture of PAMAM dendrimer-crosslinked gallic acid compounds.

FIG. 15 is a bar chart showing the solubility of drugs in tannic acid or EGCG coatings.

DETAILED DESCRIPTION OF THE PREFERRED EMBODIMENTS

Figure 1A:
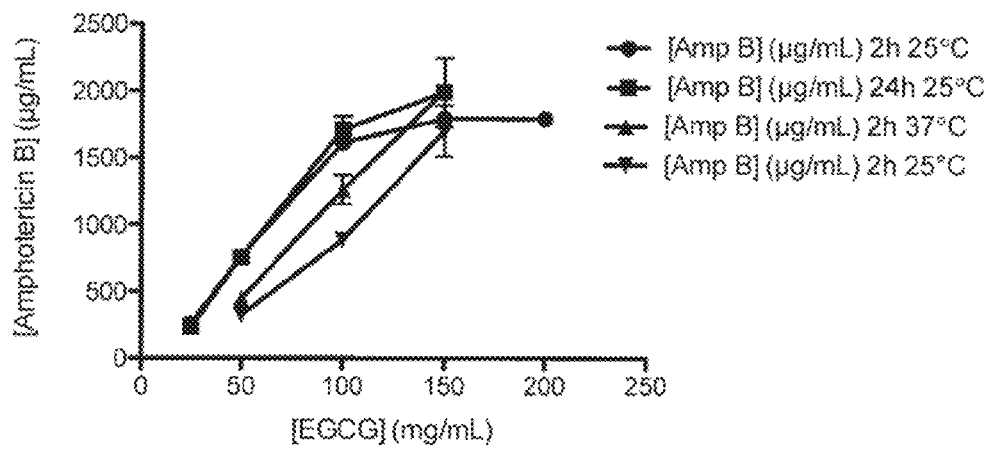
FIGS. 1(A)-(C) are graphs showing the solubility of amphotericin as a function of EGCG or Tannic acid concentration.

For the purpose of promoting an understanding of the principles of the invention, reference will now be made to embodiments, some of which are illustrated in the drawings, and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

In the discussions that follow, a number of potential features or selections of the water-insoluble therapeutic agent, gallate containing compound, implantable medical device structure, or other aspects, are disclosed. It is to be understood that each such disclosed feature or features can be combined with the generalized features discussed herein, to form a disclosed embodiment of the present invention.

Definitions

The term "therapeutic effect" as used herein means an effect which induces, ameliorates or otherwise causes an improvement in the pathological symptoms, disease progression or physiological conditions associated with or resistance to succumbing to a disorder, for example restenosis, of a human or veterinary patient. The term "therapeutically effective amount" as used with respect to a therapeutic agent means an amount of the therapeutic agent which imparts a therapeutic effect to the human or veterinary patient.

The term "water-insoluble" as applied to a therapeutic agent herein refers to a therapeutic agent having a solubility in water at 25° C. of less than 2 milligrams per milliliter (mg/ml). More preferably, the water-insoluble therapeutic agent has a solubility in water at 25° C. of less than 1 mg/ml, even more preferably less than 0.1 mg/ml, and in certain embodiments less than 10 micrograms per milliliter (µg/ml).

The term "pharmaceutically acceptable carrier" includes any and all solvents, dispersion media, coatings, antibacterial and antifungal agents, isotonic and absorption delaying agents, and the like, compatible with pharmaceutical administration. Preferred examples of such carriers or diluents include, but are not limited to, water, saline, dextrose solution, and 5% human serum albumin. Liposomes and non-aqueous vehicles such as fixed oils may also be used. Supplementary active compounds can also be incorporated into the compositions.

The term "solubilized" describes the condition in which a water-insoluble therapeutic agent, for example paclitaxel, is dissolved in a solvent, for example a matrix of gallate containing compound. "Solubilization" is the presence of the agent in a non-particulate form which is typically at the single molecule level. The solubilized agent can be present in a liquid solution such as in aqueous media or in an organic solvent. Alternatively, the solubilized agent is present in a non-particulate form in a solid or semi-solid matrix composed of another non liquid material. In some cases the solubilised agent may be present in the center of nanoparticles or micelles suspended in aqueous media.

"The term "eutectic" refers to a mixture of substances that either melts or solidifies at a single temperature that is lower than the melting points of the separate constituents.

Compositions

One aspect of the present invention relates to compositions including at least one water-insoluble therapeutic agent and at least one gallate containing compound. In certain embodiments, the composition includes an aqueous solvent, for example water or a pharmaceutically acceptable buffer. In these embodiments, the presence of the gallate containing compound results in an aqueous solution in which the water-insoluble therapeutic agent is dissolved in the aqueous solvent at a higher concentration that would be possible under the same conditions if the gallate containing compound was not present.

Another embodiment relates to compositions including at least one water-insoluble therapeutic agent solubilized within a matrix of at least one gallate containing compound. Such compositions, termed "solid solutions," do not include an aqueous solvent. Instead, the water-insoluble therapeutic agent is dissolved at a molecular level within a matrix of the gallate containing compound, which acts as a solvent. Yet another embodiment relates to compositions formed by the addition of an aqueous solvent to the solid solution. Such compositions can contain the water-insoluble therapeutic agent is dissolved in the aqueous solvent as well as a nanoparticulate form for the water-insoluble therapeutic agent.

In some embodiments, the gallate containing compound increases the solubility of the water-insoluble therapeutic agent when the composition is applied to an aqueous medium, for example when administered to a human or veterinary patient; enhances the delivery of the water-insoluble therapeutic agent to and/or across a vessel wall and into the tissue of the patient; and/or enhances the dermal uptake of the water-insoluble therapeutic agent when applied to a patient's skin. In yet other embodiments the gallate containing compound increases the cellular uptake of the water-insoluble therapeutic agent. In other embodiments the drug is partly or fully dissolved in the solid phase of the gallate containing compound so that in an aqueous environment, the drug is released from the formulation as the gallate containing compound dissolves.

The gallate containing compound may be a compound such as, but not limited to, epi gallo catechin gallate (EGCG) or tannic acid. Other preferred compounds include natural and synthetic compounds containing gallates. Yet other preferred compounds include compounds that contain the chemical moieties of gallate, catechin, tannin, or similar polyphenol moieties, including naturally derived compounds, as well as polymers that have been synthetically modified and covalently attached to these moieties.

In other embodiments, gallate containing compounds include, but are not limited, to the tannins, catechin gallates, the querglanins, galloyl arbutin, theaflavine gallate or digallate galloylbergenin, camelliatannin, theasinensin, procyanidingallate, galloylsilibin, trihydroxystillbene-4-6-galloyl-glocopyranoside, comuside. In certain embodiments, these compounds are characterized by high levels of H-bond donor and acceptor sites along with benzene or lactone ring structures. In other embodiments, gallate containing compounds include similar molecules to EGCG or tannins that do not specifically contain the trihydroxy benzoate group of the gallate but have very similar structures to the gallate Examples of such compounds include, but not limited to, the mangiferines, the quercetins, especially, quercetin 3 glucopyranoside, quercetin glucoside, quercetin galactoside, quercetin meritrin, hesperidin methylchalcone, isobutrin, hypolactin glucoside, rutin and procyanadin and proanthocyandin.

In certain embodiments, the weight ratio of gallate containing compound:water-insoluble therapeutic agent in the composition is in the range of 200:1 to 1:1 or 200:1 to 5:1 or 200:1 to 10:1 or 200:1 to 30:1 or 200:1 to 50:1 or 100:1 to 1:1 or 100:1 to 5:1 or 100:1 to 10:1, or 100:1 to 30:1 or 100:1 to 50:1 or 50:1 to 1:1 or 50:1 to 5:1 or 10:1 to 1:1 or 10:1 to 5:1 or 1:1 to 1:2 or 1:1 to 1:5 or 1:40 to 500:1 or 1:20 to 400:1 or 1:10 to 200:1 or 1:1 to 200:1 or 1:40 to 200:1 or 1:20 to 200:1 or 1:10 to 500:1. When more than one gallate containing compound is present, the above ranges can apply to the ratio of the weight of each individual gallate containing compound to weight of the water-insoluble therapeutic agent or to ratio of the total weight of the gallate containing compounds present to the weight of the water-soluble therapeutic agent. The weight ratio of gallate containing compound to water-insoluble drug is such that a solution of the water-insoluble therapeutic agent in the gallate containing compound is formed.

In other embodiments, the composition includes the gallate containing compound in an amount that increases the solubility of a water-insoluble therapeutic agent in the composition by 10, 20, 30, 40, 50, 75, 100, 125, 150, 200, 300 or 400 percentage in an aqueous medium compared to an otherwise identical composition that does not include the gallate containing compound.

In yet other embodiments, the composition includes the gallate containing compound a concentration of between 10 and 50, or 20 and 50, or 30 and 50, or 40 and 50 mg/ml and the water-insoluble therapeutic agent, for example paclitaxel or docetaxel, solubilized at a concentrations of at least 400, 500, 600, 700, 800, 900 or 1000 micrograms/ml.

In some embodiments, a composition for the treatment of a medical condition comprises a topical drug preparation comprising a gallate containing compound and a water-insoluble drug, where the gallate containing compound is present in an amount effective in increasing the dermal uptake of the drug. In some embodiments, the gallate containing compound is selected from the group consisting of epi gallo catechin gallate and tannic acid. In some embodiments, the drug is selected from paclitaxel, docetaxel, amphotericin, curcumin, retinoic acid, finasteride, and lidocaine. In some embodiments, the drug has a molecular weight greater than 500 Daltons. In some embodiments, the gallate containing compound is present in an amount by weight equal to or greater than the amount by weight of the water-insoluble drug. In some embodiments, the weight ratio of gallate containing compound:water-insoluble drug is in the range of 200:1 to 1:1, 200:1 to 5:1, 200:1 to 10:1, 200:1 to 30:1, 200:1 to 50:1, 100:1 to 1:1, 100:1 to 5:1, 100:1 to 10:1, 100:1 to 30:1, 100:1 to 50:1, 50:1 to 1:1, 50:1 to 5:1, 10:1 to 1:1, 10:1 to 5:1, 1:1 to 1:2, or 1:1 to 1:5.

Suitable topical drug preparation forms comprise creams, pastes, gels, ointments, and other suitable forms for topical application. In some embodiments, the topical preparation comprises a preblended solid or semi solid matrix of the gallate containing compound and the drug. In some embodiments, the composition further comprises a solubilizing excipient such as propylene glycol. In some embodiments, the topical preparation comprises a eutectic solution, for example a eutectic solution of lidocaine and menthol, or a eutectic solution of ibuprofen and menthol. In some embodiments, the topical drug preparation is a dry, or nonaqueous preparation. In some embodiments, the gallate containing compound and the drug are predispersed in one of a membrane, a hydrogel, an electrospun film, or a skin dressing.

In certain embodiments, a composition for the treatment of a medical condition comprises a nonaqueous pharmaceutical preparation comprising a gallate containing compound and a water-insoluble drug, where the preparation is formulated to form a partially water-insoluble mass when placed in an aqueous medium, that gradually releases the drug into the aqueous medium in a controlled manner. Such preparations may be useful, for example, in methods involving local delivery of a drug within a patient's body, or on an exterior wound of a patient's body. In some embodiments, the gallate containing compound is selected from the group consisting of epi gallo catechin gallate and tannic acid. In some embodiments, the drug is selected from paclitaxel, docetaxel, amphotericin, curcumin, retinoic acid, finasteride, and lidocaine. In some embodiments, the composition further comprises a solubilizing excipient, for example an excipient selected from the group consisting of glycerol, pluronic, propylene glycol, and polyethylene glycol.

In some embodiments, the preparation is formulated to release the drug into the aqueous medium over a period of at least two days, over a period of at least seven days, or over a period of at least two weeks. In some embodiments, the gallate containing compound is present in an amount effective in increasing the solubility of the water-insoluble drug in an aqueous medium. In some embodiments, the gallate containing compound is present in an amount by weight equal to or greater than the amount by weight of the water-insoluble drug. In some embodiments, the preparation is formulated as a viscous liquid or semi solid, and in some embodiments may be formulated as a paste.

Water-insoluble therapeutic agents within the scope of the present embodiments include water-insoluble antiproliferative agents immunosuppressive agents, restenosis-inhibiting agents, anti-cancer agents, analgesics/antipyretics, anesthetics, antiasthmatics, antibiotics, antidepressants, antidiabetics, antifungal agents, antihypertensive agents, anti-inflammatories, antineoplastics, antianxiety agents, sedatives/hypnotics, antianginal agents, nitrates, antipsychotic agents, antimanic agents, antiarrhythmics, antiarthritic agents, antigout agents, thrombolytic agents, hemorheologic agents, anticonvulsants, antihistamines, agents useful for calcium regulation, antibacterial agents, antiviral agents, antimicrobials, anti-infectives, bronchodilators, steroids and hormones.

Non-limiting examples of such water-insoluble therapeutic agents include lidocaine, prilocaine, finasteride, dutasteride, enzalutamide, bicalutamide, abiraterone, tamsulosin, sildenafil-base, tadalafil, doxorubicin, camptothecin, etoposide, mitoxantrone, cyclosporine, epothilones, napthoquinones, paclitaxel, docetaxel, carbitaxel, retinoic acid, limus based drugs (e.g. rapamycin, sirolimus), methotrexate, vincristine, vinblastine, gemcitabine, statins (for example atorvastatin, fluvastatin, lovastatin, pitavastatin, pravastatin, rosuvastatin and simvastatin), steroids (for example cortisteroids, prednisilone and dexamethazone), mitomycin, amphotericin, curcumin and derivatives or analogues of these agents.

Preferred water-insoluble therapeutic agents include water-insoluble antiproliferative agents, immunosuppressive agents, restenosis-inhibiting agents. In particular embodiments antiproliferative agents or immunosuppressive agents that are restenosis-inhibiting agents are utilized, which can be effective to inhibit restenosis of a vessel when applied to the inner wall of the vessel. In this regard, "restenosis-inhibiting" includes preventing or reducing the extent of restenosis. The inhibition of restenosis may be observed after a procedure in which the vessel wall is injured due to dilatation, for example during dilatation with a balloon of a balloon catheter and/or by expansion of a stent.

The water-insoluble restenosis-inhibiting agent may be a microtubule stabilizing agent such as paclitaxel, docetaxel, a paclitaxel analog, or a paclitaxel derivative or other taxane compound; a macrolide immunosuppressive agent such as sirolimus (rapamycin), pimecrolimus, tacrolimus, everolimus, zotarolimus, novolimus, myolimus, temsirolimus, deforolimus, or biolimus; an antiproliferative agent; a smooth muscle cell inhibitor; an inhibitor of the mammalian target of rapamycin (mTOR inhibitor); or a mixture of two, or two or more of any of these. These or other water-insoluble restenosis-inhibiting agents, including each agent or agent type identified herein, more preferably have a solubility in water at 25° C. of less than 1 mg/ml, even more preferably less than 0.1 mg/ml, and in certain embodiments less than 10 micrograms/ml. Paclitaxel, docetaxel, sirolimus, pimecrolimus, tacrolimus, everolimus, zotarolimus, novolimus, myolimus, temsirolimus, deforolimus, and biolimus are preferred water-insoluble restenosis-inhibiting agents for use herein (each known to have a water solubility of less than about 10 micrograms/ml).

The compositions of the present invention include those that may be administered by oral, parenteral (e.g., intramuscular, intraperitoneal, intravenous, ICV, transcatheter arterial chemoembolization, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

Another embodiment of the present invention provides a composition, including the one or more water-insoluble therapeutic agent(s) solubilized in a matrix of one or more gallate containing compound(s), where the composition is encapsulated in microparticles, for example, polymeric microparticles. The microparticles can be biodegradable or nonbiodegradable microparticles. Such microparticles can be delivered to a patient by the delivery means listed above and allow for the delivery of the water-insoluble therapeutic agent(s) by elution from the microparticles or as a result of biodegradation of the microparticles.

Nonbiodegradable polymers that can be used to prepare such microparticles include, but are not limited to, cellulose acetate, cellulose nitrate, silicone, polyethylene terephthalate, polyurethane, polyamide, polyester (e.g. Nylon), polyorthoester, polyanhydride, polyether sulfone, polycarbonate, polypropylene, high molecular weight polyethylene, and polytetrafluoroethylene, or mixtures of these. Biodegradable polymers that can be used include, but are not limited to polylactic acid (PLA), polyglycolic acid (PGA), poly(lactic-co-glycolic acid) (PLGA), polyanhydride, polycaprolactone, polyhydroxybutyrate valerate, or mixtures of these.

In certain embodiments, the compositions containing the water-insoluble therapeutic agent and the gallate containing compound are free, or "substantially free", of another compound, such as an emulsifier, oil, triglyceride matrix, lipid or other solubilizing agent or carrier, in which the water-insoluble therapeutic agent exhibits increased solubility. As applied to the present embodiments, the compositions are considered to be substantially free of such compounds as long as the additional compounds do not alter the solubility of the water-insoluble therapeutic agent by more than 1 percentage. In other embodiments, the additional compounds do not alter the solubility of the water-insoluble therapeutic agent by more than 10, 5 or 2 percentage.

Medical Devices

Other aspects of the present disclosure relate to medical devices incorporating a releasable component including at least one water-insoluble therapeutic agent solubilized within a matrix of at least one gallate containing compound, and to methods for the preparation and use of such medical devices. In certain embodiments, the medical devices are coated with or otherwise contain the compositions as disclosed above.

In one embodiment, the medical device may be any of a wide variety of devices having an implantable medical device structure sized and shaped for temporary or permanent implantation in a human or veterinary patient. Medical devices having structures implantable in a bodily passage will often be used. The bodily passage may for example be a passage of the alimentary system, the urogenital system, the biliary system, or the cardiovascular system. Medical devices including a device structure implantable in the cardiovascular system are preferred, including for example those implantable in a vessel or chamber of the cardiovascular system of a human or veterinary patient through which blood travels. The passage may for example be a tubular passage such as an artery or vein, or may be a larger chamber such as a ventricle or atrium of the heart. Implantable medical devices that include structures that span or bridge between cardiovascular or other bodily passages are also contemplated. The implantable medical device can be adapted to be entirely or only partially implanted in a cardiovascular passage or other bodily passage. Other embodiments cover the use of gallate containing compounds and water-insoluble drug solutions or suspensions with other medical devices such as, but not limited to, tumor resection tools, surgical operation instruments, specialized injection devices, access catheters, robotic surgical systems.

The releasable component may be incorporated into the structure of the medical device and/or be present in a coating on one or more surface of the device. By way of example, the medical device can be or include a catheter, a wire guide, a stent, a coil, a needle, a graft, a filter, a balloon, a cutting balloon, a scoring balloon, a weeping (perfusion) balloon, or any combination of these. In other embodiments the device is a solid or semi-solid material that releases the water-insoluble drug and gallate containing compounds locally as a drug solution or suspension. Such devices include, but are not limited to, polymeric materials as films, pastes, micro and nanoparticles.

In some preferred embodiments herein, the implantable medical device will be or include a balloon catheter, such as an angioplasty balloon catheter, a weeping or infusion balloon, a scoring balloon catheter or a cutting balloon catheter.

In other embodiments herein, the implantable medical device will be or include a stent. Such a stent may for example be a force-expandable stent, such as a balloon-expandable stent, or a self-expanding stent. The stent may be made from any one of numerous metals and alloys, including those identified hereinabove. The structure of the stent may be formed in a variety of ways to provide a suitable intraluminal support structure having an outer surface for contact with the vessel wall upon implantation and an inner surface that faces the lumen of the vessel and that can be generally opposite the outer surface. For example, the stent may be made from a woven wire structure, a laser-cut cannula, individual interconnected rings, or another pattern or design. In these or other constructions, the stent can include a plurality of struts each having an outer surface for contact with the vessel wall and an inner surface for facing the lumen of the vessel.

In certain embodiments the stent may be configured in the form of one or more self-expanding "Z-stents" or Gianturco stents, each of which may comprise a series of substantially straight segments interconnected by a series of bent segments. The bent segments may comprise acute bends or apices. The Gianturco stents are arranged in a zigzag configuration in which the straight segments are set at angles relative to each other and are connected by the bent segments. In other embodiments, the stent may be formed from a slotted tube generally comprising a series of longitudinally-adjacent segments and a patter of connecting segments disposed there between. Such stents may be force-expandable, such as balloon-expandable, or self-expanding, as discussed above. Self-expanding stents of this type can be made of a resilient metal, preferably a superelastic metal alloy such as a superelastic nickel-titanium (Ni—Ti) alloy, as occurs for example in the ZILVER® nitinol stent commercially available from Cook Medical.

Any stent discussed above or elsewhere herein can have a stent surface carrying the releasable component as discussed herein, either as the sole coating carried by the stent surface, or in combination with one or more additional coatings positioned underneath and/or overtop the layer containing the releasable component. As well, surfaces of the stent not carrying the releasable component may optionally be bare (uncoated), or may carry one or more different coatings. Additionally, where the stent is mounted on a balloon of a balloon catheter for delivery, the surface of the balloon may carry the releasable component and potentially other layer(s) as described herein, and/or the surface of the stent may carry the releasable component and potentially other layer(s) as described herein. The practice of these and other variants will be within the purview of those of ordinary skill in the art in view of the teachings herein.

Another device structure of interest is a covered stent, such as the stents described in U.S. Pat. No. 8,192,479 and in U.S. Patent Publication Number US20100168837, the contents of both of which are incorporated by reference. Such devices allow for delivery of a bioactive from a surface in contact the vessel wall while maintaining downstream perfusion.

When the compositions are present in a coating on a surface of the device, the composition may constitute greater than 50, 75, 90, 95 or 99 percentage by weight of the coating. In certain embodiments, the coatings include less than about 5, 2, 1, 0.5, 0.1, 0.05 or 0.01 percentage by weight of materials other than the water-insoluble therapeutic agent and the gallate containing compound. In other embodiments, the coatings include less than about 5, 2, 1, 0.5, 0.1, 0.05 or 0.01 percentage by weight of materials, such as polymers or other non-polymer carriers, that alter the release rate of the water-insoluble therapeutic agent.

Preferred water-insoluble therapeutic agents used in conjunction with medical devices include water-insoluble anti-proliferative agents, immunosuppressive agents, and restenosis-inhibiting agents. Particularly preferred are water-insoluble restenosis-inhibiting agents, such as those described above. In certain preferred embodiments, paclitaxel is the only therapeutic agent included in combination with the device.

The water-insoluble therapeutic agent can be incorporated in the device at any suitable level. Typically, when coated onto a device such as a stent or a balloon, the water-insoluble therapeutic agent will be incorporated at a level of 0.001 to 1000 micrograms per $mm^2$, or 0.01 to 1000 micrograms per $mm^2$, or 0.1 to 1000 micrograms per $mm^2$, or 0.1 to 100 micrograms per $mm^2$, and in certain preferred forms 0.1 to 10 micrograms per $mm^2$ or 0.5 micrograms per $mm^2$ to 3 micrograms per $mm^2$, or in the range of 0.5 micrograms per $mm^2$ to 2 micrograms per $mm^2$ of the coated surface. Where two or more therapeutic agents are included in the coating, the above-recited levels can apply to the combined weight of all the therapeutic agent(s), or to the therapeutic agents individually. It will also be understood that the coating may contain variations in the level of therapeutic agent in different regions of the coating either due to manufacturing variances or intentional design criteria. Thus, the present invention contemplates coatings in which the level of therapeutic agent(s) is substantially uniform over the entire area covered by the coating, or in which the level of therapeutic agent(s) differs substantially in one area of the coating as compared to another area covered by another area of the coating. In certain preferred embodiments, paclitaxel is incorporated at a level in the range of 1 microgram per $mm^2$ to 10 micrograms per $mm^2$, or in the range of 2 micrograms per $mm^2$ to 6 micrograms per $mm^2$, or in the range of 0.5 micrograms per $mm^2$ to 3 micrograms per $mm^2$, or in the range of 0.5 micrograms per $mm^2$ to 2 micrograms per $mm^2$ either as the only therapeutic agent in the coating or in combination with one or more additional therapeutic agents. In particularly beneficial implantable medical devices of the invention, such paclitaxel-containing coatings are carried on a surface of a stent, including for example any stent described herein, and/or on a surface of a balloon of a balloon catheter, including for example any balloon catheter described herein.

The water-insoluble therapeutic agent will typically be incorporated in the device in a therapeutically effective amount. In this regard, it will be understood that where the therapeutic agent is a restenosis-inhibiting agent, the restonosis-inhibiting agent will be incorporated in the coating in an amount that is effective to inhibit restenosis when the implantable medical device (e.g. a balloon or stent) is deployed so as to deliver the therapeutic agent from the implantable medical device to a wall of the artery, vein or other vessel or passage that is being treated by the device. As will be recognized, the level of a therapeutic agent that will be therapeutically effective will vary in accordance with the particular therapeutic agent in use, the implantable medical device in use, the implant site, the condition to be treated, the composition of the coating including the therapeutic agent, and other potential factors. Through routine experimentation in view of the disclosures herein the achievement of a therapeutically effective amount of the water-insoluble therapeutic agent will be within the purview of those ordinarily skilled in the field.

The gallate containing compound(s) is included in the device in an amount effective to form a matrix of gallate containing compound(s) containing solubilized water-insoluble therapeutic agent. In certain embodiments, the weight ratio of gallate containing compound(s) to the water-insoluble therapeutic agent in the device is in the range of 200:1 to 10:1 or 200:1 to 30:1 or 200:1 to 50:1 or 100:1 to 10:1, or 100:1 to 30:1 or 100:1 to 50:1 or 1:40 to 500:1 or 1:20 to 400:1 or 1:10 to 200:1 or 1:1 to 200:1 or 1:40 to 200:1 or 1:20 to 200:1 or 1:10 to 500:1. When more than one gallate containing compound is present, the above ranges can apply to ratio of the weight of each individual gallate containing compound to weight of the water-insoluble therapeutic agent or to ratio of the total weight of the gallate containing compounds present to the weight of the water-soluble therapeutic agent.

In embodiments in which the releasable component is contained within or in a layer coating the implantable medical device, the gallate containing compound(s) are observed to increase the amount of water-insoluble therapeutic agent released when implanted, by 10, 20, 30, 40, 50 75, 100, 125, 150, 200, 300 or 400 percentage as compared to a device that is identical except for the absence of the gallate containing compound(s).

In certain other embodiments, the gallate containing compound(s) are observed to increase the delivery of the water-insoluble therapeutic agent across a vessel wall and into the tissue of the patient. The increase in the amount of the water-insoluble therapeutic agent delivered to the tissue of the patient from a device including the gallate containing compound(s) may depend upon a number of factors, such as the nature of the vessel in which the composition is placed or device is implanted, as well as the environment within the vessel and the construction of the implantable device.

However, the increase in the amount water-insoluble therapeutic agent delivered through a vessel wall may be characterized in an ex vivo assay in which the implantable device is placed in a section of the appropriate vessel and incubated in a buffer solution for a fixed time. In one such assay, a device, for example, is placed in a section of porcine ureter, which is hydrated in a Phosphate Buffered Saline buffer. The ureter is incubated in a closed container for a fixed time, for example 5 minutes at 37 deg. C. After the incubation period, the water-insoluble therapeutic agent present in the ureter tissue is extracted using an extraction solution, such as an enzyme solution, organic solvent, organic/aqueous mixture, or acidified mixture. The extraction solution used is dependent on the water-insoluble therapeutic agent being extracted. The amount of water-insoluble therapeutic agent present in the ureter and in the device is determined using, for example, an appropriate HPLC method.

In certain embodiments, the claimed devices include gallate containing compound(s) sufficient to increase the amount of water-insoluble therapeutic agent delivered, as measured by this assay, by at least 5%, 10%, 15%, 20%, 25%, 30%, 40%, 50%, 70%, 100%, 150% or 200% compared to the amount of water-insoluble therapeutic agent delivered, under the same conditions, from an otherwise identical device that does not include the gallate containing compound(s). In other embodiments, the devices include gallate containing compound(s) sufficient to increase the amount of water-insoluble therapeutic agent delivered, as measured by this assay, within a period of 1, 5, 15, 30, 60, 120, 300, 500 or 1000 minutes by at least 5%, 10%, 15%, 20%, 25%, 30%, 40%, 50%, 70%, 100%, 150% or 200%. In yet other embodiments, the claimed devices include an amount of gallate containing compound(s) sufficient to increase the amount of water-insoluble therapeutic agent delivered, as measured by this assay, within a period of 1, 5, 15, 30, 60 or 120 days by at least 5%, 10%, 15%, 20%, 25%, 30%, 40%, 50%, 70%, 100%, 150% or 200%.

In certain embodiments, the gallate containing compound(s) is effective to deliver a therapeutically effective amount of the water-insoluble therapeutic agent to patient tissue in a time period of about 5 minutes or less after implantation of the implantable medical device. More preferably, such time period is about 3 minutes or less, even more preferably about 2 minutes or less, and most preferably about 1 minute or less, e.g. in the range of about 20 seconds to about 1 minute. Such embodiments configured for relatively rapid delivery are especially beneficial when the releasable component is carried by a surface of a temporarily implantable medical device structure, for example a balloon of a balloon catheter, including any balloon catheter and in any coating arrangement described herein.

In those embodiments in which the releasable component is contained as a coating layer, any of a wide variety of coating patterns may be used to constitute a material coat on the medical device. The coating layer can be directly adhered to a surface of an implantable structure of the medical device and provide an outermost surface over the implantable structure, and/or to constitute the entirety of the overall material coat on the implantable structure. In other embodiments, an overall material coat adhered to the implantable structure of the medical device can include one or more different coatings positioned underneath the layer including the releasable component (e.g. as in a polymeric or other primer coating, or a different therapeutic agent coating, adhered directly to the surface of the medical device), one or more different coatings positioned overtop the layer including the releasable component (e.g. as in a polymeric or other protective or diffusion barrier coating), or both. As well, there may be one or more different coatings adjacent the layer including the releasable component, and/or multiple layers including the releasable component may be carried by the implantable medical device at locations discrete from one another. The layer including the releasable component may be present in an aperture(s) such as a well(s), groove(s) or hole(s) defined in the implantable medical device (e.g. in a stent) or may partially coat or completely coat the implantable medical device or a given surface (e.g. inner, outer or side surface) of the implantable medical device. These and other overall device coating arrangements can be utilized.

The layer including the releasable component can be carried by any suitable surface of the implantable medical device structure. The layer including the releasable component can be carried by, and in some embodiments only by, a surface or surfaces of the implantable medical device configured for contact with patient tissue when the device is implanted. For example, in some embodiments the layer including the releasable component is carried by a surface of a balloon of a balloon catheter, or by a surface of a stent, which is configured for contact with a wall of a vessel when the balloon is implanted (usually temporarily) or when the stent is implanted (usually permanently). In particular embodiments, in the case of a balloon of a balloon catheter which inflates to provide a substantially cylindrical outer surface as discussed above, the layer including the releasable component is carried by such substantially cylindrical outer surface, either partially or completely covering the substantially cylindrical surface. In the case of a stent having an outer surface as discussed above, the layer including the releasable component can be carried by the outer surface, either partially or completely covering the outer surface.

The layer including the releasable component and any other coating layers present can be incorporated as a part of the implantable medical device by dipping the uncoated device into a solution containing a solvent, the water-insoluble therapeutic agent and the gallate containing compound. The solvent is then removed, for example by evaporation, leaving a coating of the water-insoluble therapeutic compound in a matrix of the gallate containing compound. The layer including the releasable component can be constituted entirely of the water-insoluble therapeutic agent and gallate containing compound(s), or may, for example, include a biostable polymer, where the polymer remains attached to the device structure as releasable component is released. Alternatively, or in addition to the biostable polymer, this layer may include a bioabsorbable polymer. Such a polymer layer can include a polymeric matrix, e.g. made using a suitable polymer as identified herein, and in certain forms will be a porous layer that releasably contains an admixture including the water-insoluble therapeutic agent and gallate containing compound(s) in the pores thereof.

In other embodiments, the releasable component can be incorporated into microspheres, for example, biostable or biodegradable microspheres. Such microspheres can be suspended in a fluid or may be coated onto the surface, or contained within, an implantable device.

In certain aspects, a coated medical device as described herein, preferably comprising a stent and/or balloon catheter carrying the releasable component, can be configured to, and used to, treat any suitable body passage in a manner including release of the water-insoluble therapeutic agent to the wall tissue of the body passage. The body passage may for example be a vein, artery, biliary duct, ureteral vessel, body passage or portion of the alimentary canal. A coated medical device as described herein may be used to treat a coronary artery, carotid artery, or a peripheral artery or vein, including as examples a renal artery or vein, iliac artery or vein, femoral artery or vein, popliteal artery or vein, subclavian artery or vein, intercranial artery or vein, aorta, vena cava, or others. In preferred embodiments, the coated medical devices will treat or prevent stenosis or restenosis in a body passage such as any of those identified herein, although treatment of other conditions is contemplated for other embodiments of the invention. In certain embodiments, the coated medical device is configured and used to treat a narrowing of a peripheral artery or vein.

In another embodiment, the gallate containing compound, for example EGCG or tannic acid, is encapsulated in polymeric materials along with a hydrophobic drug so as to allow for enhanced drug release properties. Such technology also allows for the enhanced uptake of the drug at a preferred implantation site. The gallate containing compound can be incorporated into polymeric microspheres along with taxanes like paclitaxel or docetaxel and a controlled release of the EGCG was observed.

In one embodiment, polymeric microspheres containing the gallate containing compound and drugs such as paclitaxel or docetaxel are injected into the body where a slower release of drug is preferred. For example the microspheres can be injected locally to treat diseases such as rheumatoid arthritis or uterine fibroids. In embolic treatments, the microparticles can block blood supply and an EGCG or tannic acid stimulated release of paclitaxel or docetaxel can provide for a strong antiproliferative therapy (chemoembolism). Polymeric blends can include hydrophobic polymers such as polylactic acid, polyglycolic acid or polycaprolactone, polyanhydrides or copolymers (e.g. PLGA). The gallate containing compound can also be incorporated into hydrophilic polymers such as chitosan, polyvinyl alcohol, alginate and hyaluronic acid.

In another embodiment, the coencapsulation of the hydrophobic drug and the gallate containing compound in the polymeric matrix accelerate the release of the drug. In other embodiments, polymer-gallate containing compound-drug combinations are coated onto an implant for localized application.

In yet further embodiments, drugs that are poorly taken up by the gut (due to reasons such as low solubility, or because they are substrates of drug efflux proteins in the gut) are rendered orally available by using formulations of the gallate containing compound and the drugs. For example, EGCG is stable in acid solutions and unaffected by the acid environment of the stomach. In one such embodiment, EGCG enhances the uptake of drugs into gut cells and allows the drugs to pass through the cells into the blood stream before drug efflux proteins can interact with the compounds to efflux them back into the gut.

In another embodiment, gallate containing compound-drug solutions are injected directly into the body to allow for preferred localization of the drug at a required site of action. Once at the site, enhanced tissue accumulation of the drug can also occur. For example docetaxel and EGCG (or tannic acid) solutions may be infused or injected into the bladder, synovial joint, eye, tumor, brain, subcutaneous to treat cancer, arthritis, angiogenic disease such as retinopathy or psoriasis or neurological disease such as multiple sclerosis. These applications are supported by observations that EGCG and tannic acid increase the uptake of drugs, for example taxanes, into cells and tissues such as the bladder and into tumor cells. Alternatively, an amphotericin and EGCG solution might be injected directly into a fungal mass in the lung. Alternatively the solutions may be injected into the blood stream of peritoneal cavity for systemic delivery of the drug.

In yet other embodiments, creams, pastes, or gels containing gallate containing compound(s) and hydrophobic drug(s) are placed on the skin to allow for transdermal delivery of the drugs. For example the drug amphotericin might be applied this way to treat either fungal infections or leishmaniasis. The skin application of such formulation may be augmented by a systemic or oral formulation of the hydrophobic drug (e.g. amphoterecin) with a gallate containing compound.

In other embodiments, neurotoxic drugs are used on gallate containing compound-coated catheters so that upon insertion in the renal artery the catheter releases the drugs into and then through the artery wall. Applied drugs can include taxanes, vinca alkaloids, platinum based drugs, rapamycin based drugs as well as other drugs known to be neurotoxic.

In another embodiment, the coated catheters are used along with radio frequency ablation fixtures and are inserted into the renal artery to ablate the nerves around that artery. Other techniques such as HIFU or cryotherapy may be used for the same purpose. In yet another embodiment, microneedle laden catheters are used to inject compositions containing neurotoxin drugs and gallate containing compound(s) through the renal artery wall. Such coated catheter systems can be used to deliver substantial levels of neurotoxic drugs to blood vessels and to allow the transfer of drug through the vessel wall into the surrounding space containing nerve bundles.

The following examples illustrate the present invention. The examples and embodiments described herein are for illustrative purposes only and modifications or changes in light thereof will be suggested to one skilled in the art without departing from the scope of the present invention.

EXAMPLES

Example 1. Solubility of Amphotericin as a Function of EGCG or Tannic Acid Concentration, Effect of Temperature, pH and Stability at 24 Hours Amphotericin and either EGCG or tannic acid were dried down from acetonitrile (EGCG) or methanol (tannic acid)

solutions at various drug to EGCG or tannic acid ratios. PBS (EGCG) or water (tannic acid) was added and the final solution filtered through a 0.22 micron filter to remove any particulates. The solutions were analyzed for drug concentration using HPLC.

Figure 1B:
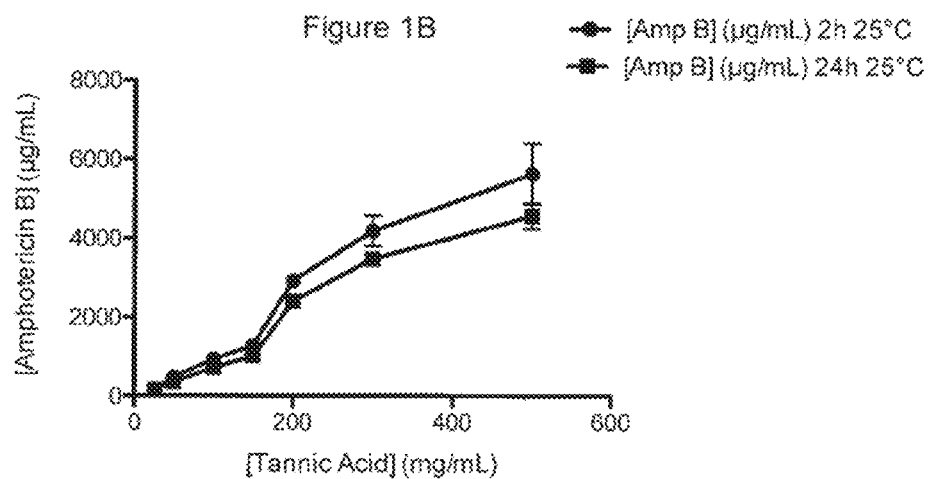
Figure 1C:
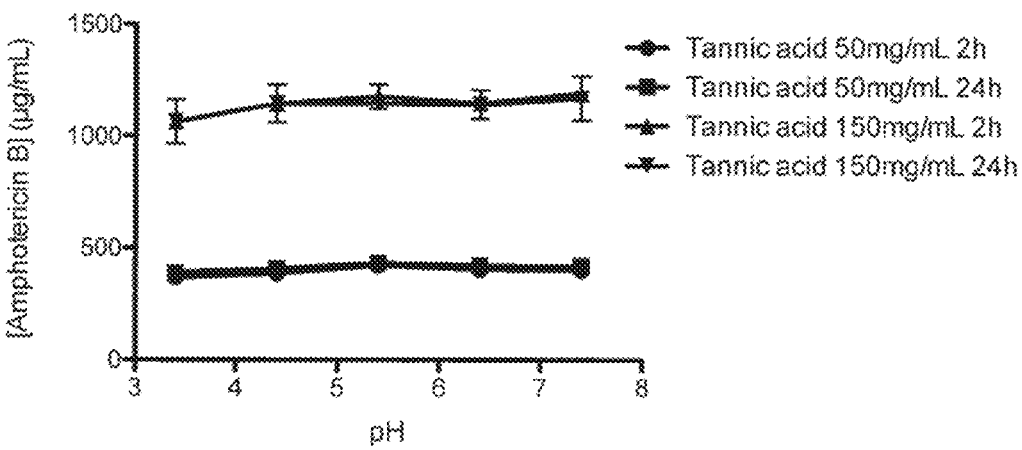

EGCG solubilised amphotericin up to a maximum concentration of 200 mg per ml EGCG with amphotericin at approximately 1800 microgram per ml. The solutions were stable for 24 hours (FIG. 1a). Tannic acid solubilised amphotericin up to a maximum concentration of 500 mg per ml Tannic acid with amphotericin at approximately 5700 microgram/ml. Solutions were stable for 24 hours (FIG. 1(b)). There was some effect of temperature on solubility levels with a small reduction at 100 and 200 mg/ml and a large reduction at 500 mg/ml for both 37° C. and 50° C. compared to 23° C. There was no effect of pH on amphotericin solubility in Tannic acid solutions (FIG. 1(c)).

The free solubility of amphotericin is approximately 1-10 micrograms/ml in water. However, the presence of EGCG or tannic acid significantly increases the solubility of amphotericin.

Example 2. Solubility of Curcumin as a Function of EGCG or Tannic Acid Concentration, Effect of Temperature and 24 Hour Stability of Solutions Curcumin and EGCG or tannic acid were dried down from acetonitrile (EGCG) or methanol (tannic acid) solutions at various drug to EGCG or tannic acid ratios. PBS (EGCG) or water (tannic acid) was added and the final solution filtered through a 0.22 micron filter to remove particulates. The solution was then analyzed for drug concentration using absorbance spectroscopy at 450 nm.

Figure 2A:
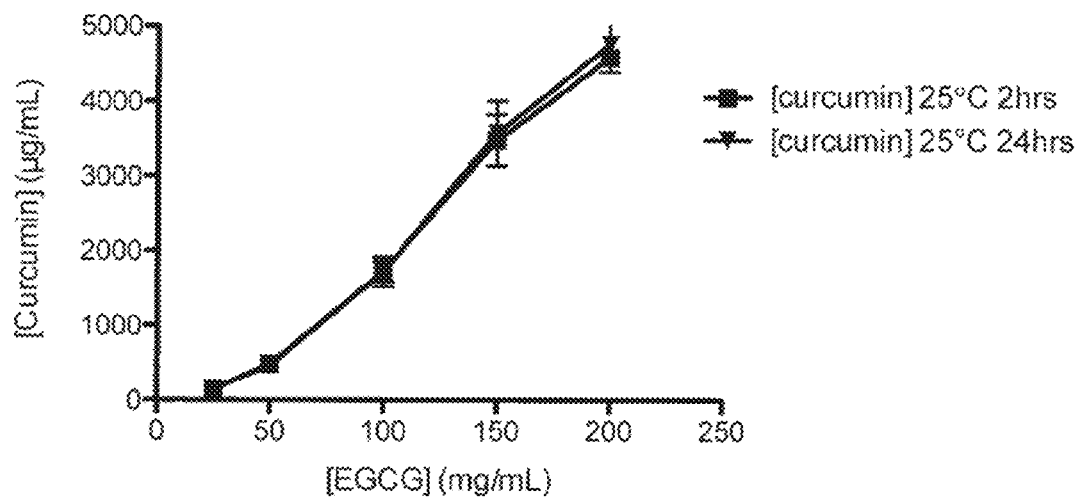
FIGS. 2(A)-(B) are graphs showing the solubility and stability of curcumin in solutions of EGCG FIG. 2(A) or tannic acid FIG. 2(B) after 2 hrs. and 24 hrs.

EGCG solubilised curcumin up to maximum concentrations of 200 mg per ml EGCG with curcumin at approximately 4700 microgram/ml. The solutions were stable for 24 hours (FIG. 2A). Tannic acid solubilised curcumin up to maximum concentrations of tannic acid at 500 mg/ml EGCG with curcumin at approximately 12000 microgram/ml. All solutions were stable for 24 hours but were temperature sensitive with much reduced curcumin solubilities at 37° C. or 50° C.

Figure 2B:
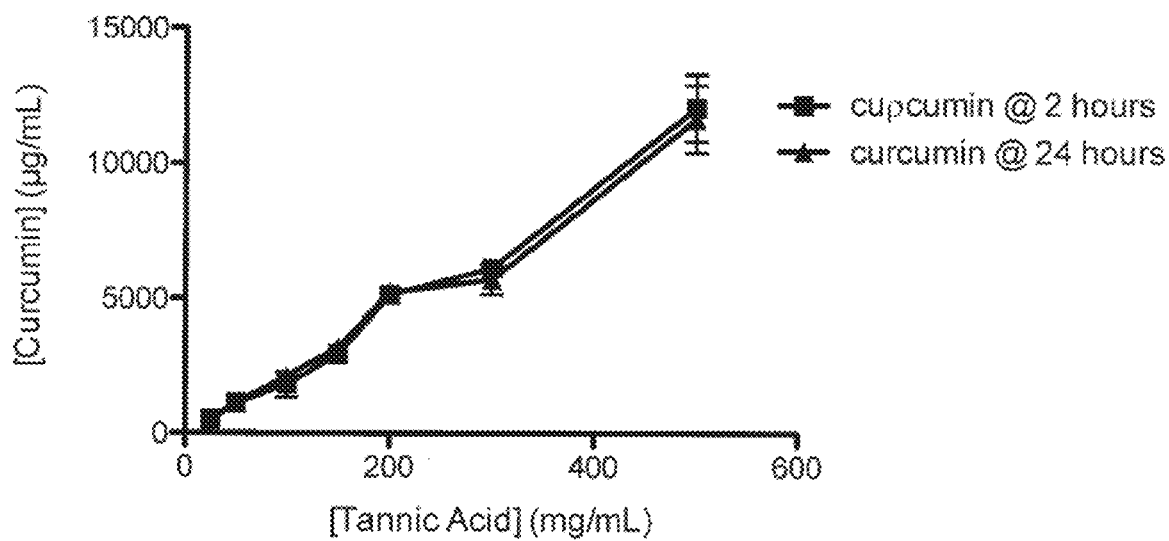

As shown in FIG. 2B, while the free solubility of curcumin is less that 1 microgram/ml in water, the presence of EGCG or tannic acid significantly increases the solubility of this drug.

Example 3. Solubility of Paclitaxel as a Function of EGCG or Tannic Acid Concentration, Effect of Temperature and 24 Hour Stability of Solutions Paclitaxel and EGCG or tannic acid were dried down from acetonitrile (EGCG) or methanol (tannic acid) solutions at various drug to EGCG or tannic acid ratios. PBS (EGCG) or water (tannic acid) was added and the final solution was filtered through a 0.22 micron filter to remove any particulates and the solution was analyzed for drug concentration using HPLC.

Figure 3A:
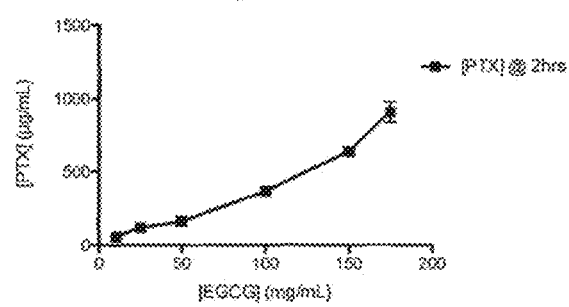
FIGS. 3(A)-(D) are graphs showing the solubility and stability of paclitaxel in solutions of EGCG (FIG. 3(A) and FIG. 3(C)) or tannic acid (FIG. 3(B) and FIG. 3(D)) at various times and temperatures.
Figure 3B:
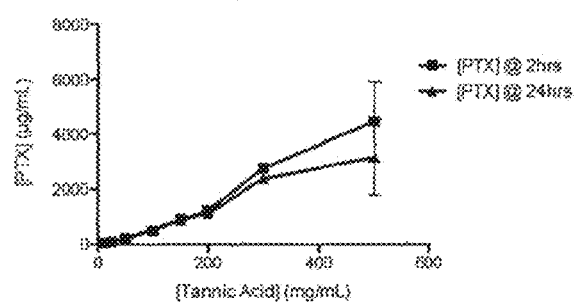
Figure 3C:
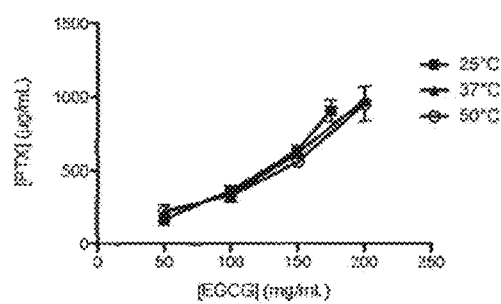
Figure 3D:
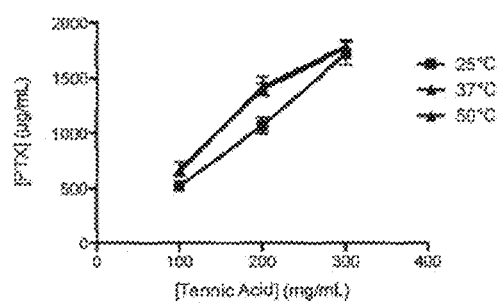

EGCG solubilised paclitaxel up to maximum concentrations of 175 mg per ml EGCG with paclitaxel at approximately 1000 micrograms/ml. However the solutions were not stable over 24 hours (FIG. 3A). Tannic acid solubilised paclitaxel up to maximum concentrations of 500 mg/ml tannic acid with paclitaxel at approximately 4800 microgram/ml. These solutions were stable for 24 hours (FIG. 3B). There was no effect of temperature on EGCG or tannic acid solubilization effects (FIGS. 3C and D). As shown in FIG. 3, while the free solubility of paclitaxel is 1 microgram/ml in water, the presence of EGCG or tannic acid greatly increases the solubility of this drug.

Example 4. Solubility of Docetaxel as a Function of EGCG or Tannic Acid Concentration, Effect of Temperature and 24 Hour Stability of Solutions Docetaxel and EGCG or tannic acid were dried down from acetonitrile (EGCG) or methanol (tannic acid) solutions at various drug to EGCG or tannic acid ratios. PBS (EGCG) or water (tannic acid) was added and the final solution filtered through a 0.22 micron filter to remove any particulates and the solution was analyzed for drug concentration using HPLC.

EGCG solubilised docetaxel up to maximum concentrations of 200 mg/ml EGCG with docetaxel at approximately 1500 microgram/ml. The solutions were stable over 24 hours (FIG. 4A). Tannic acid solubilised paclitaxel up to maximum concentrations 500 mg/ml tannic acid with paclitaxel at approximately 4000 micrograms/ml (FIG. 4B). However at tannic acid concentrations above 150 mg/ml the solutions were not stable over 24 hrs. There was no effect of temperature on the solubilization effects for either EGCG or tannic acid (FIGS. 4 C and D.) The free solubility of docetaxel is approximately 5-7 micrograms/ml in water. However, the presence of EGCG or tannic acid significantly increases the solubility of this drug.

Example 5. Solubility of Various Hydrophobic Agents in Solutions Containing EGCG EGCG at 50 mg/ml and drug at approximately 250 micrograms per ml were dissolved in the listed solvent and dried down in a test tube under nitrogen. 1 ml of water was added, followed by vortexing. The solutions were examined for particulate matter under a microscope. If no particulates were present, the process was repeated with a higher drug amount. All the tested drugs remained in solution at the listed concentrations except for nystatin and hesperdin.

TABLE 1

Drug concentrations obtained using EGCG at 50 mg per ml.

| Drug | Solvent | Drug Concentration microgram/ml | Particulates present | Visual appearance |
|---|---|---|---|---|
| curcumin | acetonitrile | 250 | no | clear yellow/orange solution |
| amphotericin | dmfthf | 125 | no | clear |
| camptothecin | thf/dmf | 50 | no | clear |
| plumbagin | acetonitrile | 250 | no | clear yellow/orange solution |
| indomethacin | acetonit | 250 | no | clear solution |
| quercetin | aceto/thf | 250 | no | clear coloured liquid |
| nystatin | aceto/thf (not fully) | 125 | very few | clear solution |
| ginkgolide B | aceto | 250 | no | clear solution |
| bilobalide | aceto | 250 | no | clear solution |
| hesperedin | aceto/THF | 125 | very few | almost clear |
| hesperetin | aceto | 250 | no | clear solution |

Example 6. The Increased Uptake of Paclitaxel into Cells Using Low Concentrations of EGCG Paclitaxel was incubated with canine kidney (mdck) cells and their drug resistant counterparts (mdck-mdr) alone or in the presence of EGCG at low concentrations (10 to 100 ug/ml). In these experiments, paclitaxel was found to diffuse into mdck cells to achieve levels of approximately 200 pg/mg cellular protein and less than this for mdck-mdr (due to drug efflux by the drug resistant pumps probably p-glycoprotein). However in cells co-incubated with paclitaxel and EGCG at 50 microg/ml paclitaxel achieved concentrations as high as 2000 pg/mg in both mdck and mdck-mdr cells.

The 10 fold increase in drug uptake in mdck and mdck-mdr cells points to a close association of paclitaxel with EGCG and a transport-assisted influx of the drug into the cells. This increased drug uptake is another unique feature associated with the combined use of EGCG with hydrophobic drugs.

Example 7. The Increased Uptake and Transport of Docetaxel Through Monolayers of Cells The canine kidney cells, known as MDCK cells, are a non cancer proliferating cell line from canine kidneys. The MDR derivative of these cells is a multi-drug resistant version. The cell lines MDCK and MDCK-MDR are routinely used in the field of drug resistance because in the MDCK cells drugs can accumulate and kill the cells whereas the MDR cells contain drug efflux proteins that efflux the drug so that much higher drug doses are needed to maintain intracellular concentrations sufficient to kill these cells. Agents that can increase the intracellular concentration of drugs in MDR cells may be useful in overcoming drug resistance or in allowing drugs to enter tissue areas protected by efflux proteins (e.g. uptake in the gut or brain).

MDCK cells were seeded at 10000 cells per transwell membrane (Becton and Dickenson: 0.3 microns, 1 cm diameter) and grown for one week until a continuous monolayer was present. Drug at 250 micrograms/ml (doped with $^3$H docetaxel, with carrier (tween, diblock (2000 40-60) PDLLA-mepeg or EGCG), all in hanks buffer, were added to the top well (0.4 ml) with 1.2 ml of hanks buffer in the base well. The wells were incubated at 37° C. for two hours. The transwells were then disassembled and the amount of drug in the base reservoir (transported through the cells) or in the cells (determined by dissolution of the filter after 3 washes in hanks buffer) was determined by liquid scintillation counting.

In both cell lines, the amount of docetaxel accumulated in the cells or transported through the cells was increased when cells were incubated with EGCG-docetaxel solutions as compared to tween or diblock copolymer micellar solutions. These results illustrate that EGCG allows for enhanced accumulation of docetaxel in cells (FIG. 5).

Example 8. The Transport of Curcumin Through Caco2 Cells

Caco2 cells are continuous cells of human epithelial colorectal adenocarcinoma cells. They contain drug efflux proteins and may be used in the same way that MDCK-MDR cells are, i.e. to measure drug accumulation in cells that have the ability to efflux drugs.

Caco2 cells (ATCC, VA, USA) are proliferating gut epithelial cells used throughout the pharmaceutical sciences as a model of oral drug availability. These cells may be grown in cell culture on membranes where they align with an apical external surface (equivalent to the gut lumen) and a basolateral lower surface that is equivalent to the cell side adjacent to the blood capillaries. When an EGCG curcumin solution was placed in the upper portion of a transwell containing these cells on a membrane for three hours, large amounts of curcumin either passed through or accumulated within the caco2 cells.

Caco2 cells were seeded onto 0.3 um transwell membranes and left to grow to confluence for 3 days. A conductivity electrode measured the Transcellular electrical resistance value over the next few days and when it had reached 600 mohms (tight junctions established) the experiment began. A solution of curcumin (250 microgram per ml) in EGCG (25 mg per ml) in Hanks buffer pH 7.4. was added to the top well for 3 hours. The bottom reservoir, which contains curcumin that has been transported through the cells, was collected. The filter containing curcumin inside cells was washed three times in Hanks buffer and then solubilised in acetonitrile to release intracellular curcumin. All solutions were then analyzed for curcumin content using uv-vis absorbance spectroscopy at 430 nm.

FIG. 6 shows the transport of curcumin through cells in the presence of EGCG and also when EGCG is replaced by a diblock polymer (40/60 PDLLA1330-2000 mepeg. Although the diblock copolymer allowed a small amount of curcumin to pass through and enter the cells, the EGCG solution allowed for much higher levels of curcumin uptake and transport through the cells (FIG. 6). This example clearly illustrates that EGCG solutions of hydrophobic drugs may be used to render the drugs orally available.

Example 9. Coating of Catheters with Fast Dissolving, Drug Solubilising Coatings Diblock copolymer was manufactured in house. Briefly, methoxypolyethylene glycol (MEPEG molecular weight 2000) (Union Carbide), was placed in a sealed round bottomed flask along with lactic acid (Sigma Chemicals) and heated under nitrogen in an oil bath to 140° C. for 24 hours. Lactic acid then polymerizes on the hydroxyl chain of the MEPEG to form a diblock copolymer. The amounts of lactic acid added was determined to give a molecular weight polylactic acid chain of approximately 1660 joined to the MEPEG 2000 to give a final molecular weight of 3660. This was checked and established by gel permeation chromatography.

When this diblock copolymer is dissolved with hydrophobic drugs in an organic solvent such as acetonitrile and dried down then upon addition of water the diblock copolymer may dissolve to form micelles in which the drug is found in the micelle core. This allows for the solubilization of the drug.

30 mg of EGCG, or 10 mg tannic acid or 6 mg of diblock copolymer (40/60 PDLLA1330-2000 mepeg) and 300 micrograms of paclitaxel were dissolved in 400 ul of ethanol. A balloon catheter was inflated and revolved along its horizontal axis. The drug/EGCG solution was slowly pipetted onto the balloon using 25 microliters at a time and dried with gentle heat from an electric blowdryer. The catheter was left overnight to dry. The diblock copolymer was mixed with EGCG at defined ratios to give a final weight of 30 mg.

The coating was found to be strongly bound to the balloon and did not rub off with glove abrasion. The balloon could be inflated/deflated many times with no compromise of adhesion of the coating. When these coatings containing 10% drug to carrier were placed in water or 5% dextrose for a few seconds a fine precipitate was observed in the carrier before the carrier dissolved. These precipitates were analyzed (Nanosizer, Malvem) and found to have a size of 110 nm. If left in PBS the precipitates aggregated to 2 micrometers in size. However, if moistened in PBS and then dispersed in water or dextrose they formed nanoparticles having a diameter of approximately 110 nanometers.

Although these precipitates only occurred at higher drug to carrier ratios, such drug nanoparticles can offer an optimal form of solid drug delivery to tissues. This may be especially true on an artery wall since uptake into the tissue would be potentially improved as compared to much larger sized drug precipitates. In some coatings excipients such as polyethylene glycol or glycerol or hydroxypropylcellulose were added. These coatings performed in the same way as non excipient coatings form a drug perspective but the coatings were more flexible and may be preferred for certain applications.

Example 10. The Rate of Paclitaxel Release from EGCG Carrier Coatings on Balloon Catheters A balloon catheter was inflated and revolved along its horizontal axis. 30 mg of EGCG, and 300 microg of paclitaxel were dissolved in 400 ul of ethanol. The drug/EGCG solution was slowly pipetted onto the balloon using 25 microliters at a time and dried with gentle heat from an electric blowdryer. The catheter assembly was then left overnight to dry. To measure the drug release the catheter was inflated and immersed in 5 ml of PBS-albumin buffer at pH 7.4 for a specific time with mild revolution to create movement. The catheter was then removed and placed in a new tube containing 5 ml of PBS-Albumin for the second drug release time point. One ml of dichloromethane was added to each 5 ml of PBS and the tube shaken. The contents were allowed to settle and the top liquid aspirated off. The dichloromemethane was allowed to dry and then the solids were redissolved in 60/40 acetonitrile/water v/v and drug quantitated by HPLC analysis (c18 column, 58/5/37 acetonitrile/methanol/water at 1 ml/min flow rate with detection at 232 nm)

For zero percentage diblock copolymer (i.e. EGCG alone) all paclitaxel was released in one minute. For 10 percentage diblock copolymer and 20 percentage diblock copolymer the rate of release of paclitaxel was slightly slower from the catheters but was complete within 2 minutes. The addition of 50% diblock copolymer slowed the release rate dramatically as is seen in FIG. 7.

Example 11. Paclitaxel Uptake into Artery Tissue from a Balloon Catheter Coated with Drug and EGCG A balloon catheter was coated as in example 10 with 30 mg of EGCG and 300 microgram of paclitaxel in 400 microliters of ethanol also containing 10 microliters of $^3$H paclitaxel. A 2-3 cm strip of fresh rat aorta artery was placed over a 200 microliter pipette tip and fed onto the deflated balloon catheter to mimic the feeding of the balloon into the blood vessel. The balloon was then inflated and the system was left for 2 minutes at 37° C. in a bath of Hanks buffered salt solution (HBSS). The balloon was then deflated and 300 microliters of HBSS pipetted into the artery and the wash out collected in a centrifuge tube. This wash step was repeated three times. Because the handler's gloves were moist and had contacted the balloon (and therefore absorbed some EGCG/drug) the gloves fingers were washed extensively in 100 ml of HBSS.

The aorta tissue was placed in 500 microliters of tissue solubilizer and left at 60° C. for 4 hours to digest. The contents were then placed in a scintillation counter. The deployed catheter balloon was observed after the procedure. Some of the balloon had not deployed (the balloon was tight in the aorta and not fully inflated) and traces of the reddish colored EGCG/drug could be observed in the folds. The rest of the catheter was observed to be clear of all coating. The catheter balloon was then inflated in 5 ml of acetonitrile to recover the undissolved EGCG and measured by scintillation counting. All other fractions (aorta wash and gloves wash were also counted. These four fractions (aorta, gloves, catheter residual and aorta wash) accounted for all drug and the total scintillation count form everything was taken and 100% of the applied drug.

More than 50% of the total paclitaxel was found to be associated with the artery and only 2% washed out of the artery following balloon deployment. (FIG. 8) The other fractions (residual in catheter folds and gloves wash) are not really relevant as they were deemed unavailable drug since that drug was never exposed to the artery wall. Ignoring those fractions, then approximately 95% of available paclitaxel was taken up by the artery and less than 5% washed out from the artery. These results clearly show that EGCG allows for excellent paclitaxel transfer into arteries following a 2 minute contact time.

Example 12. Effect of Ultrasound on Paclitaxel Uptake into Artery Tissue from a Balloon Catheter Coated with Drug and EGCG 30 mg of EGCG, and 300 ug of paclitaxel were dissolved in 400 ul of ethanol also containing 10 ul of $^3$H paclitaxel. A balloon catheter was inflated and revolved along its horizontal axis. The drug/EGCG solution was slowly pipetted onto the balloon using 25 microliters at a time and dried with gentle heat from an electric blowdryer. A 2-3 cm strip of fresh rat aorta artery was placed over a 200 microliter pipette tip and fed onto the deflated balloon catheter to mimic the feeding of the balloon into the blood vessel. The balloon was then inflated and the system was sonicated for 2 minutes at 37° C. in Hanks buffered salt solution (HBSS) (4 MHz, 30 watts/cm2). The balloon was then deflated and 300 microl of (HBSS) was pipetted into the artery and the wash out collected in a centrifuge tube. This wash step was repeated three times. Samples were collected as in the previous example.

More than 50% of the total paclitaxel was found to be associated with the artery and only 2% washed out of the artery following balloon deployment. (FIG. 9). The other fractions (residual on catheter and gloves wash) are not really relevant as they were deemed unavailable drug since that drug was never exposed to the artery wall. Ignoring those fractions, then approximately 95% of available paclitaxel was taken up by the artery and less than 5% washed out from the artery. These results clearly show that EGCG with ultrasound allows for excellent paclitaxel transfer into arteries following a 2 minute contact time.

Example 13. Paclitaxel Uptake into Artery Tissue from a Balloon Catheter Coated with Drug and Diblock Copolymer A balloon catheter was inflated and revolved along its horizontal axis. The drug/diblock solution was slowly pipetted onto the balloon using 25 microliters at a time and dried with gentle heat from an electric blowdryer. The solution contained 6 mg of diblock copolymer (40/60 pdl-la.mepeg-2000 mol. wt. 3333) and 300 ug of paclitaxel in 400 ul of ethanol also containing 10 ul of $^3$H paclitaxel. A 2-3 cm strip of fresh rat aorta artery was placed over a 200 ul pipette tip and fed onto the deflated balloon catheter to mimic the feeding of the balloon into the blood vessel. The system was then immersed in Hanks buffered salt solution (HBSS) at 37° C. for 2 minutes. At this time the balloon and treated and the paclitaxel uptake determined as in Example 11.

Approximately 10% of the total paclitaxel was found to be associated with the artery and less than 2% washed out of the artery following balloon deployment. (FIG. 10). The gloves wash fraction is not really relevant as it was deemed unavailable drug since that drug was never exposed to the artery wall. The residual on the catheter was significant and it is not known if that drug represented drug in undeployed balloon folds or was undissolved coating. The diblock copolymer does offer a suitable coating but use may be limited to thinner layers that dissolve more quickly.

Example 14. Paclitaxel Uptake into Artery Tissue from a Balloon Catheter Coated with Drug and Tannic Acid 30 tannic acid and 300 ug of paclitaxel were dissolved in 400 ul of ethanol also containing 10 ul of $^3$H paclitaxel. A balloon catheter was inflated and revolved along its horizontal axis. The drug/tannic acid solution was slowly pipetted onto the balloon using 25 microliters at a time and dried with gentle heat from an electric blowdryer. Uptake of paclitaxel by a 2-3 cm strip of fresh rat aorta artery was then determined using the procedure described in Example 11.

Approximately 40% of the total paclitaxel was found to be associated with the artery and less than 1% washed out of the artery following balloon deployment. (FIG. 11.) The gloves wash fraction is not really relevant as it was deemed unavailable drug since that drug was never exposed to the artery wall. The residual on the catheter was approximately 29% and it is not known if that drug represented drug in undeployed balloon folds or was undissolved coating. The amount in the tissue represents the largest fraction of the drug. If we ignore the drug on the catheter and on the gloves then this amount represents over 95% of the available drug transferred to the tissues clearly showing that tannic acid represents an excellent vehicle for docetaxel delivery from catheters to the blood vessel.

Example 15. Accumulation of Docetaxel in HUVEC Cells and Effect of Ultrasound

Human umbilical vein endothelial cells (HUVEC) and the associated culture media were obtained from Lonza Chemicals (Basel, Switzerland). All cells were applied to 48 well plates in respective media at a concentration of 5000 cells per well or filter. The cells were allowed to equilibrate for 3 days at which time they became approximately 80% confluent. In the 48 well plates, only 24 wells were used per plate so that wells with cells appeared in a checkerboard pattern.

After 2 days, cells were ready for drug incubation with or without ultrasound treatment. The drug solutions (including radiolabelled docetaxel) were applied to the cells (0.5 ml) for 2 hours. Some cells were then ultrasonicated. Briefly, cells received a single 10-s burst of ultrasound at 4 MHz with a power density of 30 W/cm$^2$.

After ultrasound treatment, the drug solution was immediately removed and all cells were washed three times with 500 ul of HBSS. The amount of docetaxel retained in the cells was determined by lysing the cells in 200 ul of lysis buffer (2% Triton X100 containing 33% DMSO) and quantitation by liquid scintillation counting.

The uptake of docetaxel into huvec cells from ECGC formulations was approximately 4 fold higher than form the micellar formulation of the drug (FIG. 12). The application of ultrasound increased the uptake of drug into cells from all formulations.

Example 16. Uptake and Transfer of Amphoterecin B into Caco2 Cells Using EGCG, Tannic Acid or Ambisome Formulations Caco2 cells were seeded onto 0.3 um transwell membranes and treated as in Example 9. A solution of amphoterecin B (250 ug per ml) in EGCG (25 mg per ml), tannic acid (25 mg/ml) in Hanks buffer pH 7.4. or ambisome was added to the top well for 3 hours. The bottom reservoir was collected and treated as in Example 8. All solutions were then analyzed for amphotericin content using uv-vis absorbance spectroscopy at 407 nm.

Although the ambisome formulation of amphotericin allowed a small amount of drug to pass through and enter the cells, the EGCG and tannic acid solutions allowed for much higher levels of drug uptake and transport through the cells (FIG. 13).

Example 17. Manufacture of PAMAM Dendrimer-Crosslinked Gallic Acid Compounds

Protocol for two-step coupling of gallic acid to Go dendrimer using EDC and Sulfo-NHS.

Introduction: TheGo PAMAM dendrimer (Dendritech Midland Mich.) has four arms each with an amine group on the end terminus. This molecule (molecular weight 517) may be linked to the carboxylate on 4 gallate molecules using the carbodiimide molecule (EDC) (ethyl dimethyl aminopropyl carbodiimide Sigma chemicals USA) in aqueous media.

Materials
A. Activation buffer: water adjust to pH 6
C. gallic acid 440 mg (Sigma chemicals)
D. Sulfo-NHS (Product No. 24510. Thermo fisher)
E. EDC (Sigma chemicals)
F. dendrimer GO. (Dendritech) 1 ml at 2 g/16 ml=125 mg
Method 573 mg EDC (~1.5M) and 868 mg of sulfo-NHS (~2M) was added to 2 ml of water at pH 5-6 with 440 mg of gallic acid (1.3M in 15% ETOH to dissolve) and reacted for 30 minutes at room temperature at pH 4-7. This depended on keeping the gallic acid in solution with stirring. If the reagent did not go into solution, additional water was added.

1 ml of GO dendrimer (120 mM in 1 ml or 40 mM in 3 ml) was added and the pH was adjusted to between 7 and 8.5. Reacted for 2 hours. The reaction mixture was placed in a dialysis bag at about 500 cut off overnight to yield the final product. The reaction scheme is shown in FIG. 14.

Example 18. Drug in EGCG or Tannic Acid Films, Effect of PEG or Glycerol

Thin films of drugs were cast in either EGCG or tannic acid from ethanol solutions. Drugs in either EGCG or tannic acid were dissolved in ethanol at a final total concentration of 20% w/v and spot pipetted in repeated 10 microliter volumes and allowed to dry between spotting. This allowed a thin film to accumulate and dry. Some solutions contained either glycerol or polyethylene glycol 300 at 10% or 20% w/w to EGCG or tannic acid. The films were allowed to dry and examined by optical microscopy for drug precipitation. Films were allow analyzed by differential scanning calorimetry (DSC) for identify drug crystals.

Curcumin precipitated out at approximately 5% w/w. However, paclitaxel and docetaxel remained dispersed at the molecular level up to 90% drug loadings. The presence of paclitaxel crystals was confirmed at 90% drug loadings by DSC. Rapamycin remained in solution at 50% or more drug:EGCG or tannic acid levels. (FIG. 15) The addition of PEG 300 or glycerol at 10% had no significant effect on these values. However, films were slightly more flexible following the addition of these agents at 10 to 20% w/w/ to EGCG or tannic acid.

These data were unexpected since paclitaxel precipitates out of polymeric films at approximately 5% loadings. The high levels of molecular level drug in EGCG or tannic acid films offers a way of maintaining drugs like paclitaxel, docetaxel or rapamycin in a tissue available form (molecular rather than particulate) in film coatings of devices.

Example 19. Electrospun EGCG/Drug Complexes in Hydrophobic Polymer

Polylactic co glycolic acid was dissolved in 75:25 tetrahydrofuan:dimethly formamide at 20% w/v. EGCG or tannic acid at 30% to the PLGA solution along with paclitaxel or curcumin at 2% w/w to EGCG or tannic acid. The solution was electrospun at 20000 volts onto aluminium foil. After three hours a fine matt of nanofibers had been spun. Under microscope inspection the meshes appeared homogenous in nature.

Example 20. Solubility of Rapamycin as a Function of EGCG or Tannic Acid Concentration, Effect of Temperature, pH and Stability at 24 Hours Rapamycin and EGCG or tannic acid were dried down from acetonitrile (or methanol for tannic acid) solutions at various drug to EGCG or tannic acid ratios. PBS (EGCG) or water (Tannic acid) was added and the final solution was filtered through a 0.22 um filter to remove any particulates and the solution was analyzed for drug concentration using HPLC.

Figure 16A:
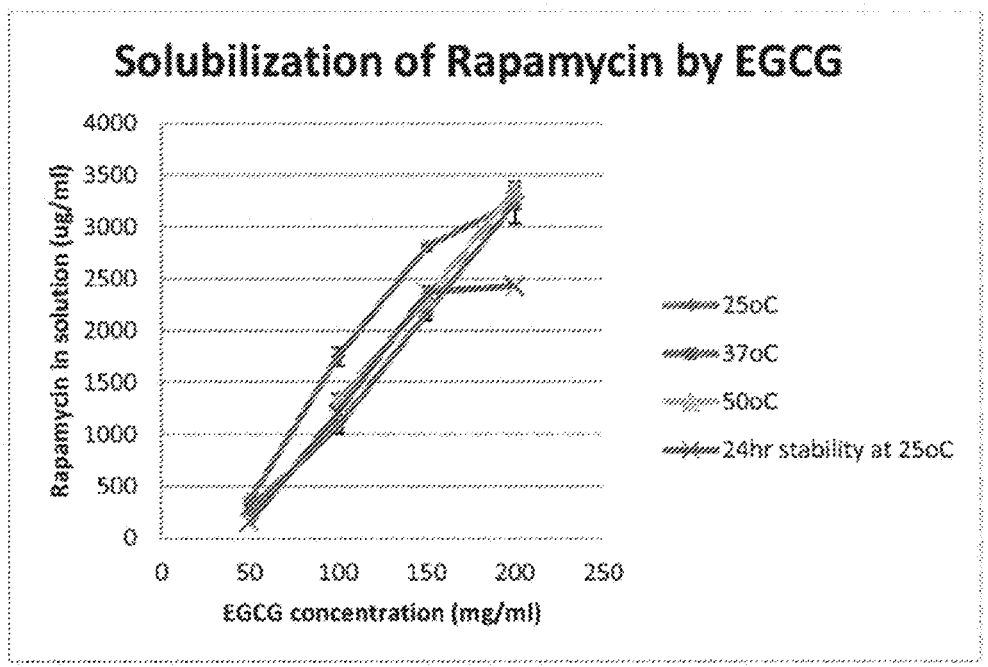
FIGS. 16(A)-(B) are graphs showing the solubility and stability of rapamycin in solutions of EGCG (FIG. 16(A)) or tannic acid (FIG. 16(B)) after 2 hrs. and 24 hrs.
Figure 16B:
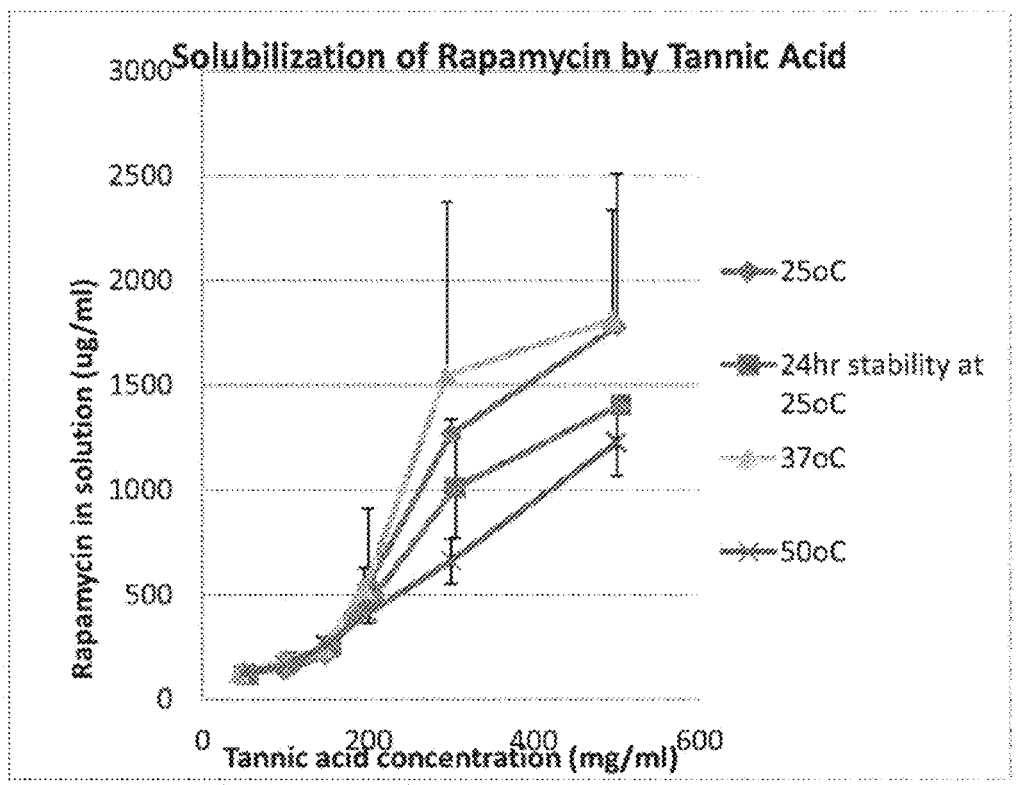

EGCG solubilized rapamycin up to maximum concentrations of 200 mg per ml EGCG with amphotericin at approximately 300 microgram/ml. Solutions were stable for 24 hours (FIG. 16(*a*)). There was little effect of temperature on solubility levels Tannic acid solubilised rapamycin up to maximum concentrations of 500 mg per ml Tannic acid with amphotericin at approx. 1500 ug/ml. Solutions were stable for 24 hours (FIG. 16(*b*). There was no effect of temperature on solubility levels As shown in FIG. 16, while the free solubility of rapamycin is approximately 2-3 ug/ml in water, the presence of EGCG or tannic acid is able to massively increase the solubility of this drug.

Example 21. Rapamycin Uptake into Artery Tissue from a Balloon Catheter Coated with Drug and EGCG The balloon catheter was coated with 30 mg of ECGC and 300 microg of rapamycin in 400 ul of ethanol. A 2-3 cm strip of fresh rat aorta artery was placed over a 200 ul pipette tip and fed onto the deflated balloon catheter to mimic the feeding of the balloon into the blood vessel. The balloon was then inflated and the system was left for 2 minutes at 37° C. in a bath of hanks buffered salt solution (HBSS). At that time the balloon was deflated and 300 microliters of HBSS was pipetted into the artery and the wash out collected in a centrifuge tube. This wash step was repeated three times. Because the handler's gloves were moist and had contacted the balloon (and therefore absorbed some EGCG/drug) the gloves fingers were washed extensively in 100 ml of HBSS. The aorta tissue was placed in 500 ul of ethanol and cut up with fine scissors and then homogenized (polytron at mark 3 for 30 seconds). The deployed catheter balloon was observed after the procedure. Some of the balloon had not deployed (the balloon was tight in the aorta and not fully inflated) and traces of the reddish colored EGCG/drug could be observed in the folds. The rest of the catheter was observed to be clear of all coating. The catheter balloon was then inflated in 5 ml of acetonitrile to recover the undissolved egcg and drug measured by HPLC. All other fractions (aorta wash and gloves wash) and catheter extracts were analyzed by HPLC. These four fractions (aorta, gloves, catheter residual and aorta wash) accounted for all drug and the total HPLC drug amount was taken and 100% of the applied drug.

Figure 17:
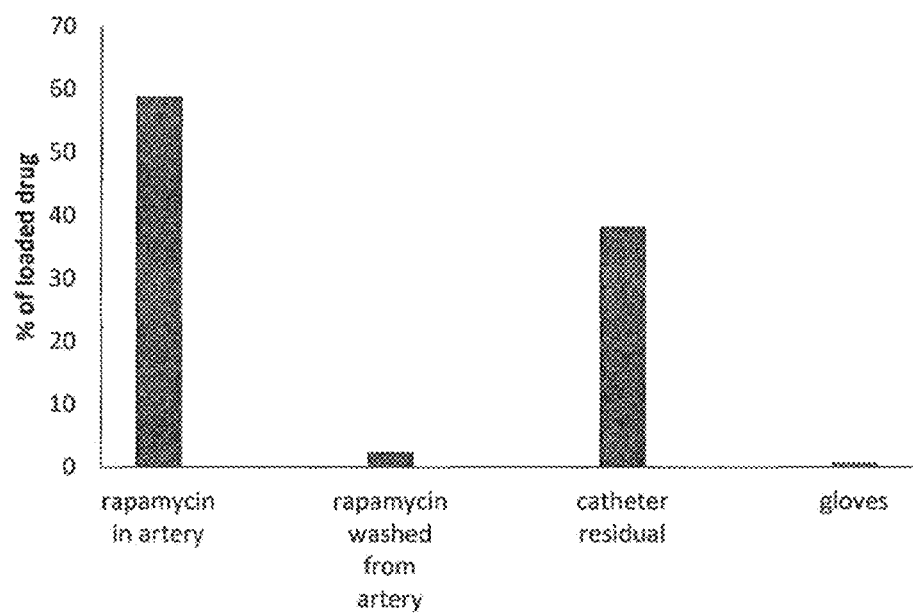
FIG. 17 is a graph showing the transfer of rapamycin to an artery wall from an EGCG coated balloon catheter.

Results: More than 50% of the total paclitaxel was found to be associated with the artery and less than 2% washed out of the artery following balloon deployment. (FIG. 17) The other fractions (residual in catheter folds and gloves wash) are not really relevant as they were deemed unavailable drug since that drug was never exposed to the artery wall. If we ignore those fractions, then more than 95% of available paclitaxel was taken up by the artery and less than 5% washed out from the artery. These results clearly show that EGCG allows for excellent rapamycin transfer into arteries following a 2 minute contact time.

Example 22. Finasteride Solubilization in ECGC or Tannic Acid and Measurement the Encapsulation and Release of Finasteride from PVA and Embospheres Following Incubation in EGCG or Tannic Acid Solution of Finasteride The solubilization effect of EGCG or tannic acid on finasteride.

Method: Solutions of finasteride and either EGCG or tannic acid at various weight percentages in ethanol were dried down under nitrogen. Water was added and the dried material suspended/dissolved. The contents were then centrifuged at 3000×G and filter through a glass filter (1 um) and finasteride solubility determined by HPLC. The pH of tannic acid solutions was brought up to 7 by the addition of NAOH. EGCG has little effect on pH (drops to pH 6 at 200 ug/ml) so these solutions were not adjusted.

Results: EGCG increased the solubility of finasteride in a concentration dependent manner. At 150 mg/ml EGCG the solubility of finasteride was elevated from 75 ug/ml to over 10 mg/ml at either 25° C. or 37° C. and solutions were stable over 24 hours at 25° C. A similar effect was observed for tannic acid which allowed for a finasteride solubility of 8-10 mg/ml using tannic acid at 200 mg/ml.

Method: PVA foam embolization particles (Cook. Medical Bloomington Ind.) size 180-300 um. Vial of 220 mg split into two. 150 mg of EGCG with 10 mg of finasteride or 250 mg tannic acid with 1 mg of finasteride were dried as a common film from ethanol and solubilised in 1 ml of water and added to the 100 mg of PVA particles. Solutions were mixed for 30 minutes. At this time it was observed that all the EGCG or tannic acid color (pink or brown respectively) had disappeared from the solution and gone into the PVA which was now heavily colored. The solution was discarded and the PVA freeze dried. 10 mg of the EGCG formulation or 5 mg of the tannic acid formulation was added to 2 ml of PBS (pH 7.4) and the release of finasteride was measured over 2 weeks.

Embospheres: Syringe contents ((Embospheres 500-700 um Merit Medical S. Jordan UT) were split into two and incubated in water solutions of finasteride (1 mg/ml in 35 mg of EGCG or tannic acid made up from dried films as above) for 30 minutes with shaking. At this time it was observed that all the EGCG or tannic acid color (pink or brown respectively) had disappeared from the solution and gone into the Embospheres which were no heavily colored. The solution was discarded. 20% of the resulting particles (still wet) were then placed in microcentrifuge tubes containing 2 ml of PBS and drug release was measured.

Figure 18:
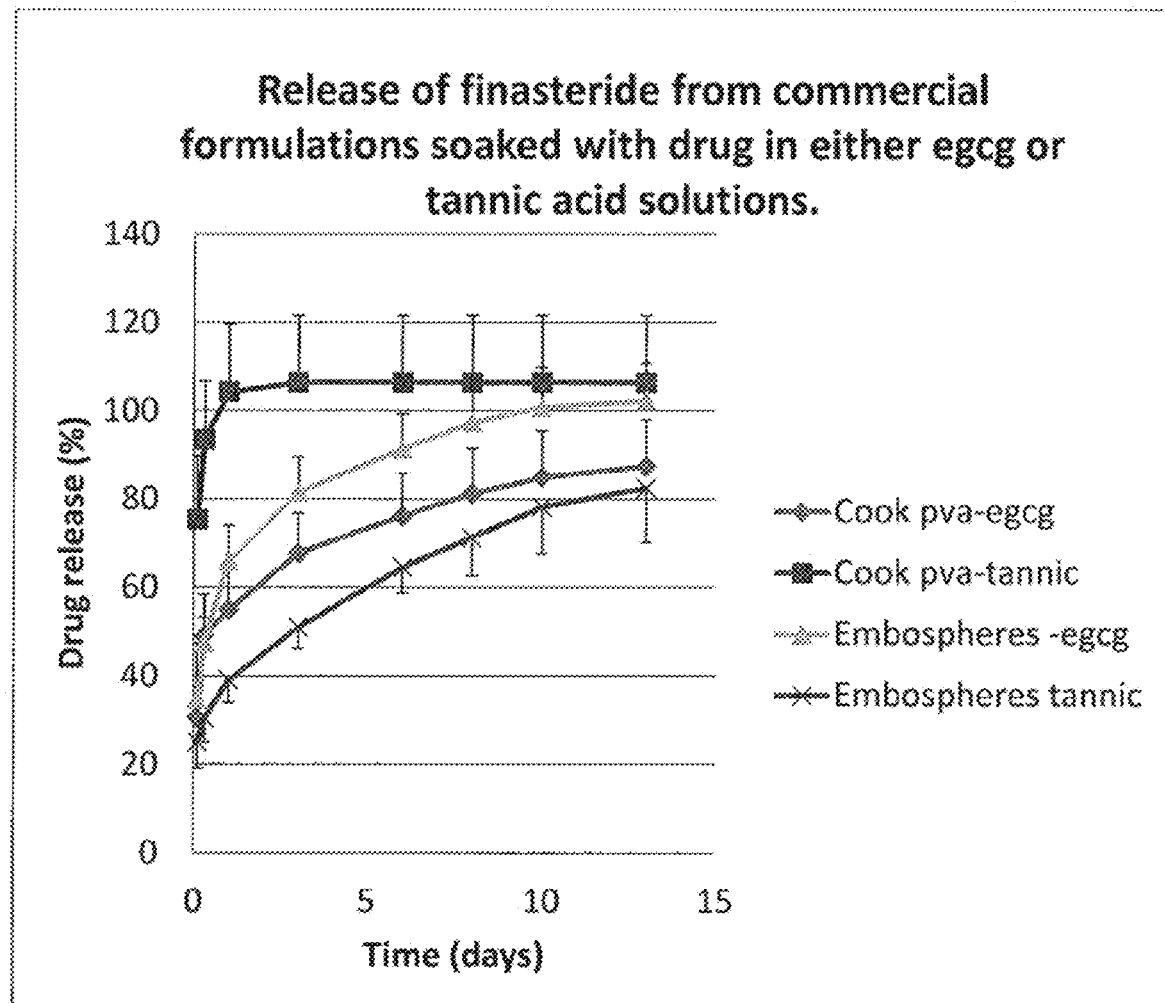
FIG. 18 is a graph showing the release of finasteride from embospheres (Merit Medical) or PVA foam embolic particles (Cook Medical).

Results: All formulations released the drug in a controlled manner. The fastest release observed was for PVA incubated with tannic acid/finasteride solutions (100% release in 3 days) whilst the other embolic particles released the drug over a two week period. (FIG. 18)

Example 23. Release of Finasteride from PLGA Microspheres+/−Egcg or Tannic Acid

Encapsulation pf paclitaxel and tannic acid or EGCG in PLGA microspheres of approximately 200 micrometers diameter.

Method: The method involved pipetting a solution of the polymer PLGA (usually 20% w/v) and drug (usually 5% w/w to polymer) and EGCG (e.g. 20% w/w/ to polymer) in dichlomethane (DCM) (5 ml) into 100 ml of 2.5% PVA solution in water stirring at 450 rpm. The suspension was left stirring for 2 hours and the microspheres washed 4 times in distilled water. The microspheres were then dried under vacuum for 2 days. Drug encapsulation was measured by dissolving a known weight of microspheres in 1 ml of dichloromethane followed by immediate dilution to 10 ml in 60:40 acetonitrile/water. The amount of drug or EGCG in the top and bottom phase of this solution was measured using HPLC methods (mobile phase 58:37:5 Acetonitrile:water:methanol. 1 ml per min flow on a c18 column with detection at 232 nm)

Results: Both EGCG and paclitaxel were encapsulated at high efficiency (greater than 50% efficiency) in PLGA microspheres. Yields of microspheres were good (greater than 50%). Microspheres were approximately 200 micron in diameter and there was clear evidence of EGCG in the spheres which appeared pink in color (color of EGCG) and under optical microscopy, small particles of EGCG could be seen with the PLGA microspheres.

Tannic acid: An alternative method was used, termed a water-in oil-in water emulsion. This method involved pre-dissolving the tannic acid in a small volume (typically 200 micrometers) of 0.05% Span 80 in water and adding this immiscible water phase to the PLGA/paclitaxel/DCM phase with tip sonication. This forms a primary emulsion of water droplets in the PLGA solution stabilized by Span. When this emulsion was pipetted into the PVA solution the microspheres formed well. Using this method microspheres (200 micrometers) were obtained at high yields (greater than 50%) with high loadings of both paclitaxel and tannic acid (greater than 50%). The microspheres were a light brown in color indicative of tannic acid encapsulation.

Methods: In these studies, 10 mg of microspheres were suspended in 2 ml of phosphate buffered saline (pH 7.4 10 mM phosphate) in microcentrifuge tubes and tumbled at 8 rpm at 37° C. The tubes were then centrifuged at 12000×g and the supernatants collected for drug analysis by HPLC. 2 ml of fresh PBS was then placed on top of the microspheres which were returned to the 37° C. oven for continued incubation with tumbling.

Figure 19:
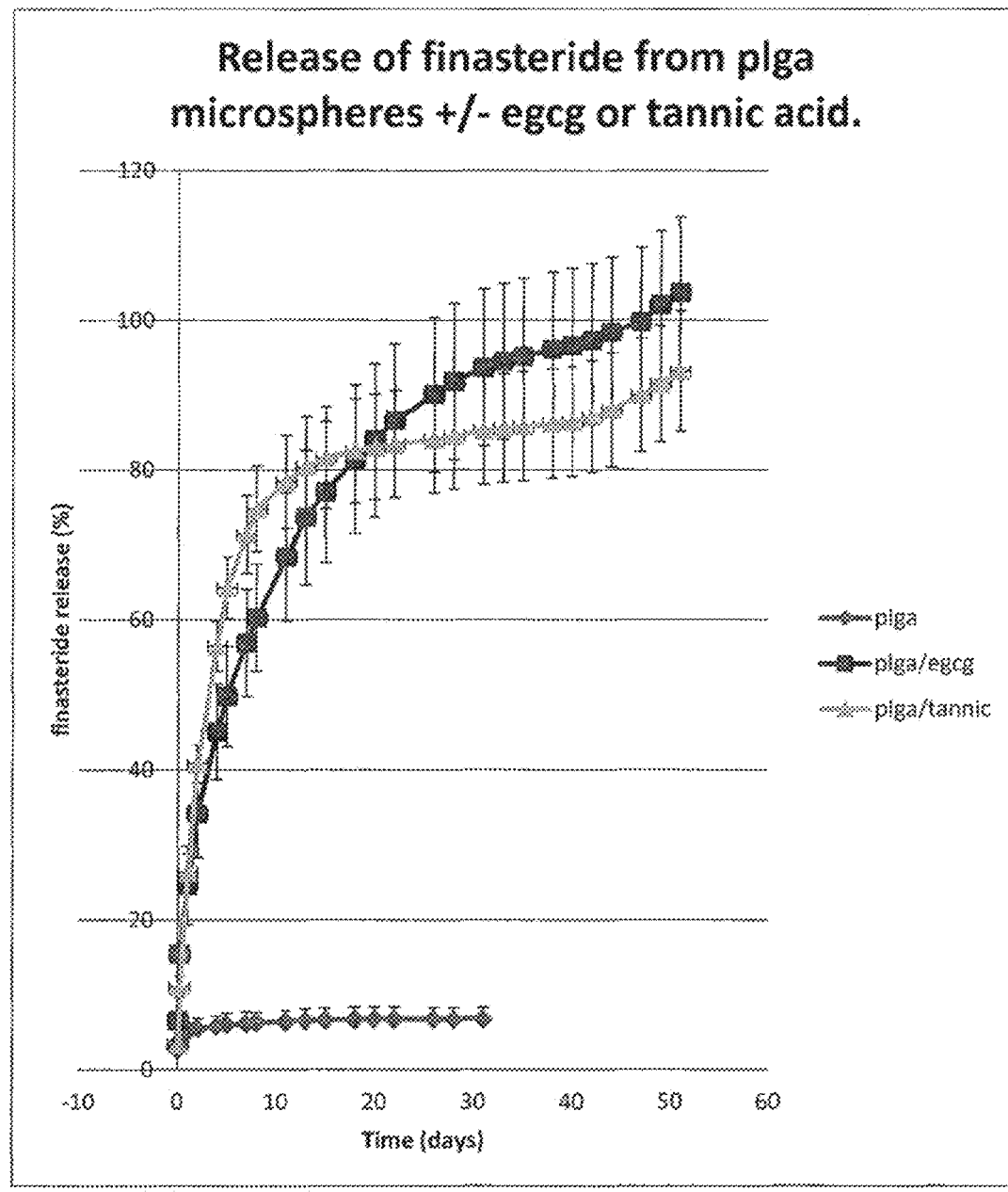
FIG. 19 is a graph showing the effect of EGEC or Tannic Acid on the release of finasteride from PLGA microspheres.

Finasteride: The release rate of finasteride from the PLGA microspheres is shown in FIG. 19. Finasteride released very slowly from the PLGA if no EGCG or Tannic acid was included in the formulation so that only 7% of encapsulated drug had released after 32 days. However the addition of either EGCG or Tannic acid to the microspheres greatly enhanced drug release rates so that for both systems a steady release rate of finasteride was obtained over the first 20 days (approx 80% of drug released) followed by a slower steady release over the next 20 days. After approx 40 days the release rate increased again until the microspheres had completely broken up and degraded by day 50.

At the end of the study the residual mass of polymer and drug was dissolved in DCM and drug extracted into 60:40 acetonitrile:water to measure residual drug. The amounts of residual drug were 89% for plga alone (at 31 days), 16% for EGCG and 8% for tannic acid (both at 51 days) as expressed as a % of the original loading. These results approximately match the release profiles in that almost all the drug remained in the PLGA alone spheres and only a small amount of drug remained in the polymer for the EGCG and Tannic acid formulations.

EGCG or Tannic acid: The release of EGCG or Tannic acid from PLGA microspheres was also measured. Both EGCG and Tannic acid released steadily over a 10 days period to levels of approximately 45% and 65% respectively. After that time the release rate was very slow and was non detectable by day 31.

These profiles establish the excellent qualities of PLGA microspheres containing EGCG or Tannic acid as controlled release formulations of finasteride. The continued release of EGCG or Tannic acid over 30 days also allows some controlled release of these compounds.

Example 24. Solubility of Finasteride as a Function of EGCG or Tannic Acid Concentration; Effect of Temperature and 24 Hour Stability of Solutions Method: drug and EGCG or tannic acid were dried down from acetonitrile (or methanol for tannic acid) solutions at various drug to EGCG or tannic acid ratios. PBS (EGCG) or water (Tannic acid pH adjusted to 7) was added and the final solution was filtered through a 0.22 um filter to remove any particulates and the solution was analyzed for drug concentration using HPLC methods.

Figure 20:
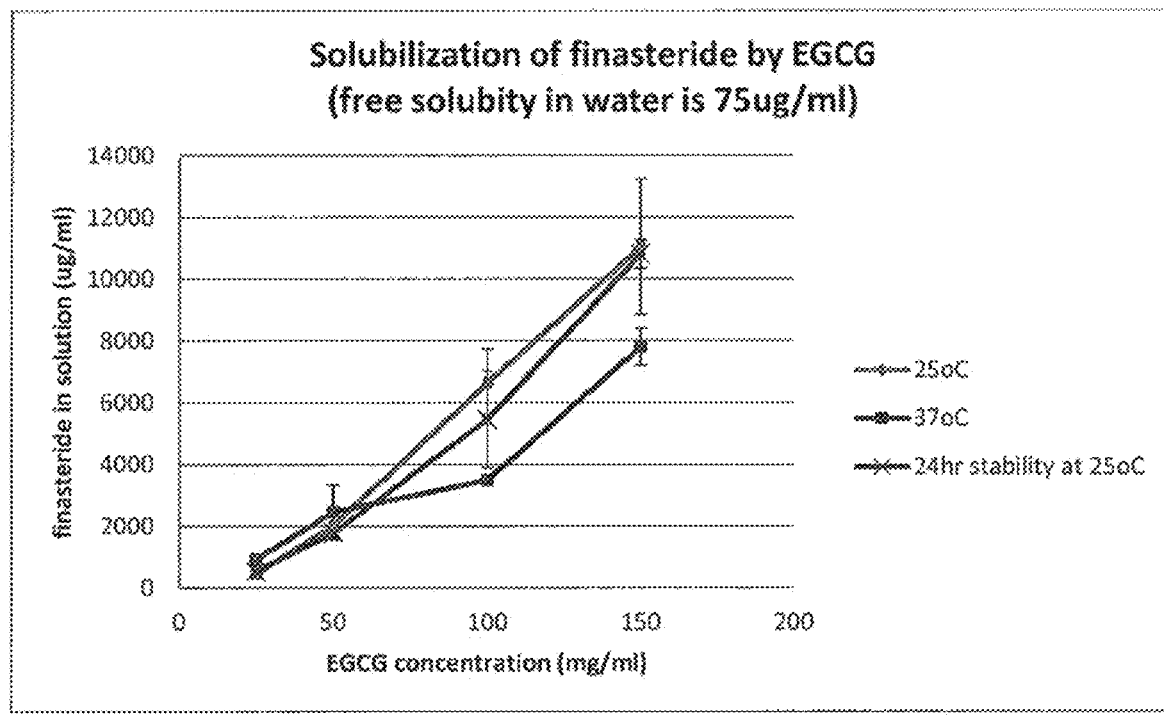
FIG. 20 is a graph showing the solubilization of finasteride by EGCG.
Figure 21:
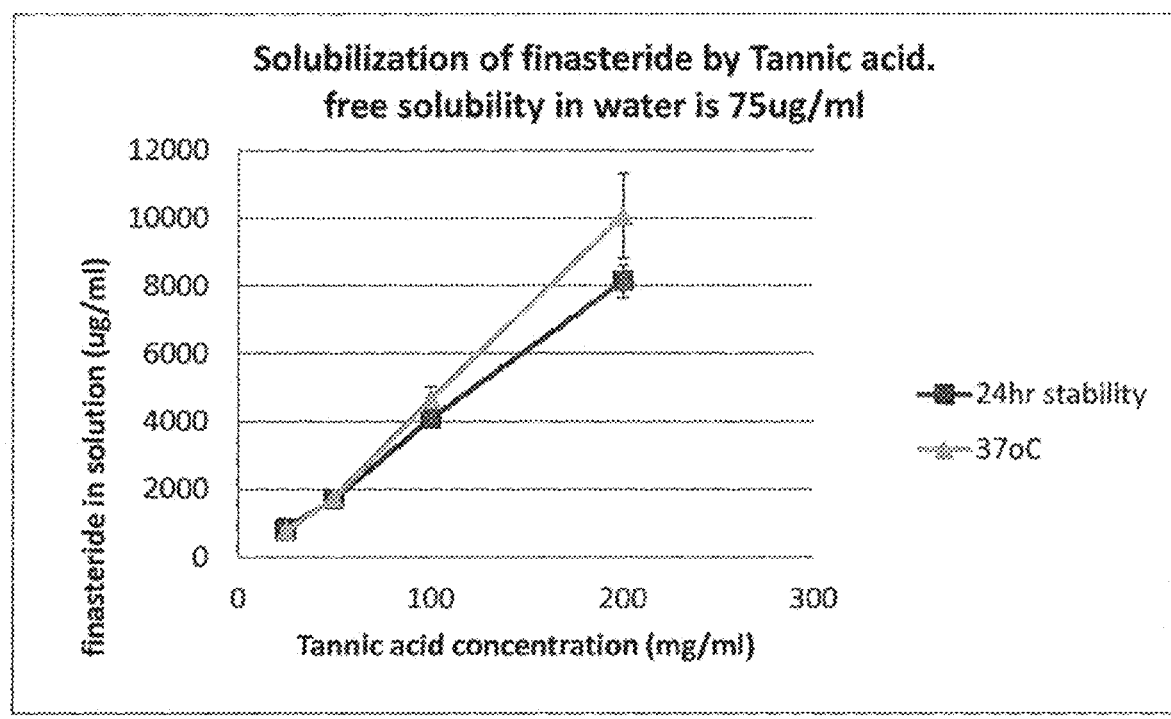
FIG. 21 is a graph showing the solubilization of finasteride by tannic acid.

Results: EGCG solubilised finasteride up to maximum concentrations of 150 mg per ml EGCG with drug at approx. 11000 microg/ml and solutions were stable for 24 hours (FIG. 20). Tannic acid solubilised finasteride up to maximum concentrations of tannic acid at 200 mg/ml EGCG with drug at approximately 10000 microgram/ml (FIG. 21). All solutions were stable for 24 hours and were temperature insensitive.

Example 25. The Uptake of Docetaxel or Paclitaxel into Pig Bladder Tissue Using Solutions with EGCG or Tannic Acid as Carriers Methods: Fresh ex vivo pig bladders were cut into 2 cm diameter pieces and laid on franz diffusions cells. Tritium labeled docetaxel or paclitaxel solutions were manufactured by dissolving EGCG or tannic acid and drug along with a small volume of tritium labelled drug (Moravek CA, 1 microCi/microl) in ethanol and drying down. Alternatively, docetaxel or paclitaxel was made up to the same drug solution strength by dilution of the commercial formulations of the drug (tween 80 for docetaxel and cremophor for paclitaxel). The solutions were then made up in tyrodes buffer pH 7.4 and 400 ul was placed on the urothelial side of the tissue for 2 hours. The tissues were then frozen and cryosectioned for radioactivity counting by liquid scintillation methods.

Figure 22A:
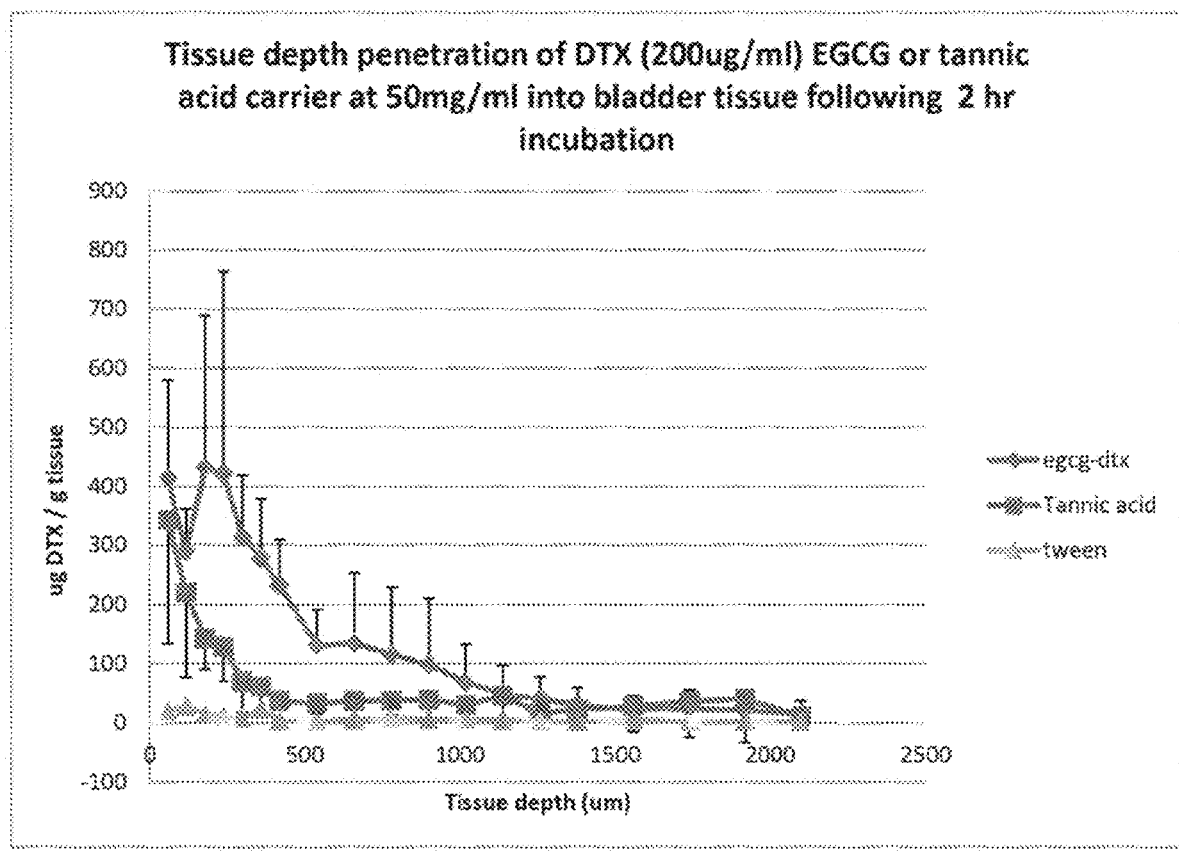
FIGS. 22(A)-(B) are graphs showing the uptake of docetaxel FIG. 22(A) or paclitaxel FIG. 22(B) into pigs bladder tissue following incubation with EGCG or tannic acid solutions of the drugs.
Figure 22B:
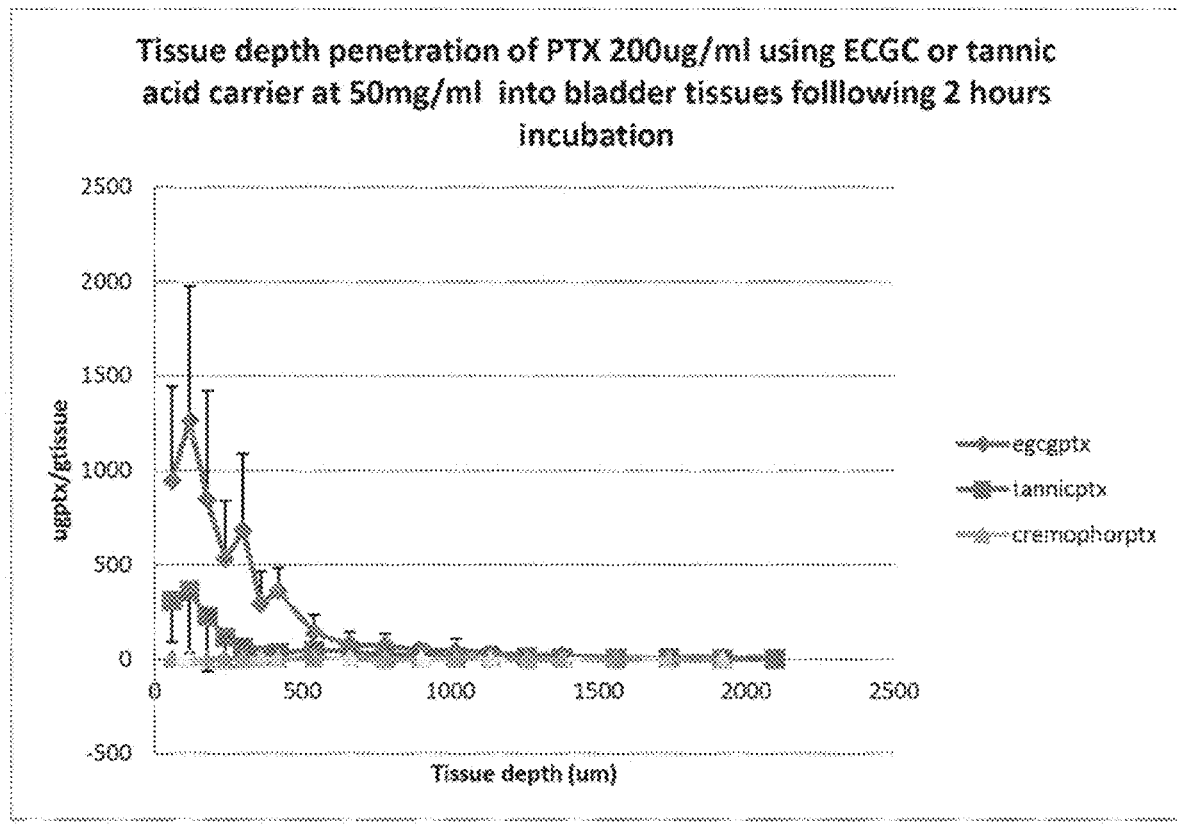

Results: Experiment 1: Using docetaxel or paclitaxel at 200 microg/ml in either EGCG or tannic acid at 50 mg/ml allowed for high levels of drug penetration through bladder tissue as shown in FIGS. 22 A and 22 B respectively. The levels of drug penetration far exceeded those achieved using either tween or cremophor formulations of the drugs.

Using EGCG or tannic acid as drug carriers allows for high levels of drug penetration into the bladder tissues.

Example 26. The Uptake of Paclitaxel into Pig Bladder Tissue Using EGCG or Tannic Acid in Methoxypolyethylene Glycol Pastes Methods: Fresh ex vivo pig bladders were cut into 2 cm diameter pieces and laid on franz diffusions cells. Tritium labeled paclitaxel loaded polymeric pastes were manufactured containing 57% methoxypolyethylene glycol (MEPEG 350, Union Carbide), 38% tannic acid or egcg and 5% by weight drug with 10 ul of 3H (tritium) labelled drug (1 uCi/ul) by dissolution in a small volume of ethanol and dried with blending. 100 mg of paste was applied to either the perivascular or urothelial side of the bladder tissue and 200 ul of tyrodes buffer pH 7.4 was added. The tissue was incubated for 2 hours at 37° C. and then the diffusion cell was disassembled, the tissue was washed free of remaining paste with excess tyrodes and the tissues were then frozen and cryosectioned for radioactivity counting by liquid scintillation methods.

Figure 23:
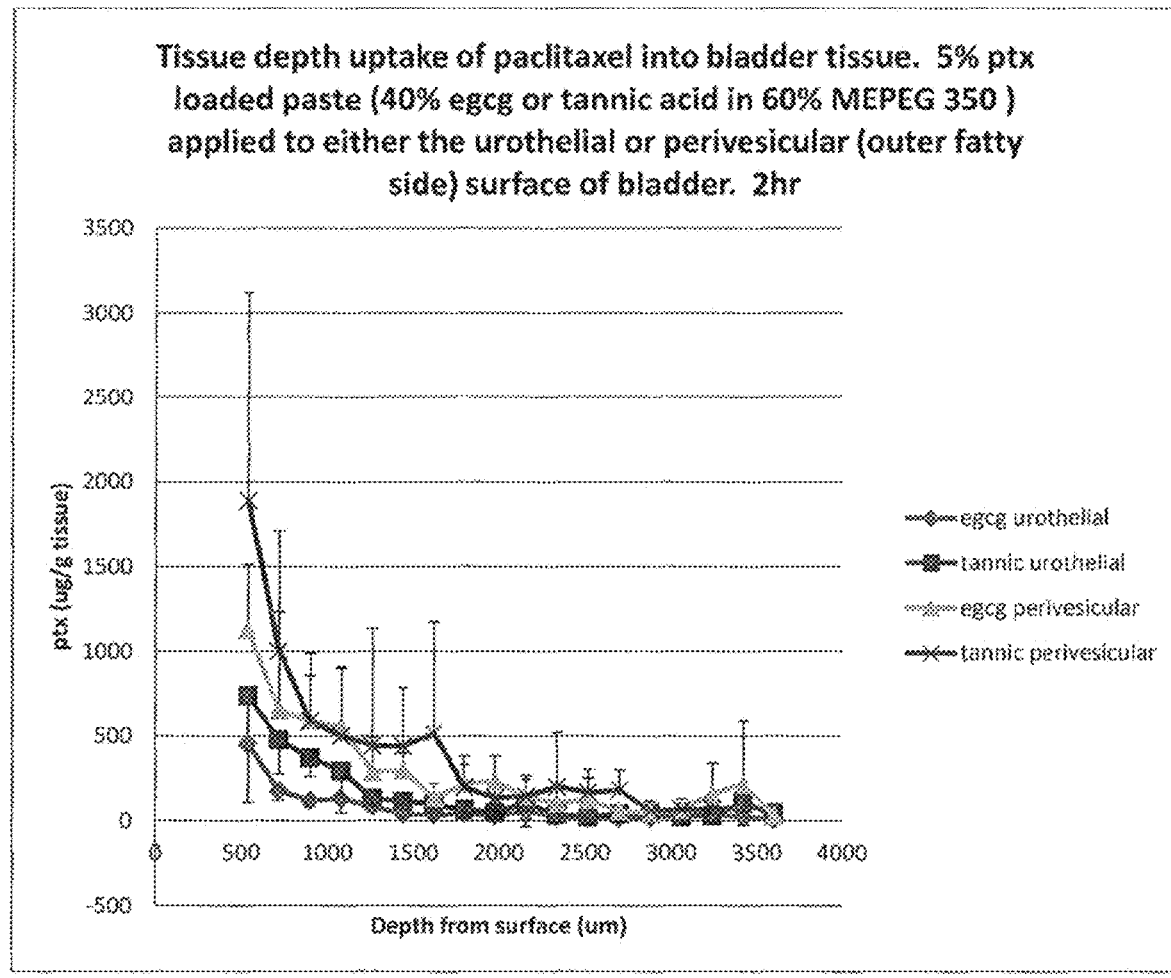
FIG. 23 is a graph showing the uptake of paclitaxel into bladder tissue following incubation with a paste formulation composed of methoxypolyethylene glycol with EGCG or tannic acid on either the urothelial or perivesicular surfaces of the bladder tissue.

Results: Both EGCG and tannic acid loaded formulations allowed for the penetration of paclitaxel into the bladder tissue when applied on either the urothelail or perivascular sides of the bladder wall as shown in FIG. 23. The data is shown as distance from the respective applied surface so that urothelail data reflects the tissue depth profile from the urothelial surface through to the outer fatty layer (perivesicular surface) and the perivesicular data runs in the reverse direction Example 27. The Uptake of Paclitaxel or Docetaxel into Pigs Bladder Tissue Using EGCG or Tannic Acid in a Triblock Copolymer or a Diblock Copolymer-Methoxypolyethylene Glycol Paste Application to the Perivesicular Surface Methods: Fresh ex vivo pigs bladders were cut into 2 cm diameter pieces and laid on franz diffusions cells. Tritium labeled paclitaxel or docetaxel loaded polymeric pastes were manufactured containing 45% methoxypolyethylene glycol (MEPEG 350, Union Carbide), 30% triblock copolymer or diblock copolymer with either tannic acid or egcg at 25% and 5% by weight drug with 10 microl of $^3$H (tritium) labelled drug (1 microCi/microl) by dissolution in a small volume of ethanol and dried with blending. The synthesis of the diblock copolymer is described in example X and is composed of a MEPEG molecule of 2000 molecular weight with polylactic acid at a molecular weight of 1330. The triblock copolymer was synthesized in house and has a composition of 35/35/30 (polycaprolactone, polylactic acid, polyethylene glycol with a total molecular weight of 4600. The triblock was synthesized by heating a mixture of caprolactone (Sigma chemicals) lactic acid (Polysciences) and Polyethylene glycol (Sigma molecular weight 1380) to 120° C. under nitrogen overnight followed by cooling and washing in hexane or cold ethanol. 100 mg of paste was applied to the perivascular side of the bladder tissue and 200 ul of tyrodes buffer pH 7.4 was added. The tissue was incubated for 2 hours at 37° C. and then the diffusion cell was disassembled, the tissue was washed free of remaining paste with excess tyrodes and the tissues were then frozen and cryosectioned for radioactivity counting by liquid scintillation methods.

Figure 24:
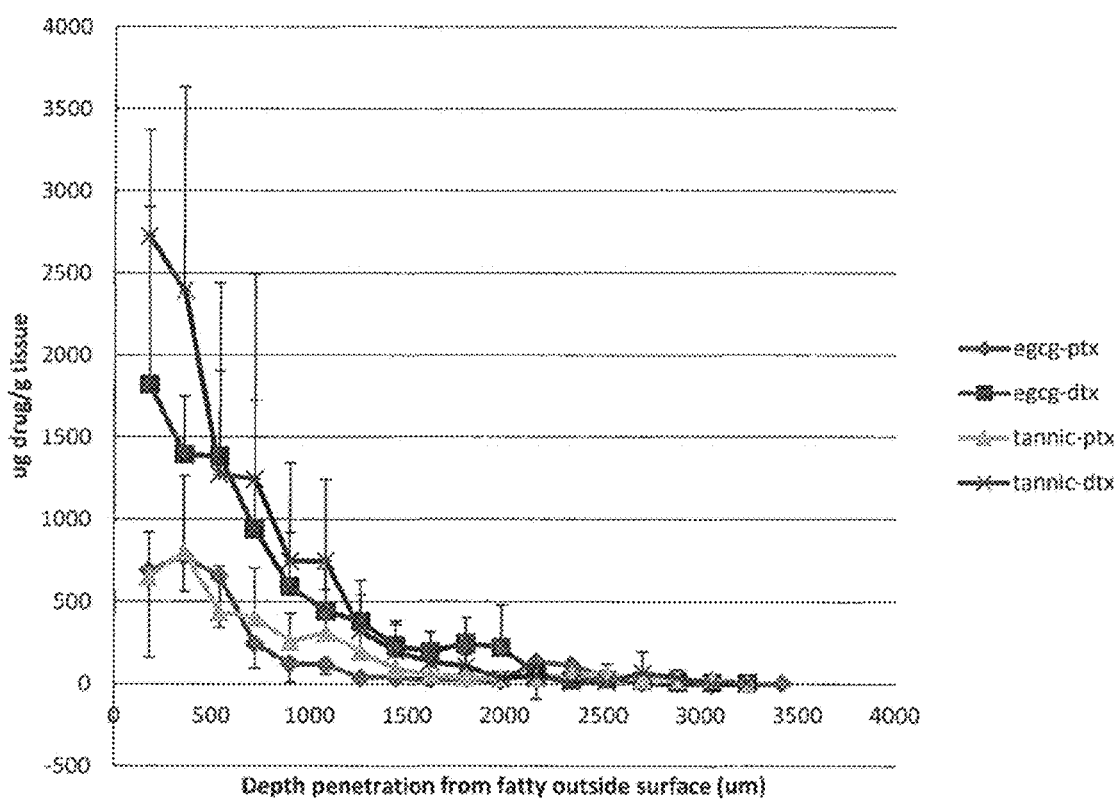
FIG. 24 is a graph showing the uptake of paclitaxel or docetaxel into bladder tissue following perivesicular application of a paste containing EGCG or tannic acid in a triblock copolymer with methoxypolyethylene glycol.
Figure 25:
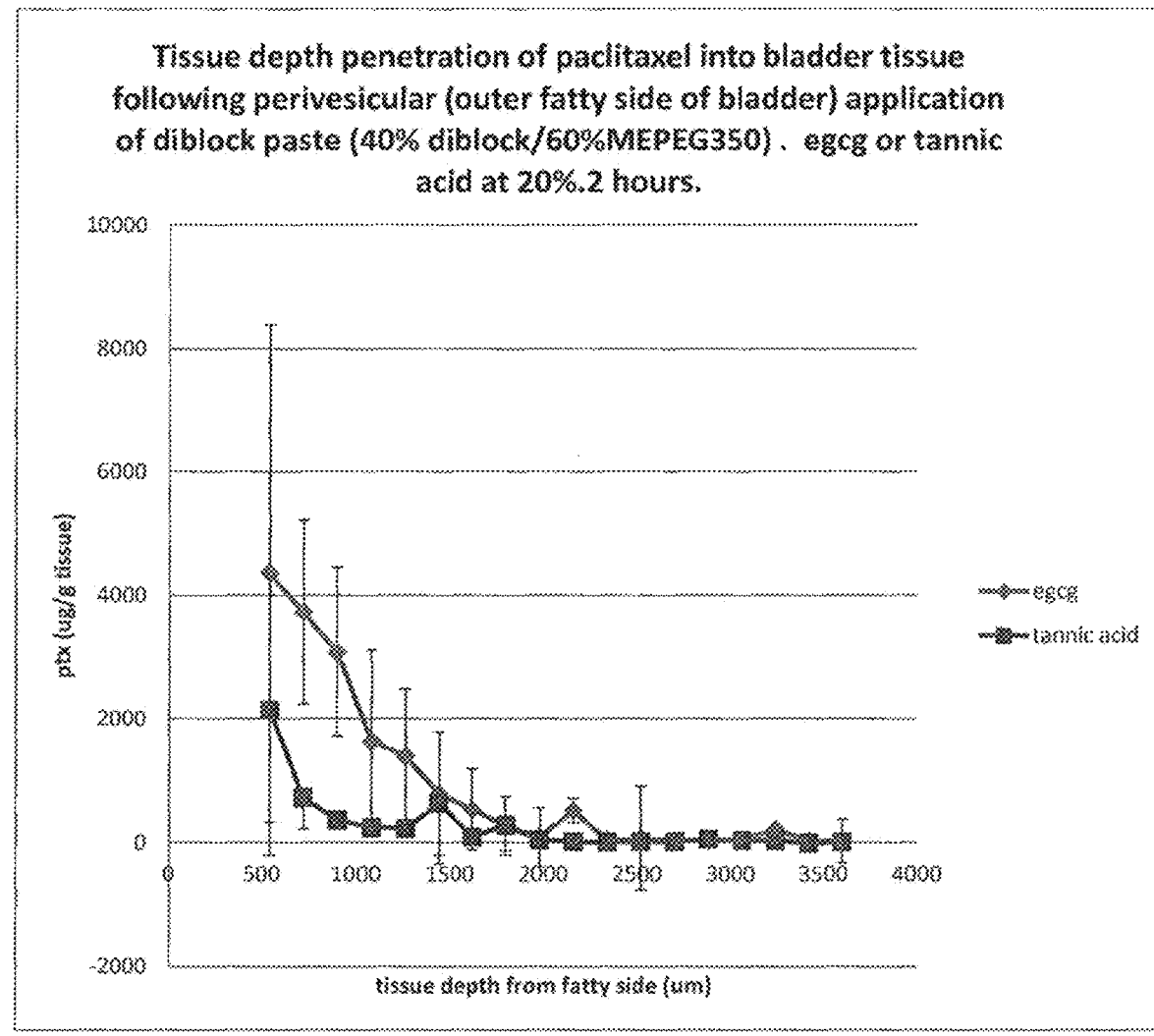
FIG. 25 is a graph showing the uptake of paclitaxel or into bladder tissue following perivesicular application of a paste containing EGCG or tannic acid in a diblock copolymer with methoxypolyethylene glycol.

Results: Both EGCG and tannic acid loaded triblock copolymer formulations allowed for the penetration of both paclitaxel and docetaxel into the bladder tissue when applied on perivesicualr sides of the bladder wall. The data is shown in FIG. 24 as distance from the applied surface to the urothelial side. Both EGCG and Tannic acid loaded diblock copolymer pastes allowed for the penetration of paclitaxel into the bladder wall when applied onto the perivesicular side of the bladder wall as shown in FIG. 25.

Example 28. Methods and Formulations for Dermal Drug Delivery

Various gallate-containing drug formulations were prepared and applied to ex vivo pig skin samples. Fresh pig skin was obtained from a local butcher, processed within three hours and then frozen. For experiments, the skin was slowly thawed, excess fat removed from the base, and cut into 1×2 cm squares. These squares were mounted and clamped on Franz diffusion cells, which kept the tissue moist and isolated and exposed a 6 mm diameter of the upper skin surface for the application of a drug loaded formulation. Skin samples were then frozen and later cryosectioned in 50 μm slices. The drug in the slices was extracted and measured by HPLC or radioactive doping methods. A drug depth profile was then established for each drug. In all cases, high levels of drug penetration were found for gallate-containing drug formulations. These levels were higher than levels for non-gallate containing commercial control formulations.

Formulations were prepared based on seven drugs (paclitaxel, docetaxel, curcumin, retinoic acid, lidocaine, amphotericin B, and finasteride), as follows:

1. Formulations containing a drug and a gallate. The drugs were dissolved in ethanol at various concentrations along with either EGCG or TA (500 mg/mL). Each solution was pipetted into 6×5 mm diameter aluminum cups (approximately 3 mm in height) by filling and allowing the ethanol to evaporate at 50° C. until all the solution was used up (80 mg per cup).

2. Formulations containing a drug, propylene glycol ("PG") and a gallate. 300 mg of propylene glycol was mixed with 200 mg of EGCG or TA until dissolved. Various amounts of drug were added to this mixture and dissolved. 80 mg of the resulting viscous solution was weighed into 6×5 mm aluminum cups.

3. Control Formulations. Control formulations were prepared using Glaxal base and Plogel. Glaxal base is a cream used by compounding pharmacists to manufacture topical formulations of drugs. Plogel is an alternative used for dermal formulations. Plogel formulations were supplemented with labrasol (50%), which is a penetration enhancer. Drug was added to a known weight of Glaxal or Plogel and levigated to produce a standard drug dispersion. These formulations were prepared the evening before the experiment. For some drugs, radioactive drug (where available) was also added as a doping additive to facilitate quantitation in tissues.

Eutectics: In some cases, gallate containing compounds and drugs were formulated in eutectic mixtures. These included a 60:40 (% w/w) mixture of menthol with ibuprofen. These agents acted as a carrier for retinoic acid, which was then dissolved in this liquid. The 3-drug eutectic/solution was then blended into the CMC/poloxamer emulsion containing EGCG (2.5%). Another eutectic system used a 50:50 (% w/w) mixture of lidocaine with menthol blended into a carboxymethyl cellulose gel containing 2.5% w/w EGCG. The emulsion was stabilized with poloxamer.

Example 29. Pig Skin Studies

Aluminum cups containing drug formulations were inverted on top of the pig skin in the Franz diffusion cell so that the formulation contents were in contact with the skin. 80 mg of Glaxal/drug or Plogel/drug mixture were added to control skin surfaces. 50 µL of Tyrode's physiological buffer at pH 7.4 was added to the top chamber with the formulation and the base of the cell was also filled with the same buffer solution.

The top chambers were capped (to keep the skin surface moist) and the cells were incubated in the dark at 37° C. in a humid incubator for six hours. The cells were then dismantled sequentially and the 6 mm center piece of the skin was excised with scissors and flash frozen (liquid nitrogen) with the skin surface flat on a metal plate. The samples were then stored at −80° C. until use. Six skin samples were prepared per formulation.

For most qualitative experiments, the paste consisted of 60% PG with 40% EGCG or TA. Various amounts of drug were suspended into these pastes to study drug dissolution. For lidocaine, pastes were made using 50:50 (PG:gallate), 60:40, 70:30 or 80:20 (% w/w) and contained 5, 10, 15 or 20% of lidocaine (w/wl to paste) fully dissolved in these pastes.

Analysis. Frozen skin sections were mounted in a cryotome with the flat skin surface facing the cutting blade. For all drugs, the samples were then cut in 50 µm thick pieces and pooled into groups of sections for drug extraction. Skin samples were then weighed and soaked in 300 µL of acetonitrile to extract drugs (for amphotericin B a 50:50 mixture of methanol and acetonitrile was used). The amount of drug in each group of skin sections was then determined using HPLC methods, or by radioactivity counting on a liquid scintillation counter. The amount of drug in each group of skin sections was expressed as pg/g or mg/g of tissue.

Example 30

Figure 26:
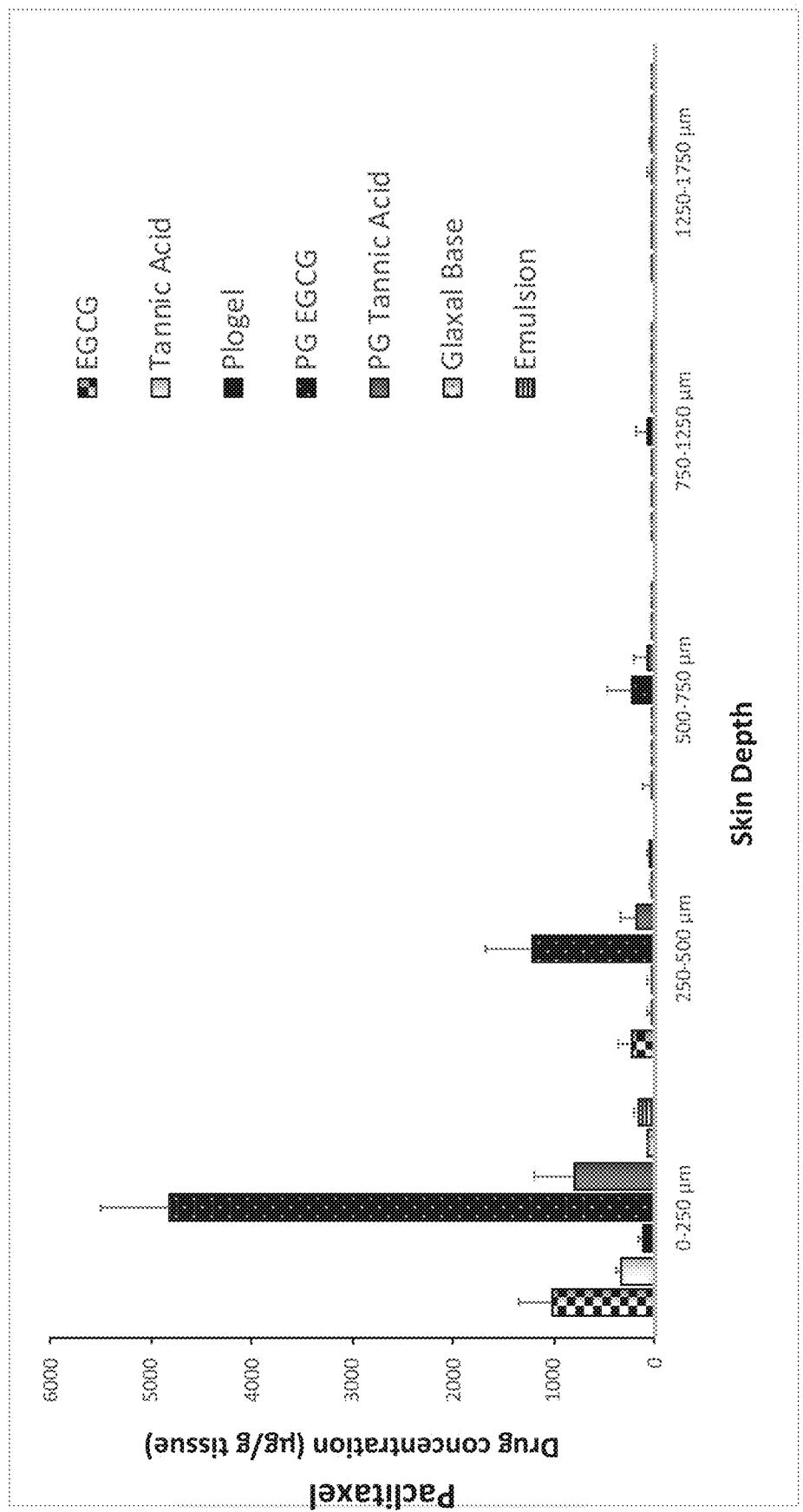
FIG. 26 is a graph showing uptake of paclitaxel by pig skin after six hours of incubation using different formulations containing paclitaxel (ptx) at 0.6% w/w. The zero mark on the x-axis represents the skin surface origin (0) so deeper cuts are shown to the right along the x axis. The following are illustrated: 1—EGCG; 2—Tannic Acid; 3—Plogel; 4—PG/ECGC; 5—PG/Tannic Acid; 6—Glaxal Base; and 7—Emulsion.

Results: Drug penetration into pig skin.
1. Paclitaxel—FIG. 26 shows the uptake of paclitaxel by pig skin after six hours of incubation using different formulations containing paclitaxel (ptx) at 0.6% w/w. The zero mark on the x-axis represents the skin surface origin (0), and deeper cuts go to the right on the x axis.

As shown in FIG. 26, the control formulations (Glaxal and Plogel, without a gallate compound) exhibited low levels of drug uptake. Formulations with EGCG and paclitaxel alone exhibited high levels of drug uptake (~1000 µg/g). Formulations with EGCG-Propylene glycol (PG) paste exhibited even higher levels (almost 5000 µg/g) of uptake. Formulations with tannic acid and paclitaxel alone, or with tannic acid in PG exhibited higher levels of uptake as compared to the control formulations (bar 5 on each graph), but lower than the EGCG based formulations (bar 4 on each graph). The data illustrates that EGCG-based formulations give some level of drug in the mid dermis layer (250-500 µm).

FIG. 26 also illustrates results for an emulsion formed by dissolving paclitaxel in a eutectic solution of 50:50 lidocaine and menthol (% w/w). In a first step, 5.5% of paclitaxel was dissolved in the eutectic. Then, in a second step the eutectic of paclitaxel was blended into an emulsion of carboxymethyl cellulose stabilized with poloxamer that also contained EGCG (final paclitaxel concentration was 0.6%). As seen in FIG. 26, the emulsion provided increased uptake of paclitaxel as compared to the control formulations, but less than the other EGCG or tannic based formulations.

Figure 27:
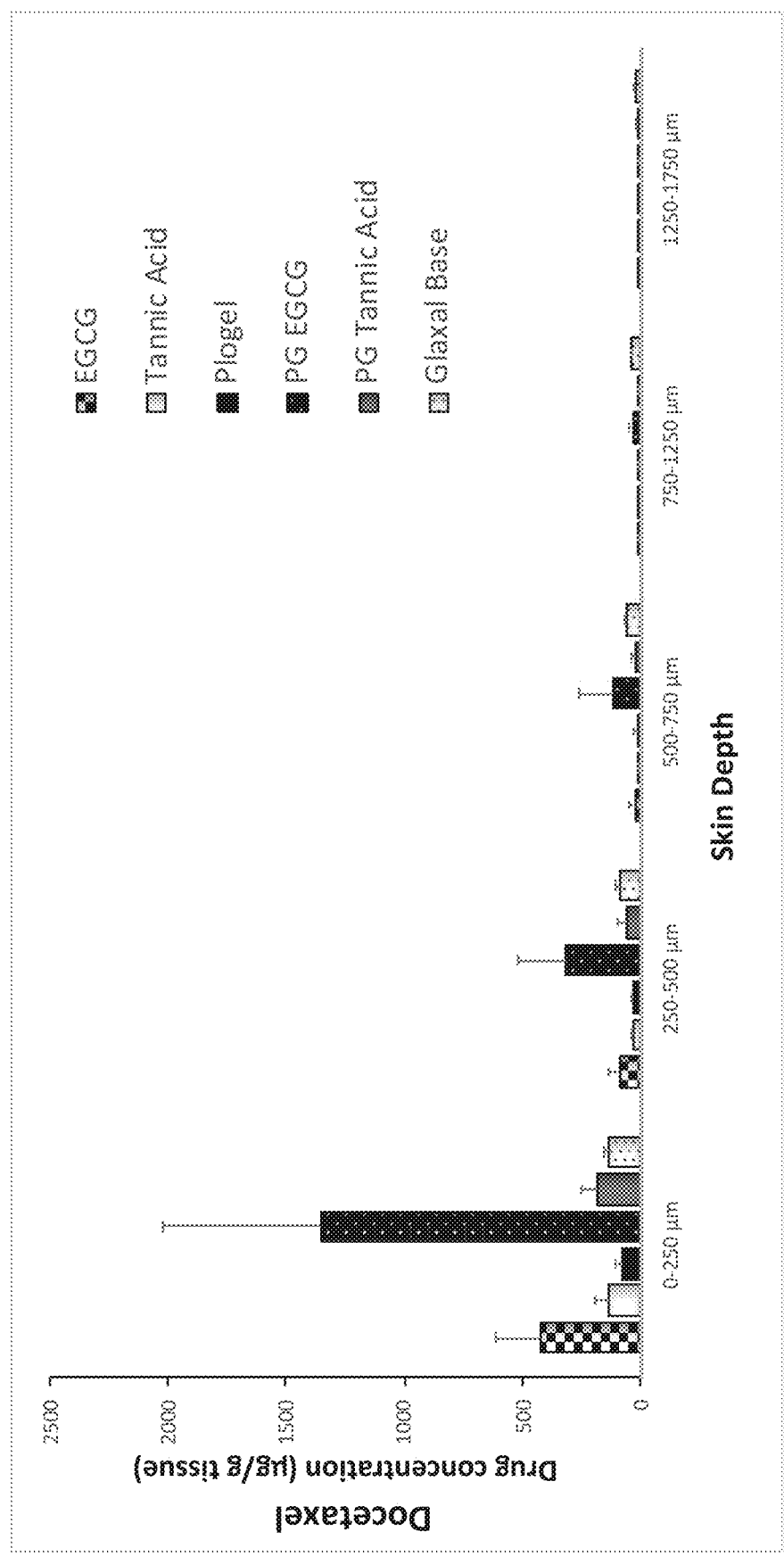
FIG. 27 is a graph showing uptake of docetaxel by pig skin after six hours of incubation using different formulations containing docetaxel (dtx) at 0.6% w/w. The origin (0) is the skin surface with deeper cuts going to the right on the x axis. The following are illustrated: 1—EGCG; 2—Tannic Acid; 3—Plogel; 4—PG/ECGC; 5—PG/Tannic Acid; and 6—Glaxal Base.

2. Docetaxel—FIG. 27 shows the uptake of docetaxel by pig skin after six hours of incubation using different formulations containing docetaxel at 0.6% w/w. The zero mark on the x-axis represents the skin surface origin (0), and deeper cuts go to the right on the x axis.

As shown in FIG. 27, the general order and intensity of drug uptake between the formulations is similar to those seen with paclitaxel. Formulations with EGCG and docetaxel alone exhibited high levels of drug uptake (over 400 µg/g). Formulations with EGCG-Propylene glycol (PG) paste exhibited even higher levels (over 1300 µg/g) of uptake. Formulations with tannic acid and docetaxel alone, or with tannic acid in PG exhibited higher levels of uptake as compared to the control formulations, but lower than the EGCG based formulations. Highest drug uptake was achieved using EGCG in a paste. In general, the uptake levels were higher for paclitaxel than for docetaxel.

There is a rule of thumb in the topical drug delivery field called the "500 Dalton rule." This rule predicts that only agents with a molecular weight smaller than 500 Dalton can penetrate the skin. The EGCG molecules have a molecular weight of 450 Da, and can pass through the skin. Paclitaxel and docetaxel, on the other hand, have molecular weights close to 900 Da and, based on the 500 Dalton rule, should not penetrate the skin. However, each of these drugs exhibited skin penetration when combined with EGCG or tannic acid.

Figure 28:
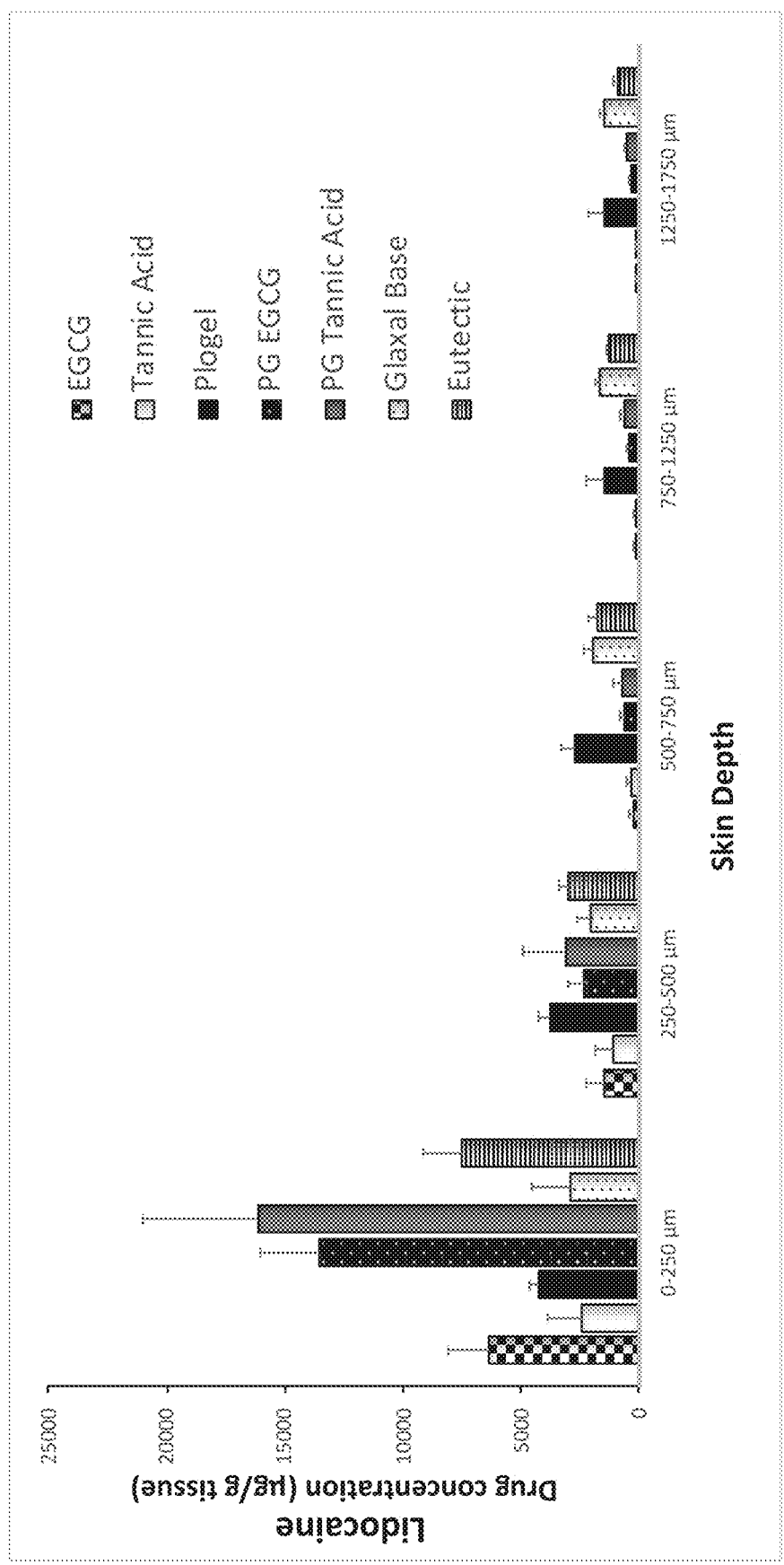
FIG. 28 is a graph showing uptake of lidocaine by pig skin after a six hour incubation using different formulations containing lidocaine at 4% w/w. The origin (0) is the skin surface with deeper cuts going to the right on the x axis. The following are illustrated, 1—EGCG; 2—Tannic Acid; 3—Plogel; 4—PG/ECGC; 5—PG/Tannic Acid; 6—Glaxal Base; and 7—Eutectic.

3. Lidocaine—FIG. 28 shows the uptake of lidocaine by pig skin after a six hour incubation using different formulations containing lidocaine at 4% w/w. The zero mark on the x-axis represents the skin surface origin (0), and deeper cuts go to the right on the x axis.

Lidocaine was taken up from each of the formulations, with levels of lidocaine persisting into the 250-500 µm deep mid-dermal layer. However, the EGCG, PG/EGCG, and PG/tannic acid formulations each exhibited higher levels of uptake in the 0-250 µm layer compared to the control formulations, with PG/EGCG exhibiting over 3 times higher uptake compared to the control formulations, and PG/tannic acid exhibiting nearly 4-5 times higher uptake compared to the control formulations.

FIG. 28 also illustrates results for a eutectic. This eutectic formulation of lidocaine showed higher uptake levels in the 0-250 µm layer than the two control formulations in Glaxal base and Plogel.

Figure 29:
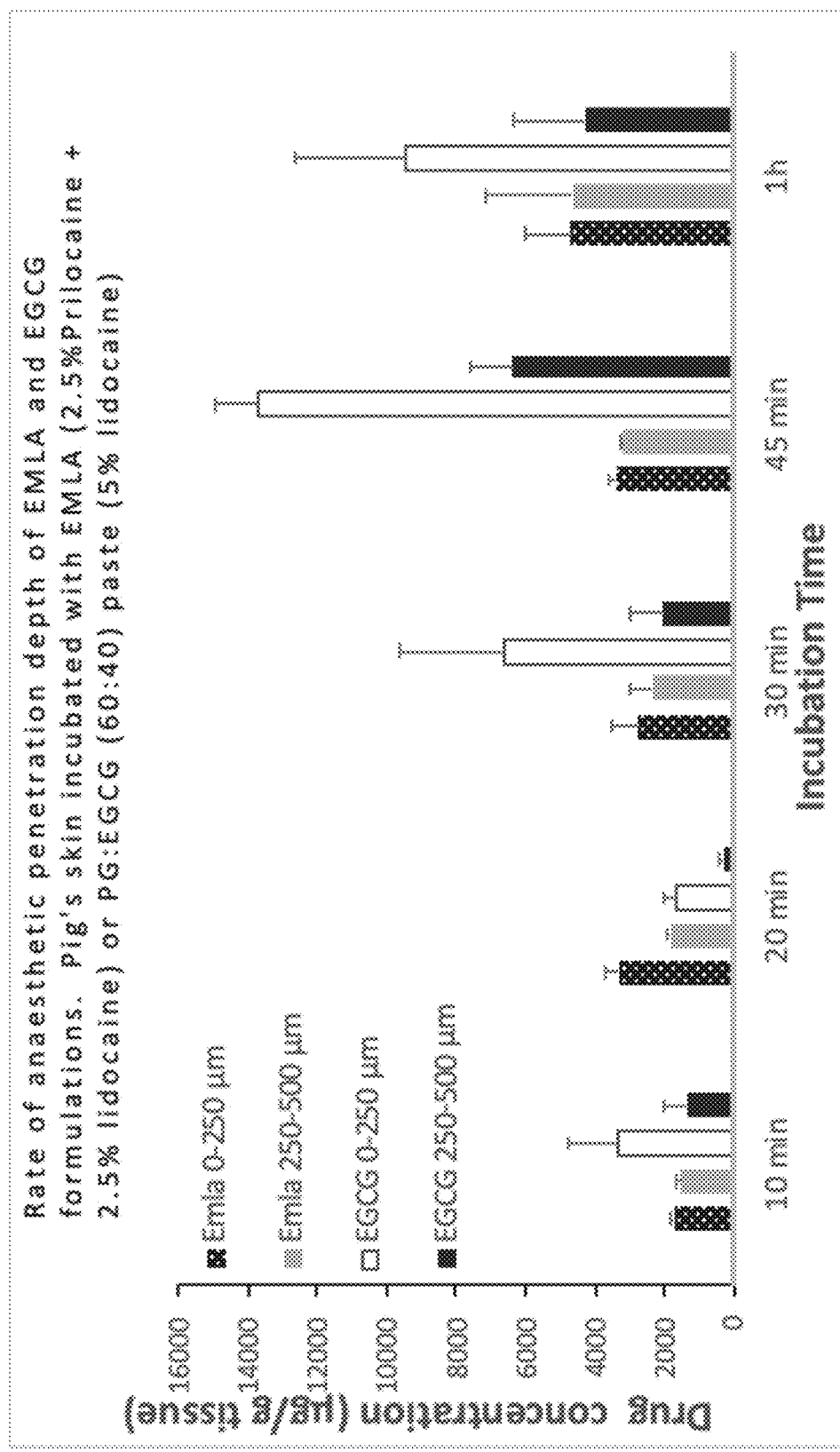
FIG. 29 is a graph showing the rate of anesthetic penetration depth of EMLA and EGCG formulations. Here, pig skin is incubated with EMLA (2.5% Prilocaine and 2.5% lidocaine) or PG:EGCG (60:40) paste containing 5% lidocaine. The following are illustrated: 1) EMLA 0-250 µm; 2) EMLA 250-500 µm; 3) EGCG 0-250 µm; and 4) EGCG 250-500 µm.

FIG. 29 shows the rate of uptake of lidocaine from PG:EGCG paste compared to lidocaine from a EMLA commercial cream. EMLA is an acronym for "Eutectic mixture of liquid anesthetics." EMLA is an anesthetic cream comprising 5% drug, a eutectic mixture (two solids together form a liquid with a lower melting point than either of the solids alone) of prilocaine and lidocaine in a cream emulsion.

Franz diffusion cells were set up as described previously, but incubation times were shorter at 10, 20, 30, 45, or 60 minutes. Skin sections of 25 µm were cut using acryostat in two groups of 10 to yield 0-250 µm depths and 250-500 µm depths respectively. Prilocaine and lidocaine were separated and quantified using an appropriate HPLC method.

As shown in FIG. 29, preliminary results indicate that EMLA and EGCG exhibit similar penetration rates over the first 20 minutes. However, EGCG exhibited similar or greater penetration than EMLA thereafter, at 30, 45 and 60 minutes, respectively.

Figure 30:
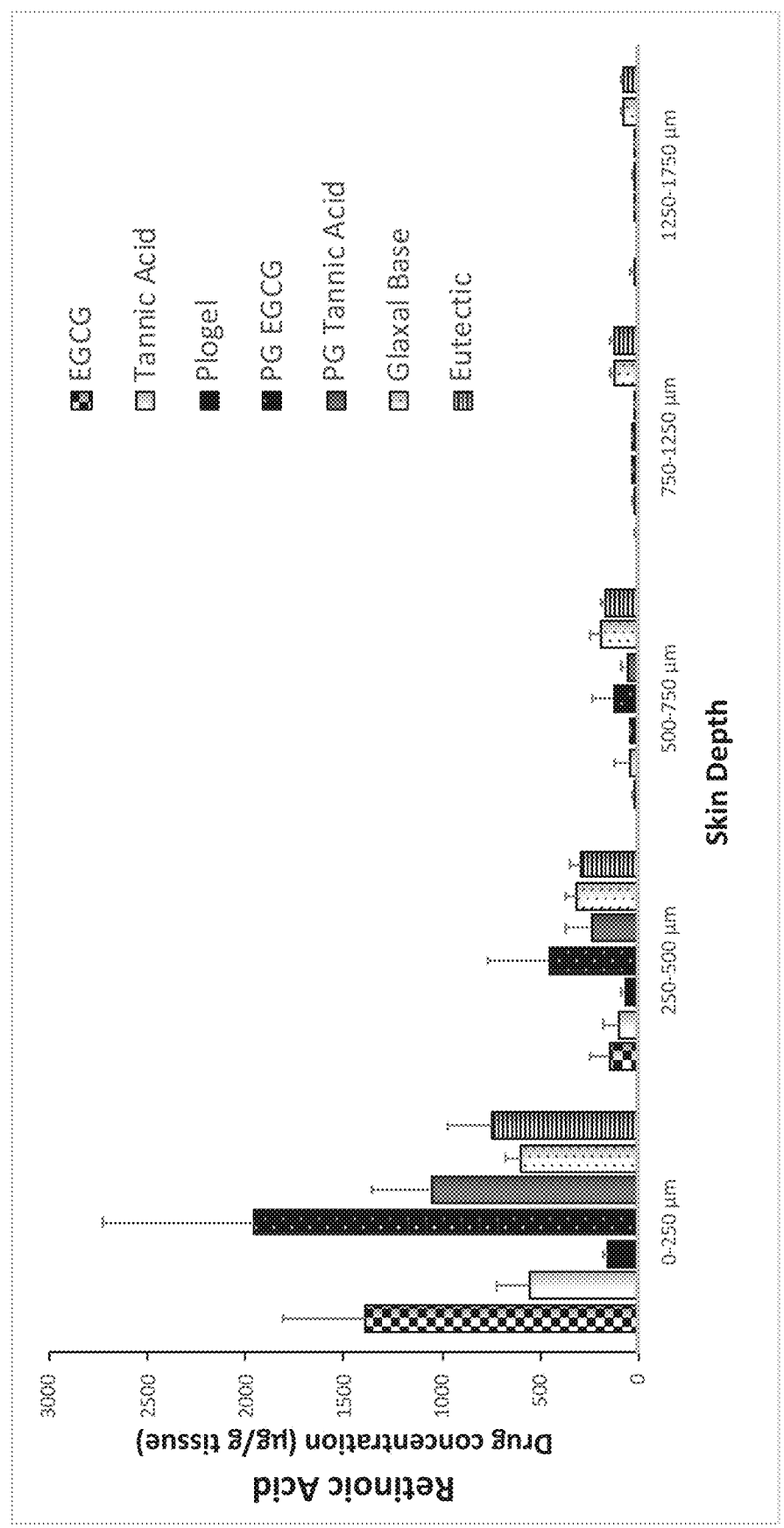
FIG. 30 is a graph showing uptake of retinoic acid by pig skin after a six hour incubation using different formulations containing retinoic acid at 0.6% w/w. The origin (0) is the skin surface with deeper cuts going to the right on the x axis. The following are illustrated: 1—EGCG; 2—Tannic Acid; 3—Plogel; 4—PG/ECGC; 5—PG/Tannic Acid; 6—Glaxal Base; and 7—Eutectic.

4. Retinoic acid—FIG. 30 shows the uptake of retinoic acid by pig skin after a six hour incubation using different formulations containing retinoic acid at 0.6% w/w. The zero mark on the x-axis represents the skin surface origin (0), and deeper cuts go to the right on the x axis.

As shown in FIG. 30, retinoic acid was taken up from each of the formulations, with EGCG, PG/EGCG, and PG/tannic acid formulations exhibiting higher uptake than the control formulations. Formulations with EGCG and retinoic acid alone exhibited high levels of drug uptake (~1400 µg/g). Formulations with EGCG-Propylene glycol (PG) paste exhibited even higher levels (~1900 µg/g) of uptake. In the 0-250 µm depth samples, formulations with tannic acid in PG exhibited higher levels of uptake as compared to the control formulations, but lower than the EGCG based formulations.

FIG. 30 also illustrates results for a eutectic. This eutectic exhibited similar or higher levels of drug uptake when compared to control formulations.

Figure 31:
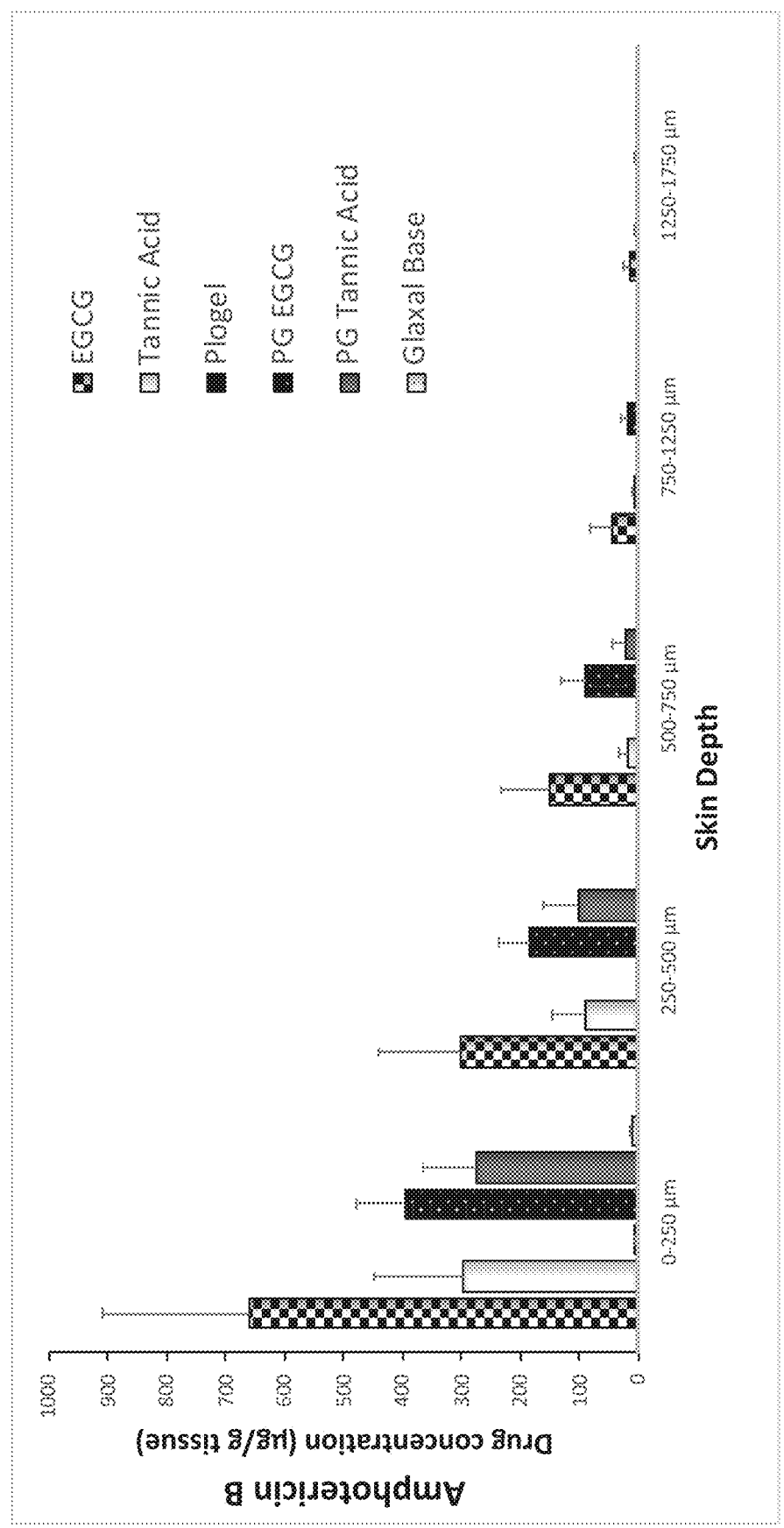
FIG. 31 is a graph showing uptake of amphotericin B by pig skin after a six hour incubation using different formulations containing amphotericin B at 0.6% w/w. The origin (0) is the skin surface with deeper cuts going to the right on the x axis. The following are illustrated: 1—EGCG; 2—Tannic Acid; 3—Plogel; 4—PG/ECGC; 5—PG/Tannic Acid; and 6—Glaxal Base.

5. Amphotericin B—FIG. 31 shows the uptake of amphotericin B by pig skin after a six hour incubation using different formulations containing amphotericin B at 0.6% w/w. The zero mark on the x-axis represents the skin surface origin (0), and deeper cuts go to the right on the x axis.

As shown in FIG. 31, EGCG and tannic acid based formulations of amphotericin B each exhibited higher drug uptake levels than either of the Plogel and Glaxal control formulations, with these control formulations exhibiting little to no uptake. Formulations with EGCG or tannic acid alone exhibited high levels of drug uptake (over 600 µg/g and ~300 µg/g, respectively). Formulations with EGCG-Propylene glycol (PG) or tannic acid-Propylene glycol paste exhibited somewhat lower levels of drug uptake (~400 µg/g and ~300 µg/g, respectively), but still significantly greater uptake than the control formulations. Although the non-PG containing formulations gave the highest level of uptake, the PG pastes nonetheless provide strong uptake compared to unsupplemented Glaxal Base and Plogel. For the mid-dermal regions (250-500 µm), the control formulations exhibited no drug penetration.

Figure 32:
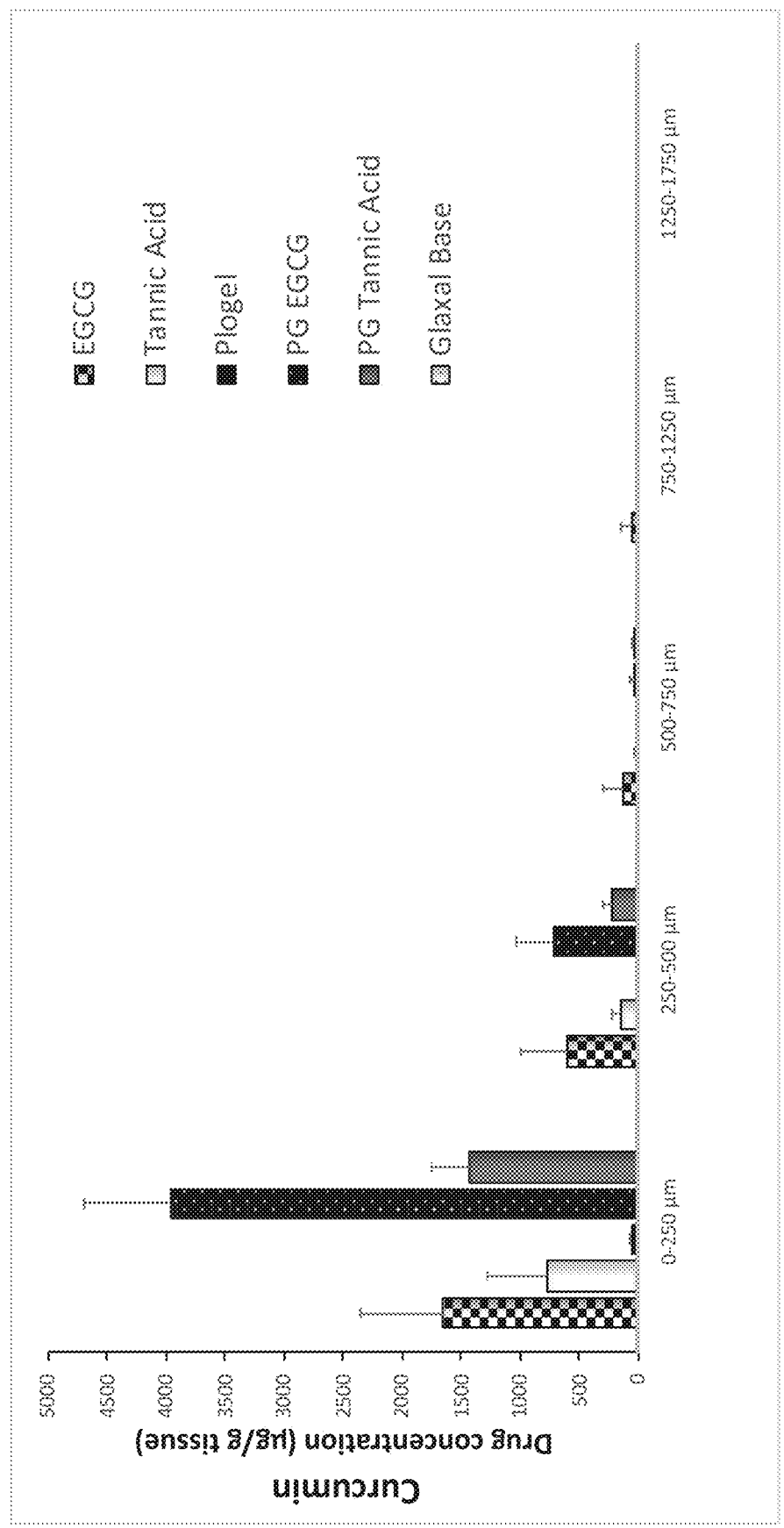
FIG. 32 is a graph showing uptake of curcumin by pig skin after a six hour incubation using different formulations containing curcumin at 0.6% w/w. The origin (0) is the skin surface with deeper cuts going to the right on the x axis. The following are illustrated: 1—EGCG; 2—Tannic Acid; 3—Plogel; 4—PG/ECGC; 5—PG/Tannic Acid; and 6—Glaxal Base.

6. Curcumin—FIG. 32 shows the uptake of curcumin by pig skin after a six hour incubation using different formulations containing curcumin at 0.6% w/w. The zero mark on the x-axis represents the skin surface origin (0), and deeper cuts go to the right on the x axis.

As shown in FIG. 32, Glaxal base and Plogel control formulations of curcumin exhibited essentially no drug uptake. EGCG and tannic acid based formulations, on the other hand, exhibited high uptake of the drug (EGCG (over 1600 µg/g); tannic acid (over 700 µg/g); EGCG/PG (~4000 µg/g); tannic acid/PG (~1400 µg/g). In general, ECGC based formulations provided higher uptake than tannic acid formulations, with PG/gallate formulations exhibiting higher uptake than the respective non-PG formulations.

Figure 33:
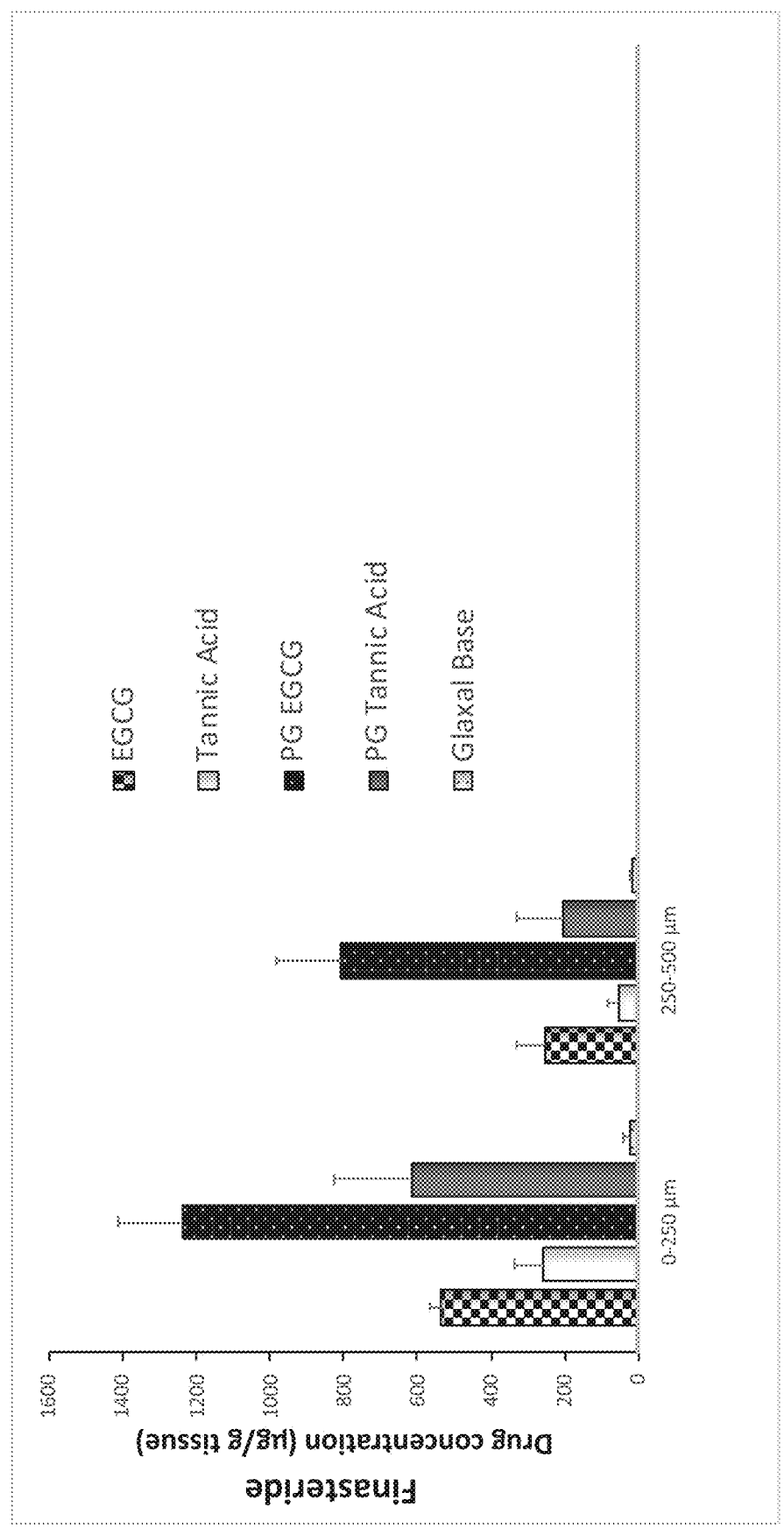
FIG. 33 is a graph showing uptake of Finasteride by pig skin after 6 hour incubation using different formulations containing finasteride at 0.25% w/w. The origin (0) is the skin surface with deeper cuts going to the right on the x axis. The following are illustrated: 1—EGCG; 2—Tannic Acid; 3—PG/ECGC; 4—PG/Tannic Acid; and 5—Glaxal Base.

7. Finasteride—FIG. 33 shows the uptake of Finasteride by pig skin after 6 hour incubation using different formulations containing finasteride at 0.25% w/w. The zero mark on the x-axis represents the skin surface origin (0), and deeper cuts go to the right on the x axis.

As shown in FIG. 33, the Glaxal base control paste exhibited low drug uptake. EGCG and tannic acid based formulations, on the other hand, exhibited high levels of drug uptake (EGCG (over 500 µg/g); tannic acid (over 250 µg/g); EGCG/PG (over 1200 µg/g); tannic acid/PG (over 600 µg/g). EGCG based formulations generally exhibited higher uptake levels than tannic acid based formulations. PG/gallate formulations were more effective than gallate drug formulations, again demonstrating the increased efficacy of gallate formulations as pastes.

Example 31. Injectable Gallate-Based Pastes

EGCG and tannic acid are fairly soluble in alcohol and acetonitrile. It was found that these agents were very soluble in propylene glycol and polyethylene glycol 300. Solubilities higher than 50% w/w were achievable for propylene glycol and 25% gallate:75% PEG using PEG 300. These solutions become more viscous and paste-like as the percentage of gallate in solution is increased. When non-drug containing pastes were placed in water, the contents of the paste (gallate, PG or PEG), which are all water soluble, dissolved away.

For injection, a paste composed of 50:50 w/w/, PG:gallate gives a rather viscous paste but at 60:40 and higher (PG) the paste is injectable through 21 gauge needles.

Figure 34:
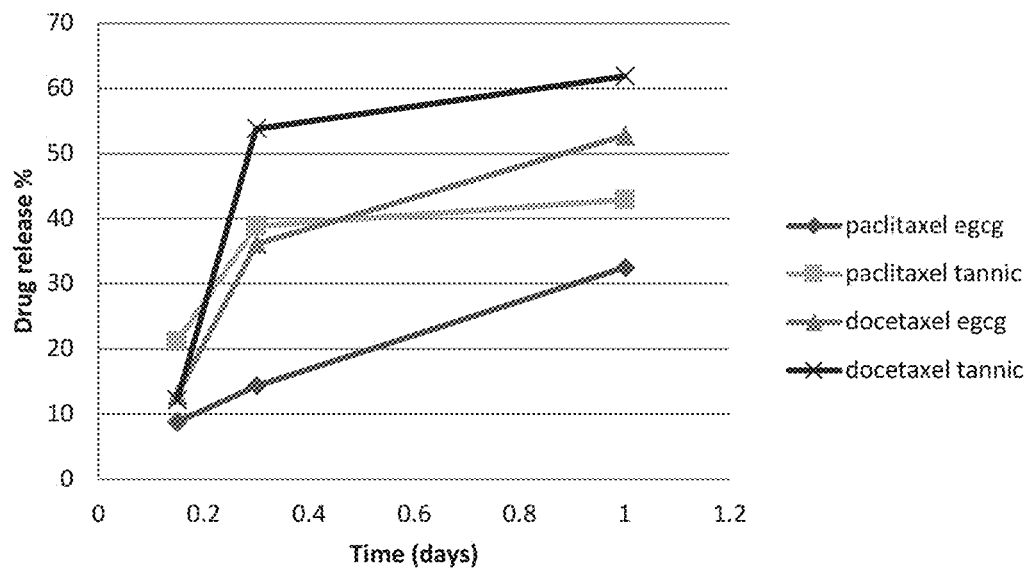
FIG. 34 is a graph showing release of paclitaxel or docetaxel from PG:gallate pastes (60:40) containing EGCG or tannic acid.
Figure 35:
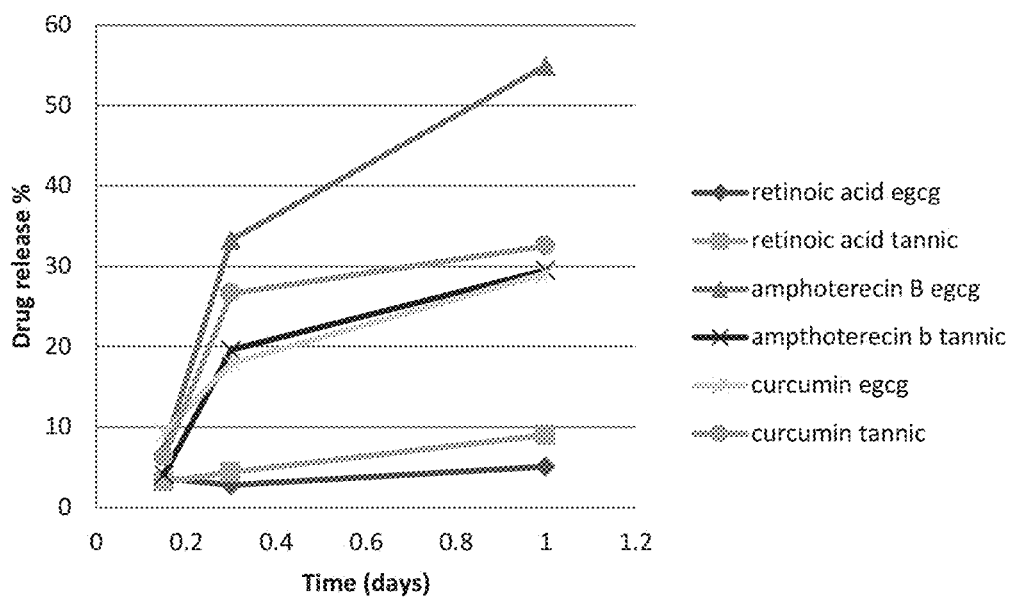
FIG. 35 is a graph showing release of retinoic acid, amphotericin B, or curcumin from PG:gallate pastes (60:40) containing EGCG or tannic acid.

Methods: 60:40% w/w PG:EGCG or PG:tannic acid was used in these studies. 588 mg of propylene glycol was weighed into a 20 mL glass vials and 392 of EGCG or tannic acid was added followed by vortexing to distribute and dissolve the gallates. The vials were warmed to 60° C. and vortexed until all the contents were in solution. At this time 20 mg of drug was added (2% w/w) and vortexed until in solution. The following drugs were used: paclitaxel, docetaxel, retinoic acid, amphotericin B, and curcumin. 100 mg of each paste was weighed into the base of a 15 mL glass test tube and 10 mL of phosphate buffered saline was added at pH 7.4 and the tubes were incubated at 37° C. for certain times. All 10 mL of the PBS release media was removed and 1 mL analyzed by HPLC for drug content. 10 mL of fresh PBS was then added to all tubes Results: At 2% drug loading, the paste in all tubes formed a gel-like mass when PBS was added but that mass broke up over 24 hours. Since these drugs were all hydrophobic in nature, there was a small solid mass left at 24 hours. FIG. 34 illustrates the results of a drug release study over 24 hours for paclitaxel and docetaxel (1%) from gallate pastes. FIG. 35 illustrates the result of a release study over 24 hours for retinoic acid, amphotericin B, and curcumin (1%) from gallate pastes.

The drugs paclitaxel, docetaxel, curcumin, retinoic acid and amphotericin B are potent drugs that normally are formulated at relatively low concentrations (e.g., 2%). The pastes described in this example are viscous, and can be injected into any tissue compartment, for example via catheter lines. These pastes provided relatively controlled release of the drug over 24 hours. This is highly advantageous over injecting a drug in a liquid solution, where the drug is immediately dispersed within the body and quickly cleared from the tissue. In one example, docetaxel may be injected directly into the prostate to deliver the drug accurately in one small location, as the paste stays intact for hours.

Example 32. Lidocaine Containing Gallate Paste: PEG300:Gallate Pastes

EGCG and tannic acid were found to be soluble in PEG 300 liquid at 25% w/w. When lidocaine was dissolved in this paste and the paste placed in PBS, there was a partial solidification of the paste, followed by a disintegration/dissolution over 3 days.

Example 33. Lidocaine Containing Gallate Paste:Propylene Glycol:Gallate Pastes

Surgery is associated with post-operative pain. This may range from severe acute pain at 24 hours, to acute pain for days, to subacute pain for many weeks, and may be followed by chronic pain lasting many months or up to a year. Pain over the first days or week is typically treated with systemically delivered drugs, such as oral analgesics (e.g., acetaminophen, NSAIDS, and opioids). These treatments have potential drawbacks, including the potential for addiction. It would be advantageous to have an injectable formulation that can be used to deliver an analgesic and/or anesthetic internally for the local treatment of pain, and preferably a formulation that releases the analgesic and/or anesthetic in a controlled manner over an extended period of time.

Method: Lidocaine pastes were formulated by dissolving various amounts of lidocaine (5, 10, 15 or 20% w/w) in various combinations of propylene glycol:EGCG or propylene glycol:tannic acid (60:40, 70:30, or 80:20). For each formulation, 100 mg of paste was placed in the base of a round bottomed 15 mL glass test tube. When viewed from the top (open tube) the paste mass had a diameter of approximately 8 mm. At the start of the release experiment, 10 ml of PBS was added and the tubes left for various time periods, after which all 10 mL of the release media was removed for drug analysis. The residual mass was observed from the top, and the drop in diameter from 8 mm noted as a semi-quantitative assessed of paste pellet degradation. It was not possible to measure the degradation fully quantitatively at that time, as the pellets were fragile and water-swollen. After a few days the pellets became less fragile, and were removed from the tubes and dried on tissue paper before weighing. The drop in weight from 100 mg was then noted as the % degradation and compared with the visual observations. In all cases these values matched to within 5% accuracy.

Figure 36A:
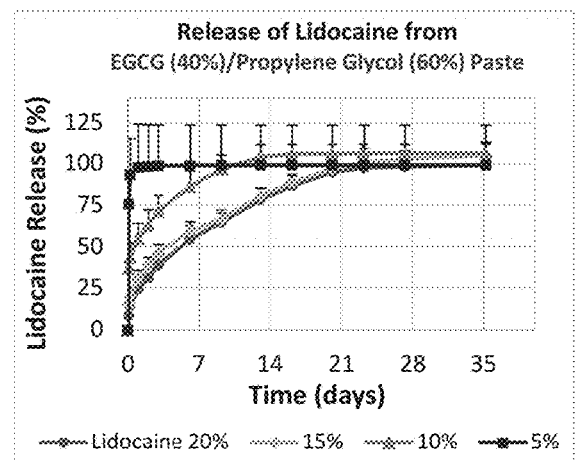
FIGS. 36(A)-(C) are graphs showing release of lidocaine (20%, 15%, 10%, or 5%) from EGCG:Propylene Glycol pastes. The following are illustrated: EGCG (40%)/Propylene Glycol (60%) paste (FIG. 36A); EGCG (30%)/Propylene Glycol (70%) paste (FIG. 36B); EGCG (20%)/Propylene Glycol (80%) paste (FIG. 36C).
Figure 36B:
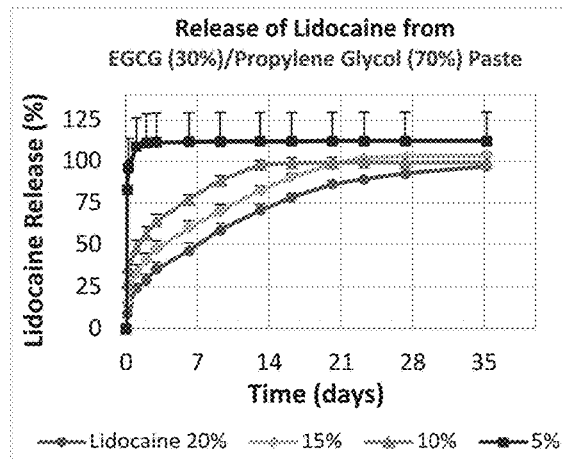
Figure 36C:
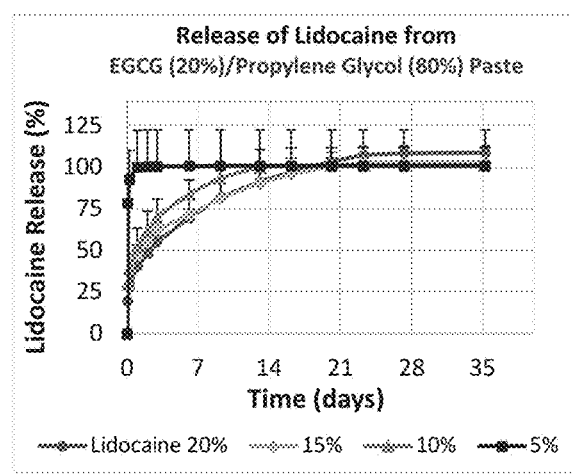

Results: FIGS. 36A-36C show the release of lidocaine from EGCG:propylene glycol pastes with various amounts of lidocaine (20%, 15%, 10%, and 5%), and at various ratios of EGCG:propylene glycol. At 5% drug loading, all EGCG pastes exhibited almost 100% drug release in approximately 2 days. Drug release was extended by increasing the drug loading to 10%, 15%, and 20%, respectively. At 20% drug loading, the EGCG pastes released drug over a period of between approximately 2-4 weeks. The order of release was generally affected by the PG % in the paste so that drug release was higher as follows: 80% PG>70% PG>60% PG.

Figure 37A:
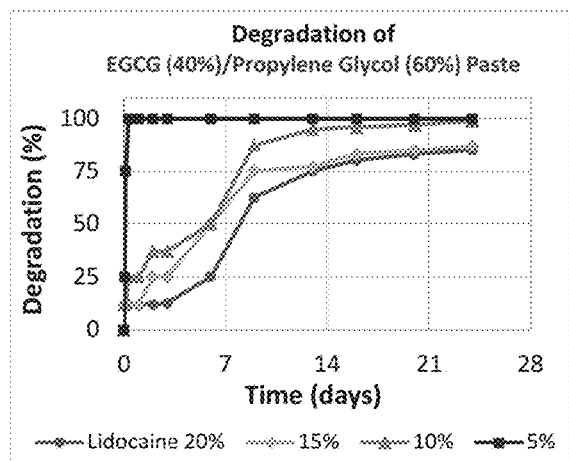
FIGS. 37(A)-(C) are graphs showing degradation of paste pellets including lidocaine (20%, 15%, 10%, or 5%) and EGCG:Propylene Glycol. The following are illustrated: EGCG (40%)/Propylene Glycol (60%) paste (FIG. 37A); EGCG (30%)/Propylene Glycol (70%) paste (FIG. 37B); EGCG (20%)/Propylene Glycol (80%) paste (FIG. 37C).
Figure 37B:
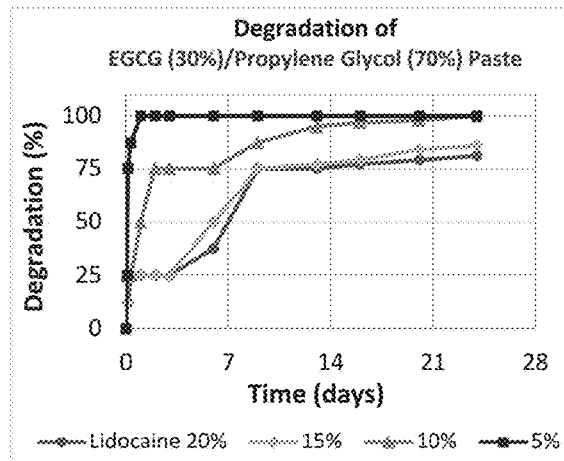
Figure 37C:
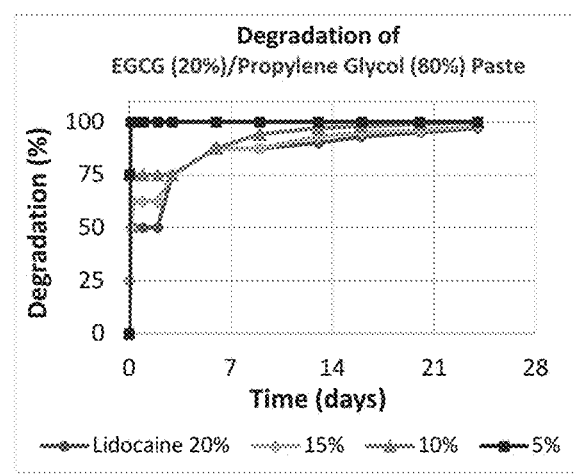

FIGS. 37A-37C show the degradation of the various lidocaine pastes reflected in FIGS. 36A-36C. The degradation curve profiles in FIGS. 37A-37C generally mirror the release profiles in FIGS. 36A-36C.

Figure 38A:
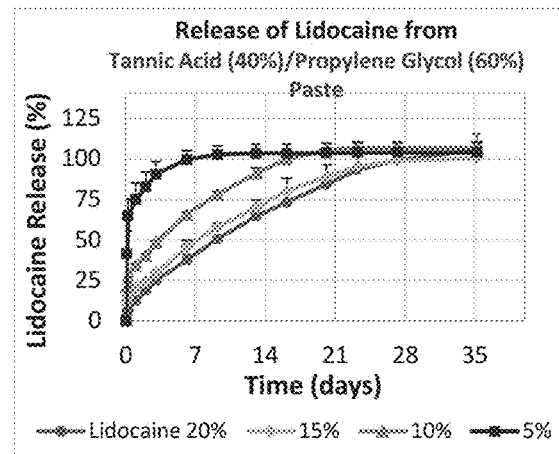
FIGS. 38(A)-(C) are graphs showing release of lidocaine (20%, 15%, 10%, or 5%) from Tannic Acid:Propylene Glycol pastes. The following are illustrated: Tannic Acid (40%)/Propylene Glycol (60%) paste (FIG. 38A); Tannic Acid (30%)/Propylene Glycol (70%) paste (FIG. 38B); Tannic Acid (20%)/Propylene Glycol (80%) paste (FIG. 38C).
Figure 38B:
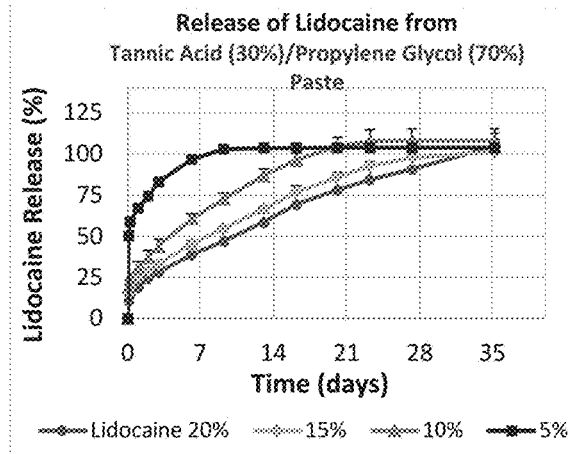
Figure 38C:
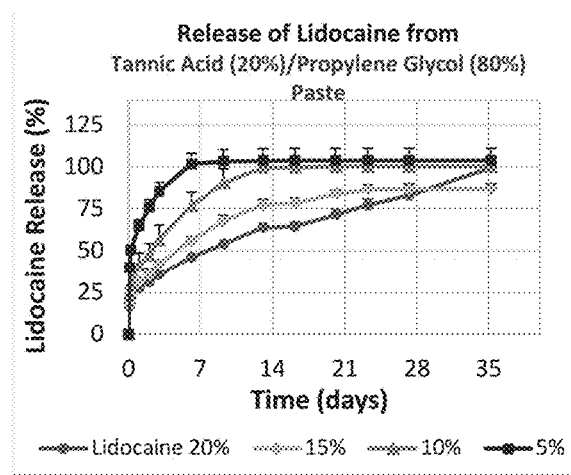

FIGS. 38A-38C show the release of lidocaine from tannic acid:propylene glycol pastes with various amounts of lidocaine (20%, 15%, 10%, and 5%), and at various ratios of tannic acid:propylene glycol. At 5% drug loading, each of the pastes released lidocaine over a period of almost 7 days (compared to EGCG formulations which released over approximately 2 days). Drug release was extended by increasing the drug loading to 10%, 15%, and 20%, respectively. At 20% drug loading, the tannic acid pastes released drug over a period of between approximately 4-5 weeks. The order of release was generally affected by the PG % in the paste so that drug release was higher as follows: 80% PG>70% PG>60% PG.

Figure 39A:
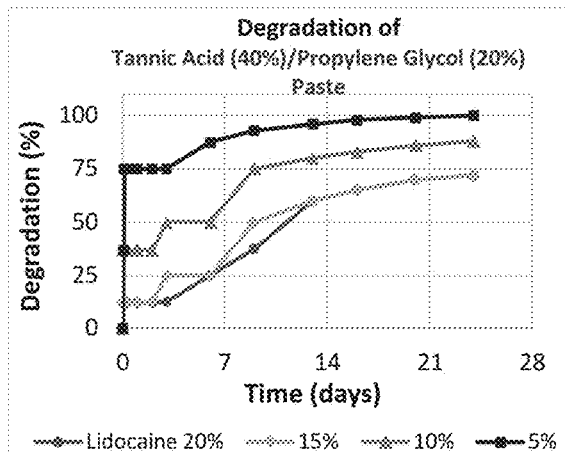
FIGS. 39(A)-(C) are graphs showing degradation of paste pellets including lidocaine (20%, 15%, 10%, or 5%) and Tannic Acid:Propylene Glycol. The following are illustrated: Tannic Acid (40%)/Propylene Glycol (60%) paste (FIG. 39A); Tannic Acid (30%)/Propylene Glycol paste (70%) (FIG. 38B); Tannic Acid (20%)/Propylene Glycol paste (80%) (FIG. 39C).
Figure 39B:
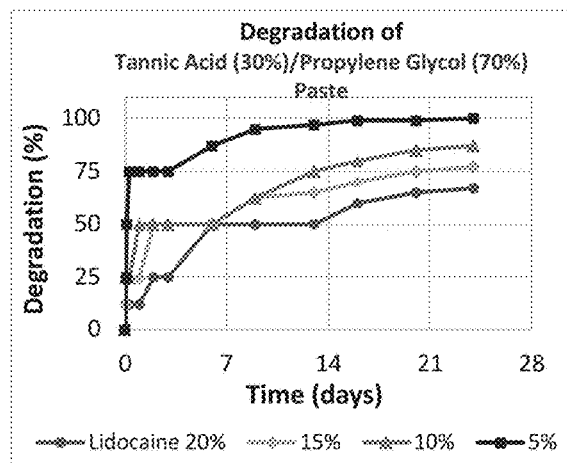
Figure 39C:
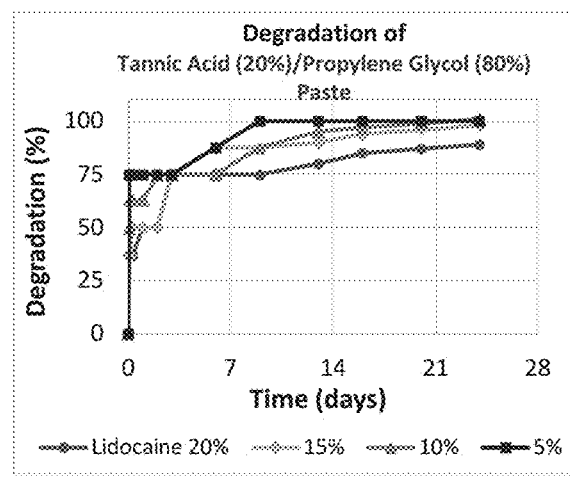

FIGS. 39A-39C show the degradation of the various lidocaine pastes reflected in FIGS. 38A-38C. The degradation curve profiles in FIGS. 39A-39C generally mirror the release profiles in FIGS. 38A-38C.

Formulations including lidocaine in PG:gallate pastes results in the creation of a partially water-insoluble waxy pellet on addition of aqueous media. For EGCG the complexation was weak using 5% drug loading in any paste. However, for 5% drug loading in tannic acid based pastes, the pellet lasted longer allowing controlled drug release over a period of a week. At higher drug loadings for both EGCG and tannic acid formulations, paste degradation and drug release rates slowed as the formulations resulted in more robust pellets. In addition, increasing drug loading created more linear drug release profiles. Increasing EGCG or tannic acid in the paste further slowed degradation and drug release.

Example 34. Use of Liquid Pharmaceutical Excipients in Gallate Based Pastes

Various additional water/soluble/miscible liquids were explored (in addition to propylene glycol and polyethylene glycol) as excipients in gallate based pastes. This involved determining the solubility of EGCG or tannic acid in the excipient, followed by looking at the dissolution of lidocaine at a minimum of 10% w/w followed by the addition of water to see if the paste immediately dissolves, or if it forms a waxy implant.

A viscosity score was established as follows: 1) Fluid—22 gauge needle; 2) Semi Viscous—18 gauge needle; 3) Viscous—16 gauge needle; 4) Waxy Pellet in water. Samples tested included 100 mg of each formulation at max gallate concentration+10% lidocaine in water.

Table 2, below, shows the results for various excipients with EGCG.

TABLE 2

Paste characteristics for various excipients with EGCG.

| Excipient with EGCG | Solubility of EGCG in excipient | Solubility of lidocaine at 10% loading | Viscosity of excipient with EGCG and lidocaine | Pellet in water-intactness at 24 hours |
|---|---|---|---|---|
| Glycerol | 30% | Yes | 2 | Intact |
| Tween 80 | 15% | Yes | 3-4 | 50% gone |
| Pluronic I101 | 20% | Yes | 3-4 | 50% gone |
| Labrasol | 30% | Almost all - bit grainey | 2 | Intact |
| Transcutol | 40%+ | Yes | 1-2 | 50% |
| Cremophor | 20% | Yes | 4 | Dissolved |
| Glyceryl caprylate | <20% | No | 3 | 50% |

Table 3, below, shows the results for various excipients with tannic acid.

TABLE 3

Paste characteristics for various excipients with tannic acid.

| Excipient with tannic acid | Solubility of tannic acid in excipient | Solubility of lidocaine at 10% loading | Viscosity of excipient with tannic and lidocaine | Pellet in water-intactness at 24 hours |
|---|---|---|---|---|
| Glycerol | 30% | Yes | 2 | Intact |
| Tween 80 | 15% | Yes | 3-4 | 50% gone |
| Pluronic I101 | 20% | Yes | 3-4 | 50% gone |
| Labrasol | 30% | Yes-very clear | 2 | Intact |
| Transcutol | 40%+ | Yes | 2 | Intact |
| Cremophor | 20% | Yes | 4 | Dissolved |
| Glyceryl caprylate | <20% | No | 3 | 50% |

Aspects

1. A medical device comprising: a base structure having a surface, and a coating on the surface comprising water-insoluble therapeutic agent solubilized within a matrix of gallate-containing compound.

2. The medical of claim 1, wherein the gallate containing compound and the water-insoluble therapeutic agent are present at a weight ratio of between 1 to 40 and 500 to 1 gallate containing compound to water-insoluble therapeutic agent 3. The medical device of claim 1, wherein the coating is free of an additional polymer or non-polymer carrier modifying a rate of release of the therapeutic agent.

4. The medical device of any preceding claim, wherein the gallate containing compound is selected from a group consisting of epi gallo catechin gallate, tannic acid and epi catechin gallate.

5. The medical device of any preceding claim, wherein the gallate containing compound comprises a gallate substituted molecule such as a dendrimer, a polymer, a macromolecule or a small molecule.

6. The medical device of any preceding claim, wherein the gallate containing compound is tannic acid.

7. The medical device of any one of claims 1 to 5, wherein the gallate containing compound is epi gallo catechin gallate.

8. The medical device of any preceding claim, wherein the gallate containing compound and the water-insoluble therapeutic agent are present at a weight ratio of between 30 to 1 and 500 to 1 gallate containing compound to water-insoluble therapeutic agent.

9. The medical device of any preceding claim, wherein the water-insoluble therapeutic agent is contained within a matrix of the gallate containing compound and wherein the water-insoluble therapeutic agent are present at a weight ratio of between 30 to 1 and 100 to 1 gallate containing compound to water-insoluble therapeutic agent.

10. The medical device of any preceding claim, wherein the implantable medical device is an expandable device.

11. The medical device of claim 10, wherein the expandable device is a balloon.

12. The medical device of claim 10, wherein the expandable device is a stent.

13. The medical device of any one of claims 1 to 8, wherein the medical device is selected from the group consisting of a stent, a vascular stent, a ureteral stent, a catheter, a balloon, a balloon catheter, a stent graft, a wire guide, and a cannula.

14. The medical device of any preceding claim, wherein the water-insoluble therapeutic agent is an immunosuppressive agent, an antiproliferative agent, a microtubule stabilizing agent, a restenosis-inhibiting agent, or an inhibitor of the mammalian target of rapamycin.

15. The medical device of claim 14, wherein the water-insoluble therapeutic agent is a taxane compound.

16. The medical device of claim 15, wherein the taxane compound is paclitaxel or docetaxel.

17. The medical device of claim 14, wherein the therapeutic agent is a macrolide immunosuppressive agent.

18. The medical device of claim 17, wherein the macrolide immunosuppressive agent is sirolimus, pimecrolimus, tacrolimus, everolimus, zotarolimus, novolimus, myolimus, temsirolimus, deforolimus, or biolimus.

19. The medical device of any proceeding claim, wherein the coating layer is adhered directly to the surface of the base structure.

20. The medical device of any one of claims 1 to 19, wherein the gallate containing compound is present in an amount effective to increase the rate of release of the water-insoluble therapeutic agent from the coating.

21. The medical device of any proceeding claim, wherein the coating consists essentially of the water-insoluble therapeutic agent and the gallate containing compound 22. The medical device of any preceding claim, wherein the gallate containing compound is present in an amount effective to increase the rate of release of the water-insoluble therapeutic agent from the device when immersed in an aqueous solution under static conditions at 37° C.

23. A medical device comprising:
a base structure, and
a composition comprising a gallate containing compound and a water-insoluble therapeutic agent, wherein the gallate containing compound and the water-insoluble therapeutic agent are present at a weight ratio of between 1 to 40 and 500 to 1 and wherein the composition is at least partially incorporated into the base structure.

24. The medical device of claim 23, wherein the base structure comprises a polymeric particle or material.

25. A method for delivering a water-insoluble therapeutic agent locally to tissue of a patient, comprising contacting a vessel wall of the patient with the medical device of any one of claims 1 to 22, and maintaining the device in contact with the vessel wall for a time sufficient to deliver the water-insoluble therapeutic agent to the tissue of the patient, wherein the gallate containing compound enhances delivery of the bioactive to the tissue.

26. A method for manufacturing a medical device, comprising: applying a flowable medium comprising liquid, a water-insoluble therapeutic agent and a gallate containing compound to a surface of an implantable medical device structure or to a surface of a coating layer carried by the implantable medical device structure; and removing liquid from the medium to form a coating layer comprising the water-insoluble therapeutic agent and the gallate containing compound.

27. The method of claim 26, wherein the gallate containing compound is epi gallo catechin gallate.

28. The method of claim 26, wherein the gallate containing compound is tannic acid.

29. The method of any of claims 26 to 28, wherein the removing comprises evaporating.

30. The method of any of claims 26 to 29, wherein the implantable medical device is an expandable device.

31. The method of claim 30, wherein the expandable device is a balloon.

32. The method of claim 31, wherein the balloon is a vascular angioplasty balloon.

33. The method of claim 30, wherein the expandable device is a stent.

34. The method of any one of claims 26 to 33, wherein the water-insoluble therapeutic agent is a taxane.

35. The method of claim 34, wherein the taxane is paclitaxel or docetaxel.

36. The method of any of claims 26 to 33, wherein the water-insoluble therapeutic agent is an inhibitor of the mammalian target of rapamycin.

37. The method of claim 36, wherein the inhibitor of the mammalian target of rapamycin is a macrolide immunosuppressive agent.

38. The method of any one of claims 26 to 37, wherein the water-insoluble therapeutic agent is present in the flowable medium in a weight ratio in the range of 500:1 to 1:40 with respect to the gallate containing compound.

39. A method for treating a patient suffering from a disease or condition, comprising: implanting in the patient an implantable medical device according to any one of claims 1 to 24 for a time sufficient to deliver a therapeutically effective amount of the water-insoluble therapeutic agent to a tissue of the patient, wherein the gallate containing compound enhances delivery of the water-insoluble therapeutic agent to the tissue.

40. The method of claim 39, wherein the gallate containing compound and water-insoluble drug are encapsulated in a matrix that allows subsequent release of the drug, wherein the matrix comprises a composition selected from the group consisting of a polymeric microsphere, a nanoparticle, a film and a paste.

41. The method of claim 39, wherein the medical device is selected from the group consisting of a stent, a vascular stent, a ureteral stent, a catheter, a balloon, a balloon catheter, a stent graft, a wire guide, an embolic device and a cannula.

42. The method of claim 39, wherein the water-insoluble therapeutic agent is an immunosuppressive agent, an antiproliferative agent, a microtubule stabilizing agent, a restenosis-inhibiting agent, or an inhibitor of the mammalian target of rapamycin.

43. The method of claim 42, wherein the water-insoluble therapeutic agent is a taxane.

44. The method of claim 43, wherein the taxane is paclitaxel.

45. The method of claim 42, wherein the water-insoluble therapeutic agent is a macrolide immunosuppressive agent.

46. The method of claim 45, wherein the macrolide immunosuppressive agent is sirolimus, pimecrolimus, tacrolimus, everolimus, zotarolimus, novolimus, myolimus, temsirolimus, deforolimus, or biolimus.

47. A method for treating a patient suffering from a disease or condition, comprising: administrating a composition comprising a therapeutically effective amount of a gallate containing compound and a water-insoluble therapeutic agent are present at a weight ratio of between 30 to 1 and 500 to 1 gallate containing compound to water-insoluble therapeutic agent, wherein the gallate containing compound enhances delivery of the water-insoluble therapeutic agent to a tissue of the patient.

48. A method for treating a patient suffering from a disease or condition, comprising: administering a topical preparation to the skin of a patient at an area in need of treatment, the preparation comprising a therapeutically effective amount of a gallate containing compound and a water-insoluble drug.

49. The method of claim 48, where the drug is selected from paclitaxel, docetaxel, amphotericin, curcumin, retinoic acid, finasteride, and lidocaine.

50. The method of claim 48, where the gallate containing compound is selected from epi gallo catechin gallate and tannic acid.

51. The method of claim 48, where the preparation comprises a cream, paste, gel, or ointment.

52. A method for treating a patient suffering from a disease or condition, comprising: administering a pharmaceutical preparation to a patient, the preparation comprising a therapeutically effective amount of a gallate containing compound and a water-insoluble drug, where the administering comprises injecting the preparation into the patient at an area in need of treatment, and where the preparation is formulated to form a partially water-insoluble pellet when injected into the patient that controllably releases the drug at the area in need of treatment.

53. The method of claim 52, where the preparation is formulated to release the drug in the body over a period of at least two days.

54. The method of claim 52, where the preparation is formulated to release the drug in the body over a period of at least seven days.

55. The method of claim 52, where the preparation is formulated to release the drug in the body over a period of at least two weeks.

56. The method of claim 52, where the drug is selected from paclitaxel, docetaxel, amphotericin, curcumin, retinoic acid, finasteride, and lidocaine.

57. The method of claim 52, where the gallate containing compound is selected from epi gallo catechin gallate and tannic acid.

58. The method of claim 52, where the preparation is a paste.

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

I claim:

1. A composition for the treatment of a medical condition, comprising:
    a topical drug preparation comprising a gallate containing compound and a water-insoluble drug, where the gallate containing compound is present in an amount effective in increasing the dermal uptake of the drug, where the gallate containing compound is present in an amount by weight equal to or greater than the amount by weight of the water-insoluble drug.

2. The composition of claim 1, where the gallate containing compound is selected from the group consisting of epi gallo catechin gallate and tannic acid.

3. The composition of claim 1, where the drug is selected from paclitaxel, docetaxel, amphotericin, curcumin, retinoic acid, finasteride, and lidocaine.

4. The composition of claim 1, where the drug has a molecular weight greater than 500 Daltons.

5. The composition of claim 1, further comprising a solubilizing excipient.

6. The composition of claim 1, where the topical drug preparation comprises a eutectic solution.

7. The composition of claim 1, where the weight ratio of gallate containing compound:water-insoluble drug is in the range of 200:1 to 1:1, 200:1 to 5:1, 200:1 to 10:1, 200:1 to 30:1, 200:1 to 50:1, 100:1 to 1:1, 100:1 to 5:1, 100:1 to 10:1, 100:1 to 30:1, 100:1 to 50:1, 50:1 to 1:1, 50:1 to 5:1, 10:1 to 1:1, or 10:1 to 5:1.

8. The composition of claim 1, where the topical preparation comprises a cream, paste, gel, or ointment.

9. The composition of claim 1, where the topical preparation comprises a preblended solid or semi solid matrix of the gallate containing compound and the drug.

10. The composition of claim 1, where the gallate containing compound and the drug are predispersed in one of a membrane, a hydrogel, an electrospun film, or a skin dressing.

11. The composition of claim 1, where the preparation is nonaqueous.

12. A composition for the treatment of a medical condition, comprising:
a nonaqueous pharmaceutical preparation comprising a gallate containing compound and a water-insoluble drug, where the preparation is formulated to form a partially water-insoluble mass when placed in an aqueous medium, that gradually releases the drug into the aqueous medium in a controlled manner.

13. The composition of claim 12, where the preparation is formulated to release the drug into the aqueous medium over a period of at least two days.

14. The composition of claim 12, where the preparation is formulated to release the drug into the aqueous medium over a period of at least two weeks.

15. The composition of claim 12, where the gallate containing compound is present in an amount effective in increasing the solubility of the water-insoluble drug in an aqueous medium.

16. The composition of claim 12, where the gallate containing compound is present in an amount by weight equal to or greater than the amount by weight of the water-insoluble drug.

17. The composition of claim 12, where the gallate containing compound is selected from the group consisting of epi gallo catechin gallate and tannic acid.

18. The composition of claim 12, where the drug is selected from paclitaxel, docetaxel, amphotericin, curcumin, retinoic acid, finasteride, and lidocaine.

19. The composition of claim 12, further comprising a solubilizing excipient selected from the group consisting of glycerol, poloxamer, propylene glycol, and polyethylene glycol.

* * * * *